United States Patent
Schüler et al.

(10) Patent No.: US 9,913,918 B2
(45) Date of Patent: Mar. 13, 2018

(54) PRODUCTION OF MAGNETIC NANOPARTICLES IN RECOMBINANT HOST CELLS

(71) Applicant: UNIVERSITAT BAYREUTH, Bayreuth (DE)

(72) Inventors: Dirk Schüler, Neuried (DE); Isabel Kolinko, Planegg (DE)

(73) Assignee: UNIVERSITAT BAYREUTH, Bayreuth (DE)

( * ) Notice: Subject to any disclaimer, the term of this patent is extended or adjusted under 35 U.S.C. 154(b) by 0 days.

(21) Appl. No.: 14/897,237

(22) PCT Filed: Jun. 10, 2014

(86) PCT No.: PCT/EP2014/061987
§ 371 (c)(1),
(2) Date: Dec. 9, 2015

(87) PCT Pub. No.: WO2014/198701
PCT Pub. Date: Dec. 18, 2014

(65) Prior Publication Data
US 2016/0296643 A1    Oct. 13, 2016

(30) Foreign Application Priority Data

Jun. 10, 2013 (EP) ..................... 13171319
Nov. 19, 2013 (EP) ..................... 13193478

(51) Int. Cl.
| | |
|---|---|
| C12N 1/20 | (2006.01) |
| C12N 15/00 | (2006.01) |
| C12N 15/74 | (2006.01) |
| C12P 21/06 | (2006.01) |
| C12P 19/34 | (2006.01) |
| A61K 49/18 | (2006.01) |
| C07K 14/195 | (2006.01) |
| C12P 3/00 | (2006.01) |

(52) U.S. Cl.
CPC ........ *A61K 49/1896* (2013.01); *C07K 14/195* (2013.01); *C12N 15/74* (2013.01); *C12P 3/00* (2013.01)

(58) Field of Classification Search
CPC ....... A61K 49/1896; C12P 3/00; C12N 15/74; C07K 14/195
USPC .................. 435/252.3, 320.1, 471, 69.1, 91.1
See application file for complete search history.

(56) References Cited

U.S. PATENT DOCUMENTS

2010/0292495 A1* 11/2010 Schuler .............. A61K 49/1824 556/1
2013/0183758 A1* 7/2013 Bell, III .................. C12N 5/00 435/454

FOREIGN PATENT DOCUMENTS

WO    2009047301 A1    4/2009

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Kessi et al., Reduction of selenite and detoxification of elemental selenium by phototrophic bacterium Rhodospirillum rubrum. Appl. Environ. Microbiol., 1999, vol. 65 (11): 4734-4740.*
Kisselev L., Polypeptide release factors in prokaryotes and eukaryotes: same function, different structure. Structure, 2002, vol. 10: 8-9.*
Rong et al., Ferrous iron transport proetin B gene (feoB1) plays an accessory role in magnetosome formation in Magnetospirillum gryphiswaldense Res. Microbiol., 2008, vol. 159: 530-536.*
Seffernick et al., Melamine deaminase and Atrazine chlorohydrolase: 98 percent identical but functionally different. J. Bacteriol., 2001, vol. 183 (8): 2405-2410.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Alphaproteobacterium, 4 pages downloaded from https://en.wikipedia.org/wiki/ on Jun. 8, 2017.*
Fong, C. et al.: "FeoB2 Functions in Magnetosome Formation and Oxidative Strees Protection in Magnetospirillum gryphiswaldense Strain MSR-1", Journal of Bacteriology, vol. 194, No. 15, May 25, 2012, pp. 3972-3976.

(Continued)

*Primary Examiner* — Ganapathirama Raghu
(74) *Attorney, Agent, or Firm* — Edell, Shapiro & Finnan, LLC

(57) ABSTRACT

Recombinant host cells are provided. The cell genome contains heterologous gene expression cassettes capable of being expressed in the host cell, where the gene expression cassettes encode a nucleic acid sequence encompassing at least 80% of the full-length sequence of the mamAB operon, the mamGDFC operon, and the tmms6 operon of a magnetotactic alphaproteobacterium, respectively. The cells may further comprise gene expression cassettes capable of being expressed in the host cell, where the gene expression cassettes encode a nucleic acid sequence encompassing at least 80% of the full-length sequence of the mamXY operon and/or the feoABI operon of a magnetotactic alphaproteobacterium; where the recombinant host cell, upon expression of the gene expression cassettes in their entirety, is capable of producing magnetic nanoparticles. Preferably, the recombinant host cell is derived from *Rhodospirillum rubrum*. Methods of producing these recombinant host cells by genetic transposition are provided.

23 Claims, 19 Drawing Sheets

(56) References Cited

OTHER PUBLICATIONS

International Search Report for International Application PCT/EP2014/061987; dated Oct. 21, 2014.

Jogler, Christian et al.: "Genomics, Genetics and Cell Biology of Magnetosome Formation", Annual Review of Microbiology, vol. 63, No. 1, Oct. 1, 2009, pp. 501-521.

Kolinko, Isabel et al.: "Biosynthesis of magnetic nanostructures in a foreign organism by transfer of bacterial magnetosome gene clusters", Nature Nanotechnology, Feb. 1, 2014.

Lohsse, Anna et al.: "Functional Analysis of the Magnetosome Island in Magnetospirillum gryphiswaldense: The mamAB Operon Is Sufficient for Magnetite Biomineralization". PLOS One, vol. 6, No. 10, Oct. 17, 2011; p. e25561.

Murat, Dorothee et al.: "The magnetosome membrane protein, MmsF, is a major regulator of magnetite biomineralization in Magnetospirillum magneticum AMB-1", Molecular Microbiology, vol. 85, No. 4, Jul. 10, 2012 pp. 684-699.

Scheffel, Andre et al.: "The major magnetosome proteins MamGFDC are not essential for magnetite biomineralization in Magnetospirillum gryphiswaldense but regulate the size of magnetosome crystals", Journal of Bacteriology, American Society for Microbiology, Washington, DC; US, vol. 190, No. 1, Jan. 1, 2008, pp. 377-386.

Schuler, Dirk: "Genetics and cell biology of magnetosome formation in magetotactic bacteria", Fems Microbiology Reviews, Elsevier, Amsterdam; NL, vol. 32, No. 4, Jul. 1, 2008; pp. 654-672.

Yang, Jing et al.: "MamX encoded by the mamXY operon is involved in control of magnetosome maturation in Magnetospirillum gryphiswaldense MSR-1", BMC Microbiology, BioMed Central Ltd, GB, vol. 13, No. 1, Sep. 11, 2013, p. 203.

\* cited by examiner

PRODUCTION OF MAGNETIC NANOPARTICLES IN RECOMBINANT HOST CELLS This application is a U.S. National Stage Application of PCT/EP2014/061987 filed Jun. 10, 2014, which claims priority to European Patent Application No. 13171319.0 filed Jun. 10, 2013, and European Patent Application No. 13193478.8 filed Nov. 19, 2013. The entire contents of the above-identified applications are hereby incorporated by reference.

INCORPORATION OF SEQUENCE LISTING

This application contains a sequence listing submitted electronically via EFS-web, which serves as both the paper copy and the computer readable form (CRF) and consists of a file entitled "14-897237_corr_sequence_listing.txt", which was created on Jul. 5, 2016, which is 55,507 bytes in size, and which is herein incorporated by reference in its entirety.

FIELD OF THE INVENTION

The present invention relates to recombinant host cells being genetically engineered to allow for the homologous or heterologous high-yield production of magnetic nanoparticles, preferably of magnetosomes derived from magnetotactic bacteria. More specifically, the recombinant host cells comprise in their genome the entire genetic information sufficient to express the biosynthetic pathway for the production of magnetic nanoparticles.

BACKGROUND OF THE INVENTION

Magnetic nanoparticles typically comprise nanocrystals made of oxides (or to a lesser extent of sulfides) of the elements in the forth row of the periodic table (i.e. Cr, Mn, Fe, Co, and Ni). The ability to produce such magnetic nanoparticles is inevitable not only for the general understanding of magnetic properties in a nanometer regime, but also for manifold technical applications ranging from magnetic resonance imaging, drug delivery, catalysts, and biosensing to nanoelectronics, semiconductor materials, and magnetic storage media (reviewed in Lu, A. et al. (2007) *Angew. Chem. Int. Ed.* 46, 1222-1224).

Magnetic nanoparticles can be synthesized chemically through precipitation of the crystals from basic aqueous solutions. However, the production of particularly dimensioned ("tailored") nanocrystals via these synthesis routes is significantly hampered by the broad size distribution of the crystal populations obtained. More recently, the synthesis of nanocrystals has been directed to non-aqueous approaches generally resulting in the formation of crystals having not only an improved overall quality but also a narrower size distribution. Nevertheless, in most chemical syntheses reported so far only sub-gram to low gram quantities of monodisperse nanocrystals were obtained, not sufficient for many applications. Furthermore, only a fraction of such synthetic particles constitutes monocrystalline particles having defined magnetic properties. Typically, however, the resulting particles were too small for clinically relevant applications such as magneto-hyperthermic treatment of tumors (Park, J. et al. (2004) *Nature Materials* 3, 891-895).

Alternatively, biogenic magnetic nanoparticles can be employed that are produced by magnetotactic organisms, predominantly magnetotactic bacteria. The ability of magnetotactic bacteria to orient in the Earth's magnetic field is based on the presence of specific organelles, the magnetosomes, which are membrane-enveloped monocrystalline crystals of a magnetic mineral that are arranged in chain-like structures within the cell. Magnetosomes display a variety of species-specific shapes within the single magnetic domain size range (reviewed in Bazylinski, D. A. and Frankel, R. B. (2004) *Nature Rev. Microbiol.* 2, 217-230). In the prototypical *Magnetospirillum*, cubo-octahedral nanocrystals of the mineral magnetite ($Fe_3O_4$) having a maximal diameter of 50 nm are synthesized within magnetosome membrane (MM) vesicles. The MM is a phospholipid bilayer of a distinctive biochemical composition. Their specific structural and magnetic properties make these bacterial magnetosomes highly attractive for various nanotechnological and biomedical applications.

However, the biotechnological usability is hampered by the fact that they can only be produced in comparably small amounts due to the methodological difficulties to cultivate magnetotactic bacteria due to fastidious growth requirements. Typically, the cell yields obtained are only about 1 g (fresh weight) per liter of culture, not enough for the large scale production of magnetosomes (Heyen, U. and Schüler, D. (2003) *Appl. Microbiol. Biotechnol.* 61, 536-544). In addition, genetic interference in or manipulation of the genetic pathway for magnetosome production is cumbersome due to the limited availability of molecular tools for the recalcitrant native host cells.

The biogenesis of functional magnetosomes is highly complex and involves the invagination of magnetosome vesicles from the cytoplasmic membrane, the magnetosomal uptake of iron and the crystallization of magnetite particles, as well as their assembly into chains along a dedicated cytoskeletal structure (Komeili, A. et al. (2006) *Science* 311, 242-245; Katzmann, E. et al. (2010) *Mol. Microbiol.* 77, 208-224). Recently, in *M. gryphiswaldense*, genes controlling magnetosome synthesis within several clusters of a larger (115 kb) genomic magnetosome island (MAI) were discovered, which are interspersed by transposases and genes of unknown function (Jogler, C. et al. (2009) *Environ. Microbiol.* 11, 1267-1277; Jogler, C. et al. (2011) *Proc. Natl. Acad. Sci. USA* 108, 1134-1139). Whereas the smaller mamGFDC (2.1 kb), mms6 (3.6 kb) and mamXY operons (5.1 kb) have accessory functions in biomineralization of properly sized and shaped crystals, the large mamAB operon (16.4 kb) encodes proteins essential for iron transport, magnetosome membrane formation, and crystallization of magnetosome particles as well as their assembly and intracellular positioning. However, due to the structural complexity of the magnetosome organelle, current knowledge about particular gene functions is still quite limited and the presumably complex interplay between the numerous factors involved in the production of magnetosomes needs still to be unraveled in closer detail which is further complicated by the limited methodology for genetic manipulation of magnetotactic bacteria that is presently available.

Thus, there is a need for molecular tools as well as corresponding methods in order to improve the yield of biogenic magnetic nanoparticles that can be obtained from bacterial cultures—both in homologous and heterologous genetic backgrounds (i.e. settings). In particular, there remains an ongoing need for techniques that allow for the large-scale production of magnetic nanoparticles in an easy-to-do and cost-efficient manner.

Accordingly, it is an object of the present invention to provide such molecular tools and corresponding methods.

SUMMARY OF THE INVENTION

In one aspect, the present invention relates to a recombinant host cell, comprising in its genome: (i) a gene expression cassette capable of being expressed in the host cell, the gene expression cassette encoding a nucleic acid sequence encompassing at least 80% of the full-length sequence of the mamAB operon of a magnetotactic alpha-proteobacterium; (ii) a gene expression cassette capable of being expressed in the host cell, the gene expression cassette encoding a nucleic acid sequence encompassing at least 80% of the full-length sequence of the mamGDFC operon of a magnetotactic alpha-proteobacterium; and (iii) a gene expression cassette capable of being expressed in the host cell, the gene expression cassette encoding a nucleic acid sequence encompassing at least 80% of the full-length sequence of the mms6 operon of a magnetotactic alpha-proteobacterium; wherein the recombinant host cell, upon expression of the gene expression cassettes in their entirety, is capable of producing magnetic nanoparticles.

In preferred embodiments, the recombinant host cell further comprises: (iv) a gene expression cassette capable of being expressed in the host cell, the gene expression cassette encoding a nucleic acid sequence encompassing at least 80% of the full-length sequence of the mamXY operon of a magnetotactic alpha-proteobacterium; and/or (v) a gene expression cassette capable of being expressed in the host cell, the gene expression cassette encoding a nucleic acid sequence encompassing at least 80% of the full-length sequence of the feoAB1 operon of a magnetotactic alpha-proteobacterium.

In specific embodiments, the recombinant host cell comprises the gene expression cassettes (i) to (v), wherein the gene expression cassettes all encompass the full-length sequences of the respective operons. Particularly, the total length of the gene expression cassettes introduced in the recombinant host cell is less than 35 kb.

In other specific embodiments, the recombinant host cell allows for homologous or heterologous expression of the gene expression cassettes in their entirety.

In further preferred embodiments, the magnetotactic alpha-proteobacterium from which the respective operon sequences are derived is *Magnetospirillum* spec., and in particular *Magnetospirillum gryphiswaldense*.

Preferably, the gene expression cassettes are stably integrated into the host cell's genome.

In specific embodiments, the magnetic nanoparticles are magnetosomes, and in particular magnetosomes consisting of magnetite.

In further specific embodiments, any one or more of the gene expression cassettes are under the control of their respective endogenous regulatory sequences.

In yet further specific embodiments, the recombinant host cell comprises two or more copies of any one or more of the gene expression cassettes.

Preferably, with respect to the recombinant host cell, any one or more of the gene expression cassettes represent heterologous nucleic acid sequences.

In further preferred embodiments, the recombinant host cell is a prokaryotic cell, and particularly derived from an alpha-proteobacterium. Particularly preferably, the recombinant host cell is derived from *Rhodospirillum rubrum*.

In a further aspect, the present invention relates to a method for the production of a recombinant host cell as defined herein, the method comprising the transfer of the gene expression cassettes into the host cell by means of genetic transposition, and in particular comprising a modular transfer of the gene expression cassettes.

In yet another aspect, the present invention relates to the use of a recombinant host cell as defined herein for the biotechnological production of magnetic nanoparticles.

In yet another aspect, the present invention relates to the use of a recombinant host cell as defined herein for the in vivo synthesis of magnetic nanoparticles for application in magnetogenetics or biomedical imaging.

Different colors indicate single genes or operons inserted into the chromosome (oval shape). Dark blue: mamAB operon, green: mamGFDC operon, brown: mms6 operon, pale blue: mamXY operon, red: feoAB1 operon, grey: lacI repressor gene, yellow: antibiotic resistance genes ($km^R$: kanamycin resistance, $tc^R$: tetracycline resistance, $ap^R$: ampicillin resistance, $gm^R$: gentamicin resistance). Red arrows indicate different promoters (P) controlling expression of antibiotic resistance genes ($P_{km}$, $P_{gm}$, $P_{tc}$), repressor genes ($P_{lacI}$) or magnetosome genes ($P_{mms}$, $P_{mamDC}$, $P_{mamH}$, $P_{mamXY}$, $P_{lac}$). Crossed lines indicate gene deletions by homologous recombination, which were introduced into the recipient genome to prove equivalent functions as in the donor organism. IR=inverted repeat defining the boundaries of the sequence inserted by the transposase.

Figure 2:
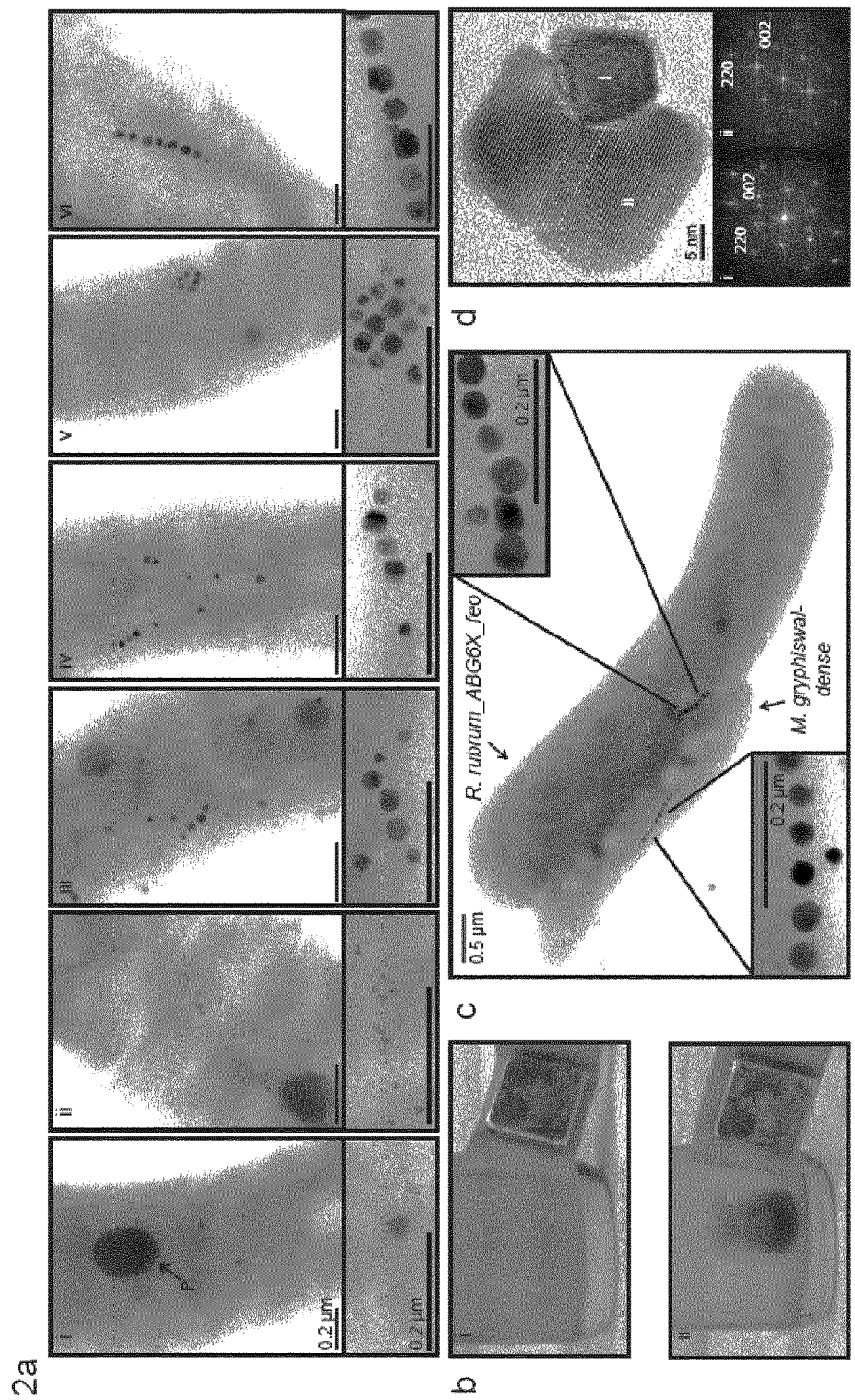

FIG. 2: Phenotypes of *Rhodospirillum rubrum* strains expressing different magnetosome gene clusters and auxiliary genes.

(2a) Transmission electron micrographs. *R. rubrum* wt (i) harbors larger phosphate inclusion (P) and some small, non-crystalline electron-dense particles. *R. rubrum*_ABG6 (ii), *R. rubrum*_ABG6X (iii), *R. rubrum*_ABG6X_ftsZm (iv), *R. rubrum*_ABG6X_dJ (v), *R. rubrum*_ABG6X_feo (vi). Insets show magnifications of non-crystalline electron dense particles or heterologously expressed nanocrystals from (i)-(vi). (ii) *R. rubrum*_ABG6 (mamAB, mamGFDC, and mms6 operons inserted) showed small crystalline particles aligned in a chain-like pattern. (iii) Additional insertion of the mamXY operon lacking ftsZm resulted in formation of larger magnetic particles with an average size of 25 nm (*R. rubrum*_ABG6X). (iv) Additional transposition of ftsZm under control of an inducible lac promoter did not further increase crystal number and size. (v) Deletion of mamJ in *R. rubrum*_ABG6X caused agglomeration of the crystals into clusters. (vi) Additional insertion of feoAB1 into *R. rubrum*_ABG6X resulted in increased magnetosome biomineralization (average crystal diameter 35 nm, formation of longer magnetosome chains of 440 nm). Scale bar: 0.2 µm. For further TEM micrographs see FIG. 13. (2b) Unlike the untransformed wild-type, cells of *R. rubrum*_ABG6X accumulated as a visible red spot near the pole of a permanent magnet at the edge of a culture flask. (2c) TEM micrograph of a mixed culture of the donor *M. gryphiswaldense* and the recipient *R. rubrum*_ABG6X_feo, illustrating characteristic cell properties and magnetosome organization. Insets show magnifications of magnetosomes from *M. gryphiswaldense* and *R. rubrum*_ABG6X_feo. (2d) HRTEM lattice image of a twinned crystal from *R.* rubrum_ABG6X, with the Fourier transforms (i) and (ii) that show intensity maxima consistent with the structures of magnetite, respectively.

Figure 3:
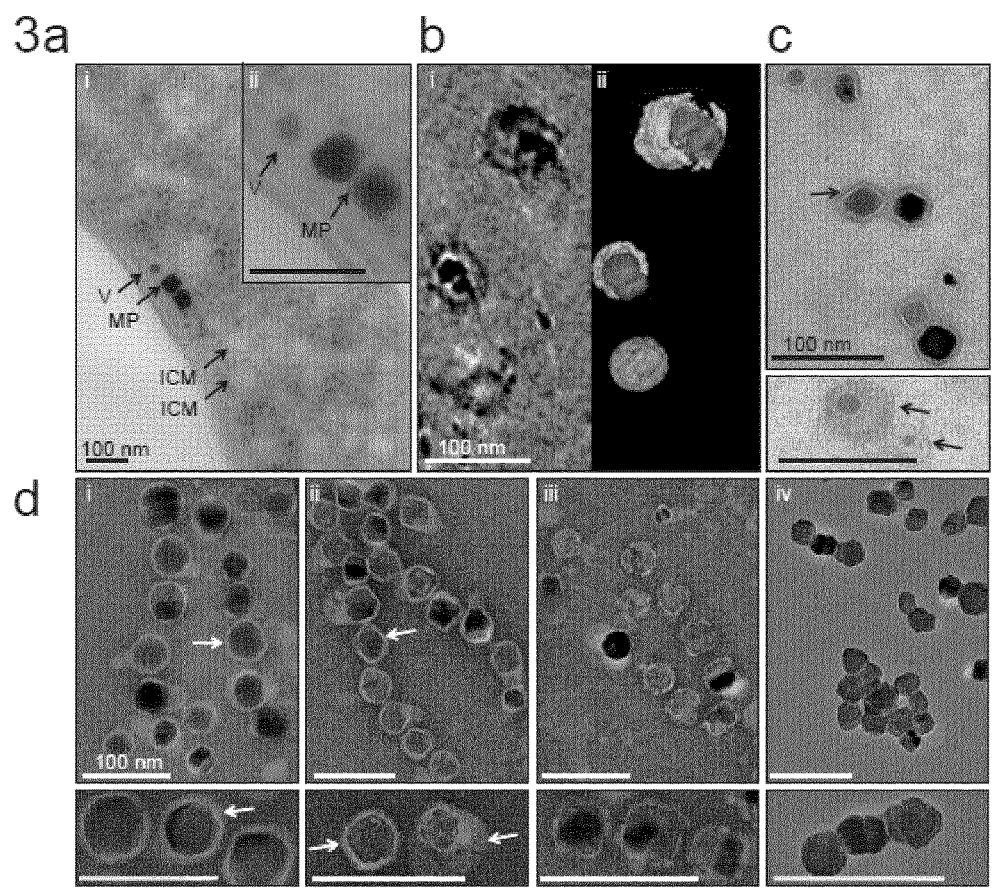

FIG. 3: Ultrastructural analysis of Rhodospirillum rubrum_ABG6X and isolated crystals.

(3a) Cryo-fixed, thin-sectioned R. rubrum_ABG6X harbored intracytoplasmic membranes (ICMs) (93±34 nm, n=95), magnetic particles (MP) and a vesicle (V) enclosing an immature crystal (66±6 nm, ±=s.d., n=7.). The inset shows a magnification of the magnetite crystals. Scale bar: 100 nm. (3b) Cryo-electron tomography (CET) of isolated magnetic particles of R. rubrum_ABG6X: X-Y slice of a reconstructed tomogram (I) and surface-rendered 3D representation (II). A membrane-like structure (thickness 3.4±1.0 nm, n=6) surrounds magnetic particles (red). Yellow: membrane like structure, blue: empty vesicle. Scale bar: 100 nm. (3c and 3d) Transmission electron micrographs of isolated magnetosomes from R. rubrum_ABG6X (3c and 3d (ii), (iii), (iv)) and M. gryphiswaldense (3d (i)) negatively stained by (3c) uranyl acetate or (3d) phosphotungstic acid. Insets show magnifications of respective magnetic particles. Arrows indicate the magnetosome membrane, which encloses magnetic crystals of M. gryphiswaldense (3.2±1.0 nm, n=103) and R. rubrum_ABG6X (3.6±1.2 nm, n=100). Organic material could be solubilized from magnetite crystals of R. rubrum_ABG6X with SDS (iv) and less effective also by Triton X-100 (III). Scale bar: 100 nm.

Figure 4:
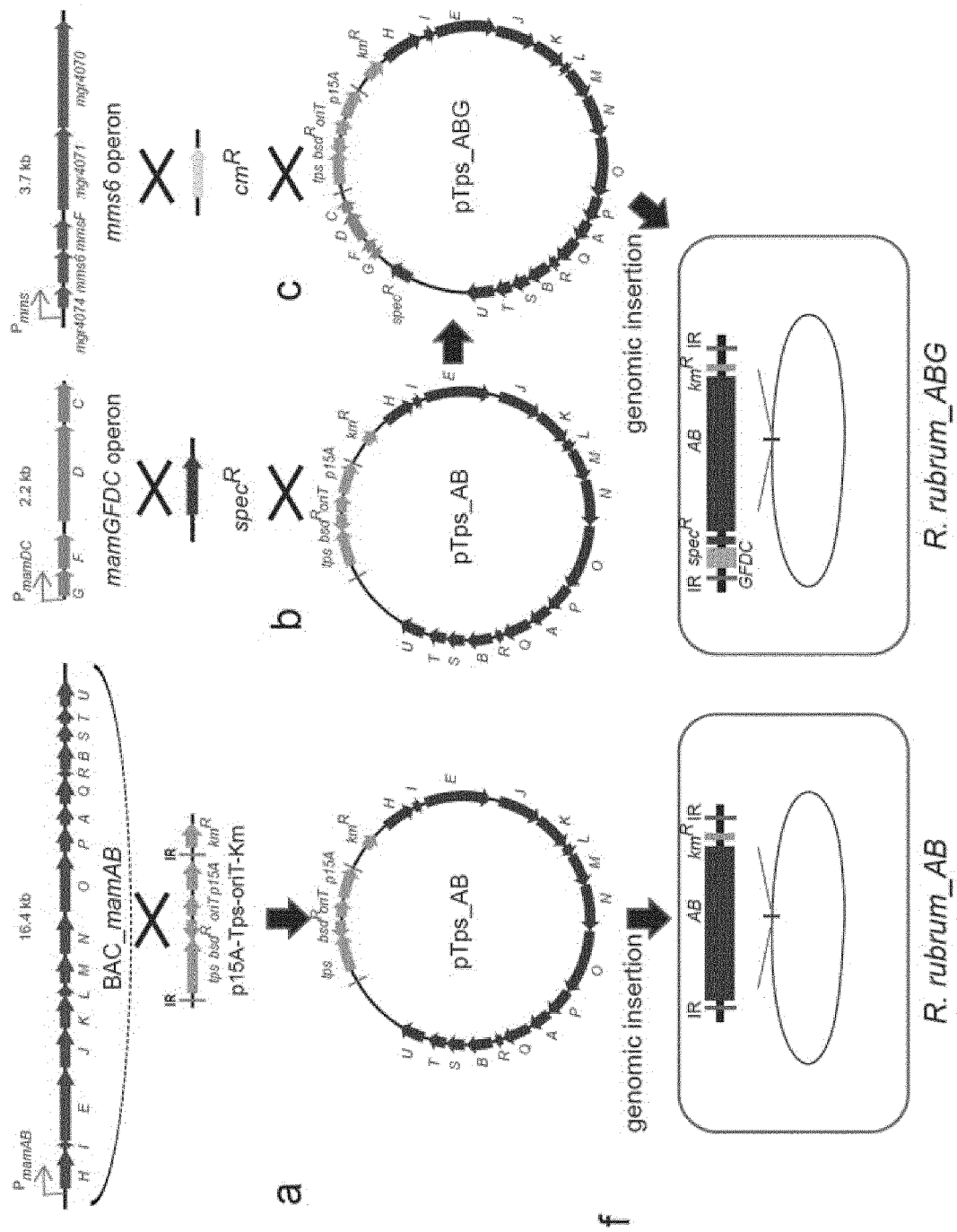
Figure 4:
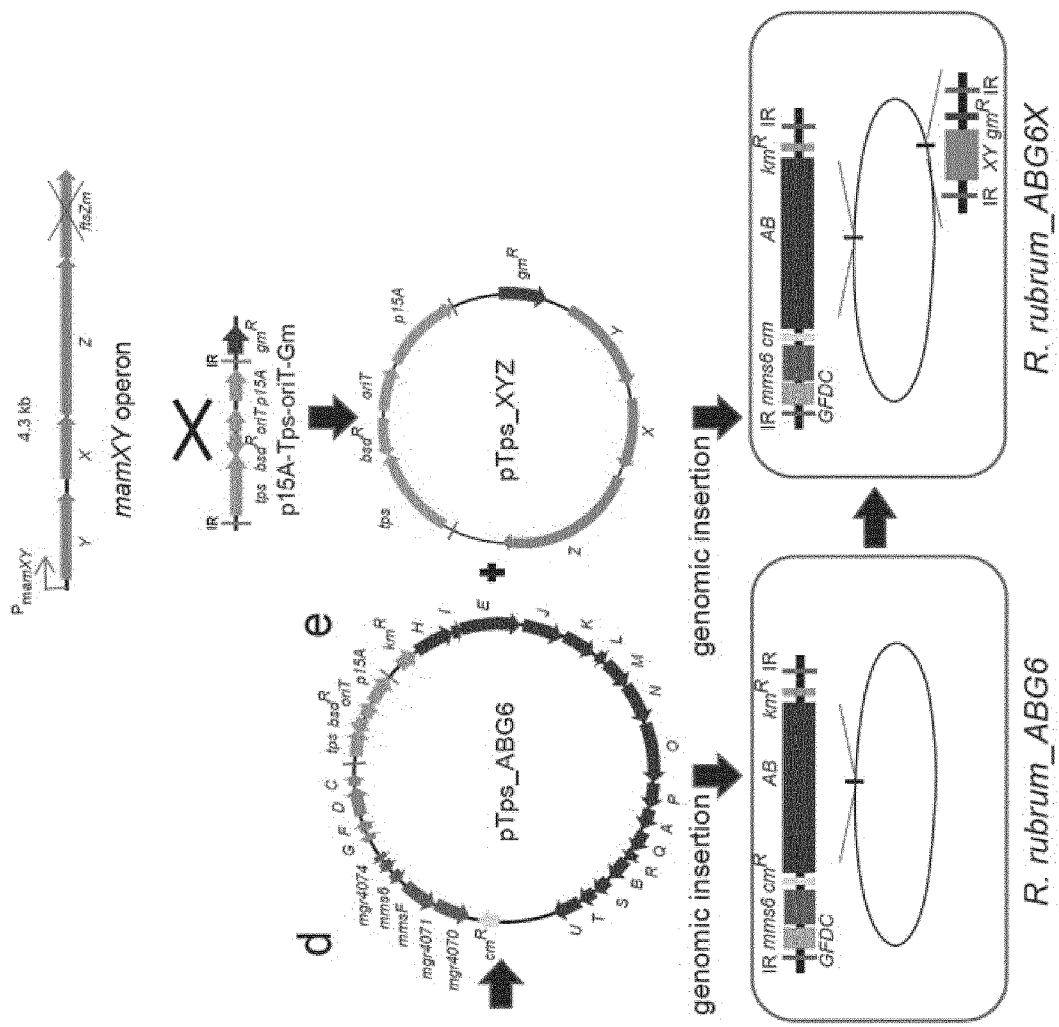
Figure 4:
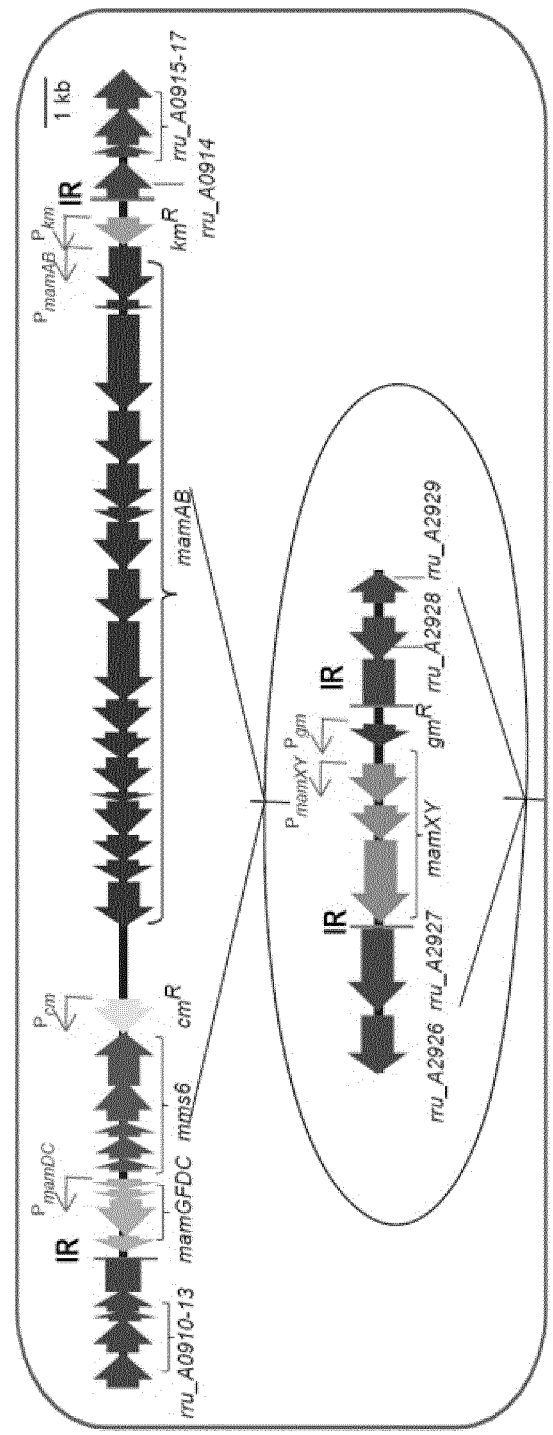

FIG. 4: Construction scheme of insertion cassettes for modular expression of the mam and mms operons.

(4a) Recombinant engineering of a BAC containing the mamAB operon (blue) and a vector backbone (Km-p15A-Tps-oriT-Km, orange) harboring a MycoMar transposase gene (tps), inverted repeats (IR), origin of transfer (oriT), p15A origin of replication (p15A) and a kanamycin$^R$ cassette (km$^R$, orange). (4b) Insertion of a spectinomycin$^R$ cassette (spec$^R$, pink) and the mamGFDC operon (green) into pTps_AB by triple recombination. (4c and 4d) Stitching of pTps_ABG by insertion of the mms6 operon and a chloramphenicol$^R$ cassette. (4e) pTps_XY consisting of a Tps vector backbone (orange), the mamXY operon (pale blue) and a gentamicin$^R$ gene (gm$^R$, purple) was constructed. (4f) Plasmids were transferred by conjugation into R. rubrum. Transposition of the DNA fragments within the IR sequences occurred randomly at TA dinucleotide insertion sites by a "cut and paste" mechanism (Rubin, E. J. et al. (1990) Proc. Natl. Adac. Sci. USA 96, 1645-1650). (4g) Chromosomal insertion sites of the transposed constructs in R. rubrum_ABG6X are shown with adjacent genes (red) as revealed by whole genome sequencing performed with a MiSeq sequencer (Illumina) (accession number of R. rubrum ATCC 11170: NC_007643). pTps_ABG6 inserted within a gene encoding a putative aldehyde dehydrogenase (YP_426002), and pTps_XYZ inserted within rru_A2927, encoding an acriflavin resistance protein (protein accession number YP_428011). Sequences of inserted magnetosome operons matched those of the donor (M. gryphiswaldense) with no detectable mutations, except for a deletion (aa 169-247) within the hypervariable non-essential CAR domain of mamJ, which was shown to be irrelevant for protein function (Scheffel, A. and Schüler, D. (2007) J. Bacteriol. 189, 6437-6446).

Figure 5:
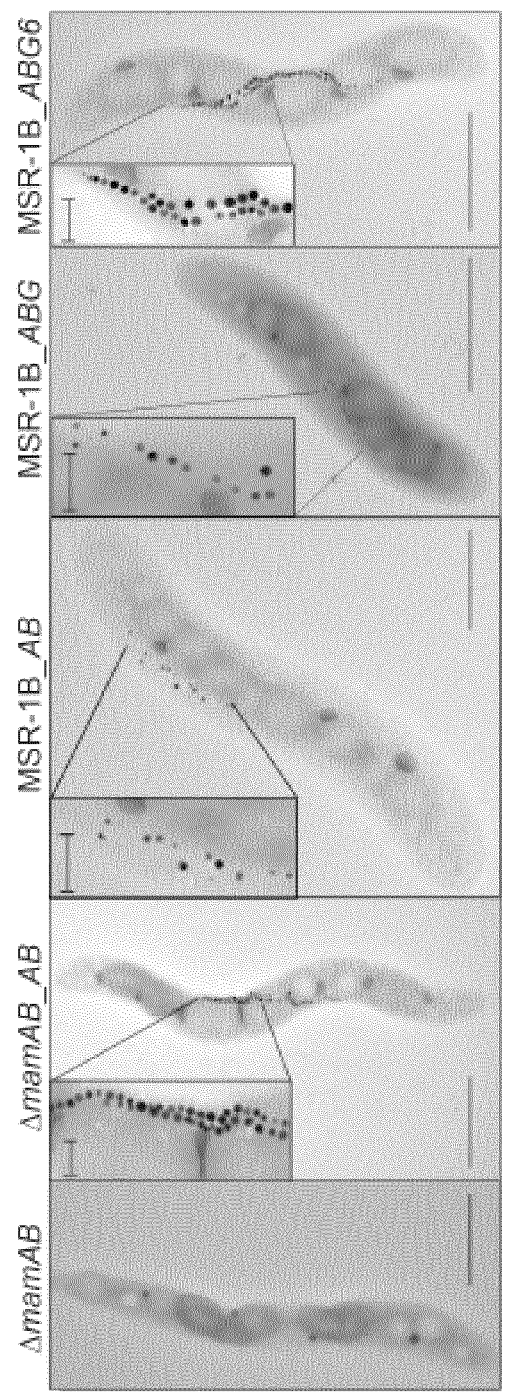

FIG. 5: Transmission electron micrographs of M. gryphiswaldense MSR-1 mutants expressing various insertional transposon constructs.

The plasmids pTps_AB, pTps_ABG and pTps_ABG6 were transferred into the non-magnetic M. gryphiswaldense MSR-1 mutants ΔmamAB and MSR-1B, the latter lacking most of the magnetosome genes except of the mamXY operon (Lohsse, A. et al. (2011) PLoS One 6, e25561). After transfer of pTps_AB, a wt-like phenotype was restored in ΔmamAB_AB as revealed by $C_{mag}$ (1.2±0.2) and measured crystal sizes (37±10 nm) in comparison with M. gryphiswaldense wild-type (36±9 nm, $C_{mag}$=1.4±0.2) (see also Table 1). Mutant MSR-1B was only partly complemented after insertion of pTps_AB and pTps_ABG, that is, $C_{mag}$ and crystal sizes were still lower than in the wild-type (wt) (see also Table 1). Transfer of pTps_ABG6 restored nearly wild-type like magnetosome formation in MSR-1B (35±8 nm, $C_{mag}$=0.9±0.1). ±=s.d. Scale bar: 1 μm, insets: 0.2 μm.

Figure 6:
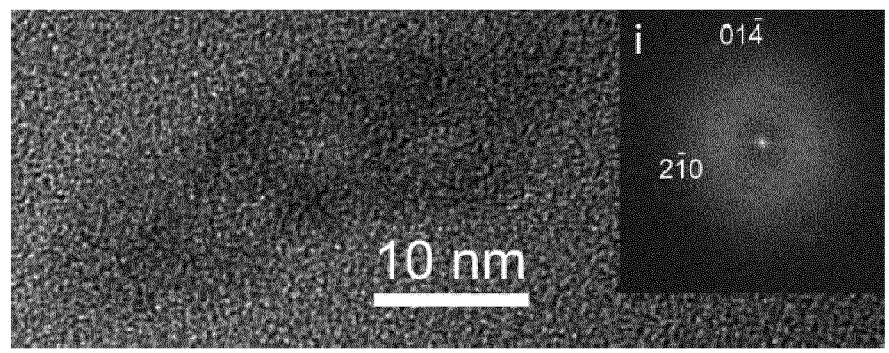

FIG. 6: HRTEM lattice image of a crystal from Rhodospirillum rubrum_ABG6 with the corresponding Fourier transform (i) that shows intensity maxima consistent with the structures of hematite.

Figure 7:
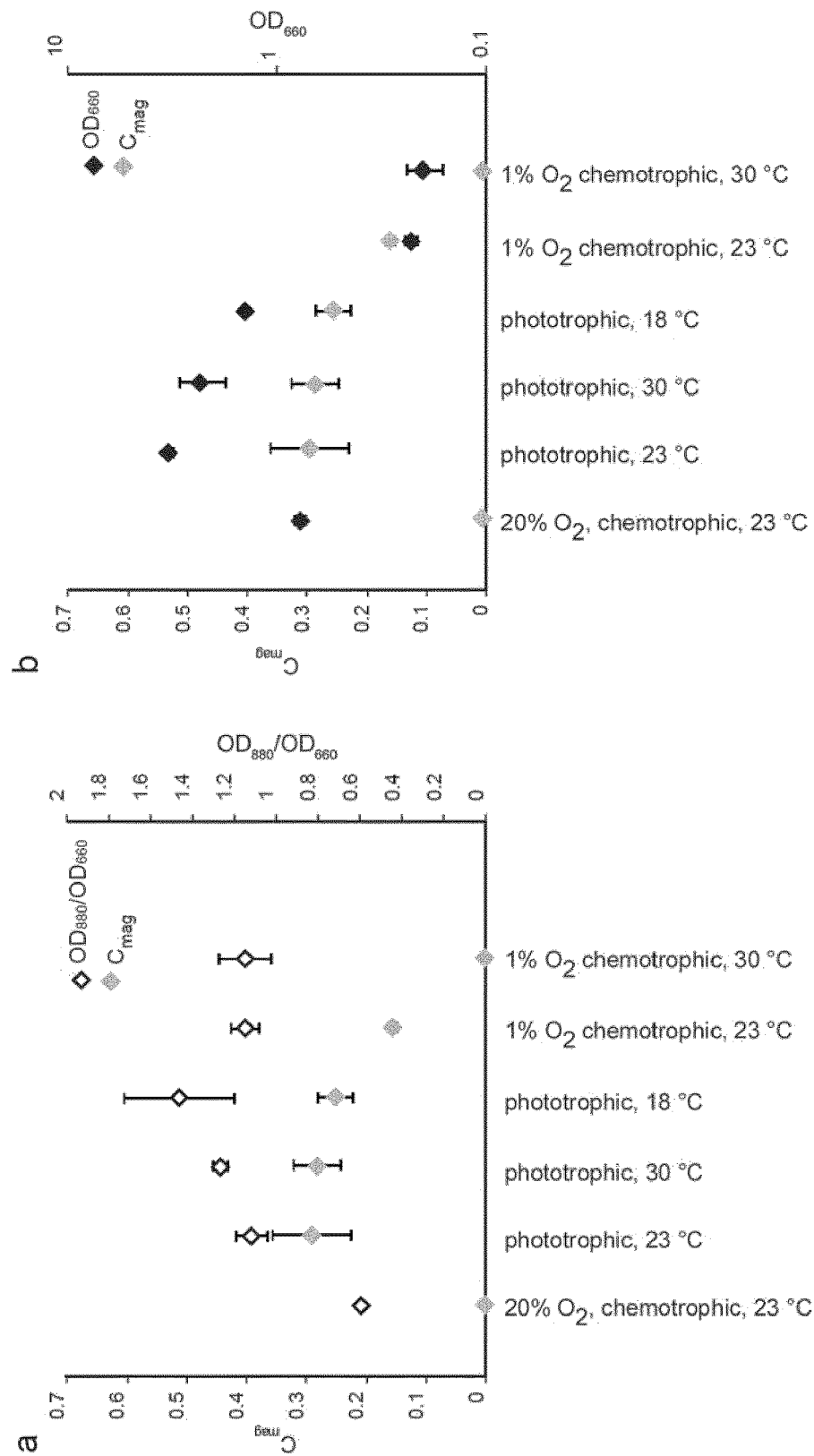
Figure 7:
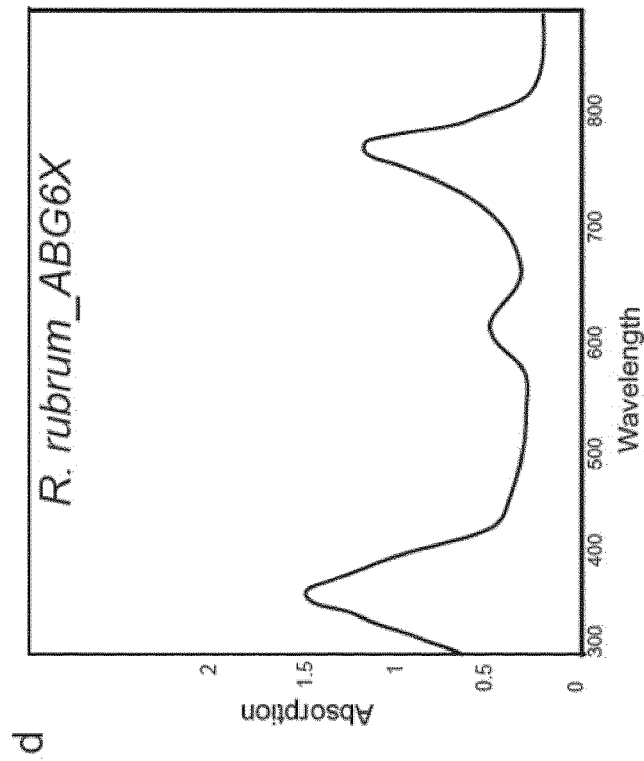
Figure 7:
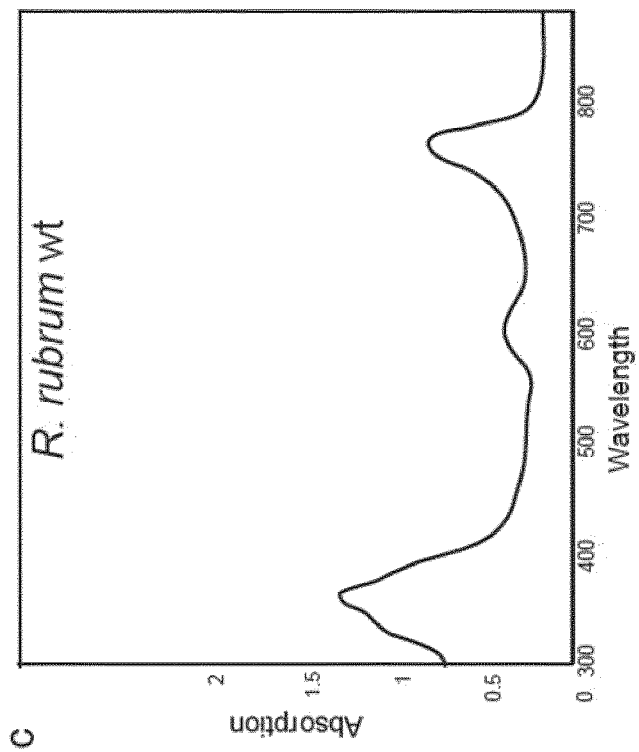

FIG. 7: Growth and magnetic response of Rhodospirillum rubrum_AGB6X cultivated under various growth conditions.

(7a and 7b) Cells were grown in ATCC 112 (chemotrophic, 20% $O_2$), Sistrom A (phototrophic, anoxic) and M2SF (chemotrophic, 1% $O_2$) medium for 3 (30° C.), 4 (23° C.) or 10 (18° C.) days. Optical density at 660 and 880 nm and magnetic response were measured. The ratio $OD_{880}/OD_{660}$ correlates with the amount of chromatophores produced in the cells (median values n=3, error bars indicate s.d.). No $C_{mag}$ was detectable under aerobic and microaerobic conditions at 30° C. Anoxic and microaerobic conditions (23° C.) supported particle formation. Furthermore, absorption spectra of extracted bacteriochlorophylls of R. rubrum WT (7c) and R. rubrum_ABG6X (7d) were directly measured, respectively (phototrophic growth, 30° C.). No differences in absorption spectra were detectable.

Figure 8:
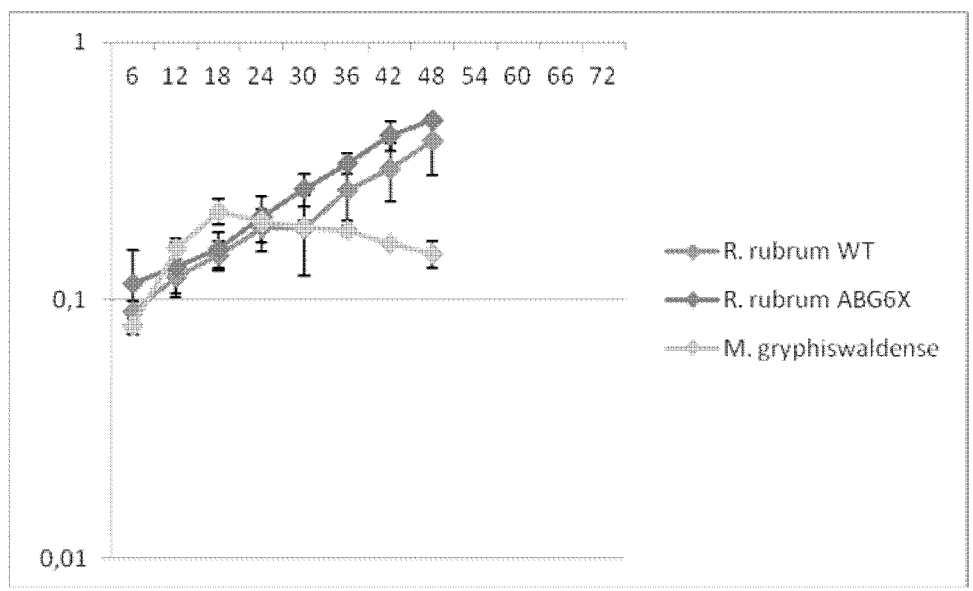

FIG. 8: Growth of Magnetospirillum gryphiswaldense ($OD_{565}$), Rhodospirillum rubrum wt and Rhodospirillum rubrum_ABG6X ($OD_{660}$).

Cells of M. gryphiswaldense (FSM medium) or R. rubrum (Sistrom A medium, 1000 lux) were incubated for 3 days at 23° C. under anaerobic conditions. Growth of the mutant strain ABG6X (median values n=3, error bars indicate s.d.) was indistinguishable from that of the untransformed wild-type (n=3).

Figure 9:
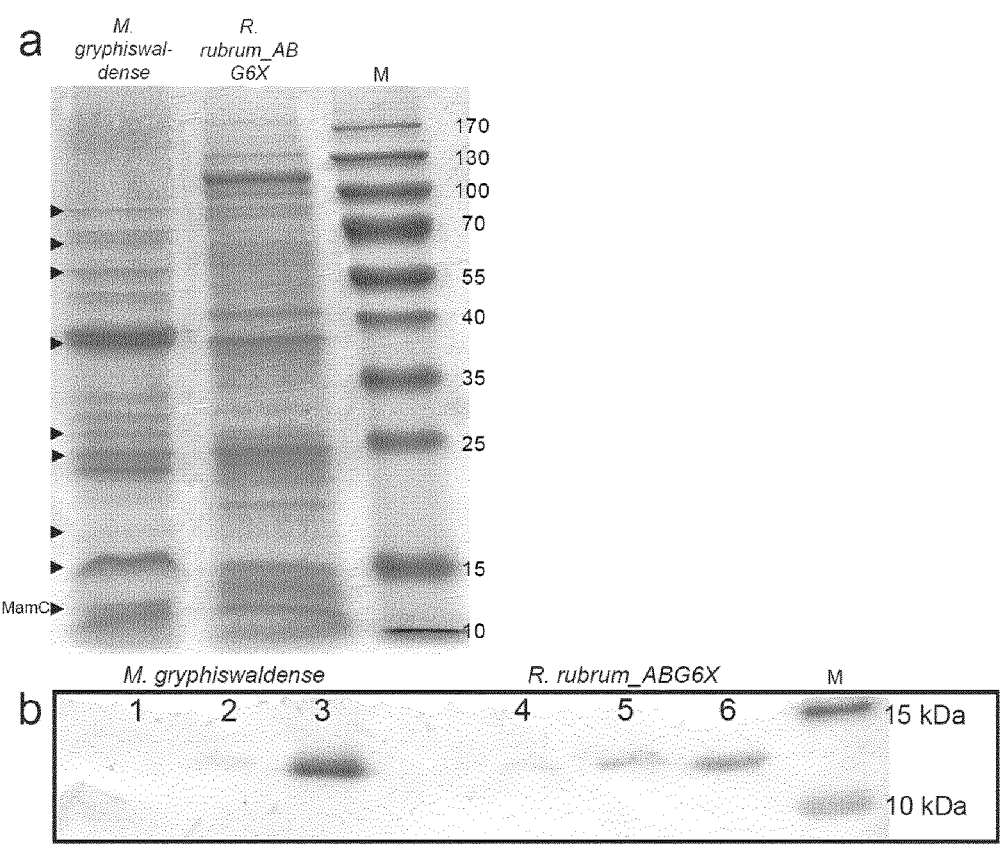

FIG. 9: Proteomic analysis of magnetosomes from Rhodospirillum rubrum_ABG6X (9a) 1D-SDS-PAGE (Comassie blue stained) of proteins solubilized from isolated magnetosome particles of M. gryphiswaldense and R. rubrum_ABG6X. Bands (~90, 70, 60, 40, 30, 25, 20, 15, 12.4 kDa) of the same size are indicated (arrowheads). (9b) Immunodetection of MamC (12.4 kDa) in blotted fractions of M. gryphiswaldense and R. rubrum_ABG6X using an anti-MamC antibody (Lang. C. and Schüler, D. (2008) Appl. Environ. Microbiol. 74, 4944-4953). A signal for MamC was detectable in the magnetic membrane fraction of R. rubrum_ABG6X (6), which was absent from the soluble fraction, but faintly present also in the non-magnetic membrane fraction (5), possibly originating from empty membrane vesicles or incomplete magnetic separation during isolation. Protein extracts from M. gryphiswaldense: 1. soluble fraction, 2. non-magnetic membrane fraction, 3. magnetosome membrane. Protein extracts from R. rubrum_ABG6X: 4. soluble fraction, 5. non-magnetic membrane fraction, 6. magnetic ("magnetosome") membrane fraction. M: marker.

Figure 10:
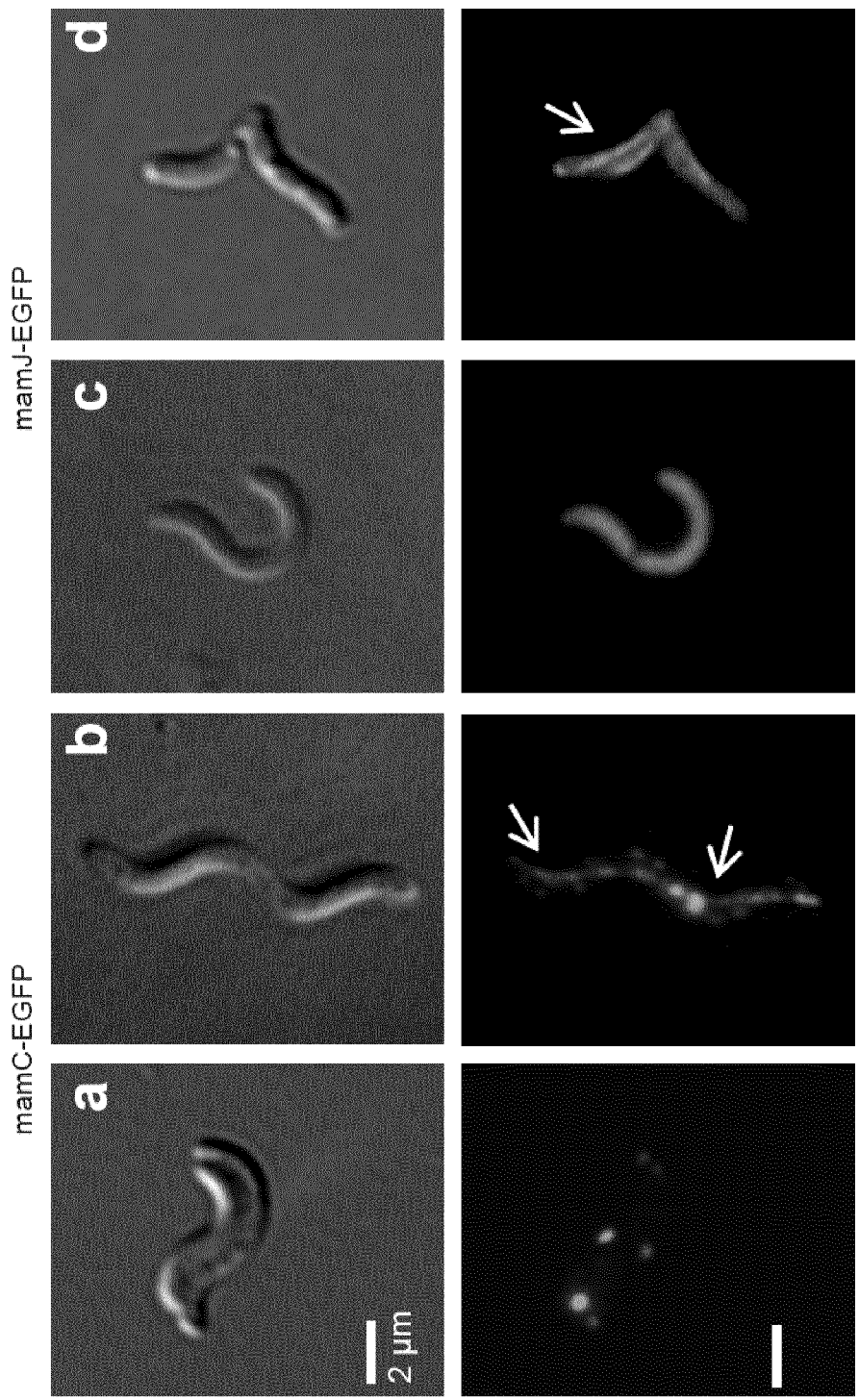

FIG. 10: Fluorescence microscopy of Rhodospirillum rubrum WT and Rhodospirillum rubrum_ABG6X expressing different EGFP-tagged magnetosome proteins.

For localization studies of fluorescently labeled magnetosome proteins, strains were cultivated in ATCC medium overnight at 30° C. with appropriate antibiotics (Table S3). (10a and 10b) MamGFDC with a C-terminal MamC-EGFP fusion expressed in *R. rubrum* wt (n=151) (10a), and *R. rubrum*_ABG6X (n=112) (10b). In the transformed strain, a filamentous structure is visible for 79% of the cells (n=89). (10c and 10d) MamJ-EGFP expressed in *R. rubrum* wt (n=109) (10c), and in *R. rubrum*_ABG6X (n=89) displaying a chain-like fluorescence signal in 63% of the cells (n=56) (10d). Scale bar: 2 µm.

Figure 11:
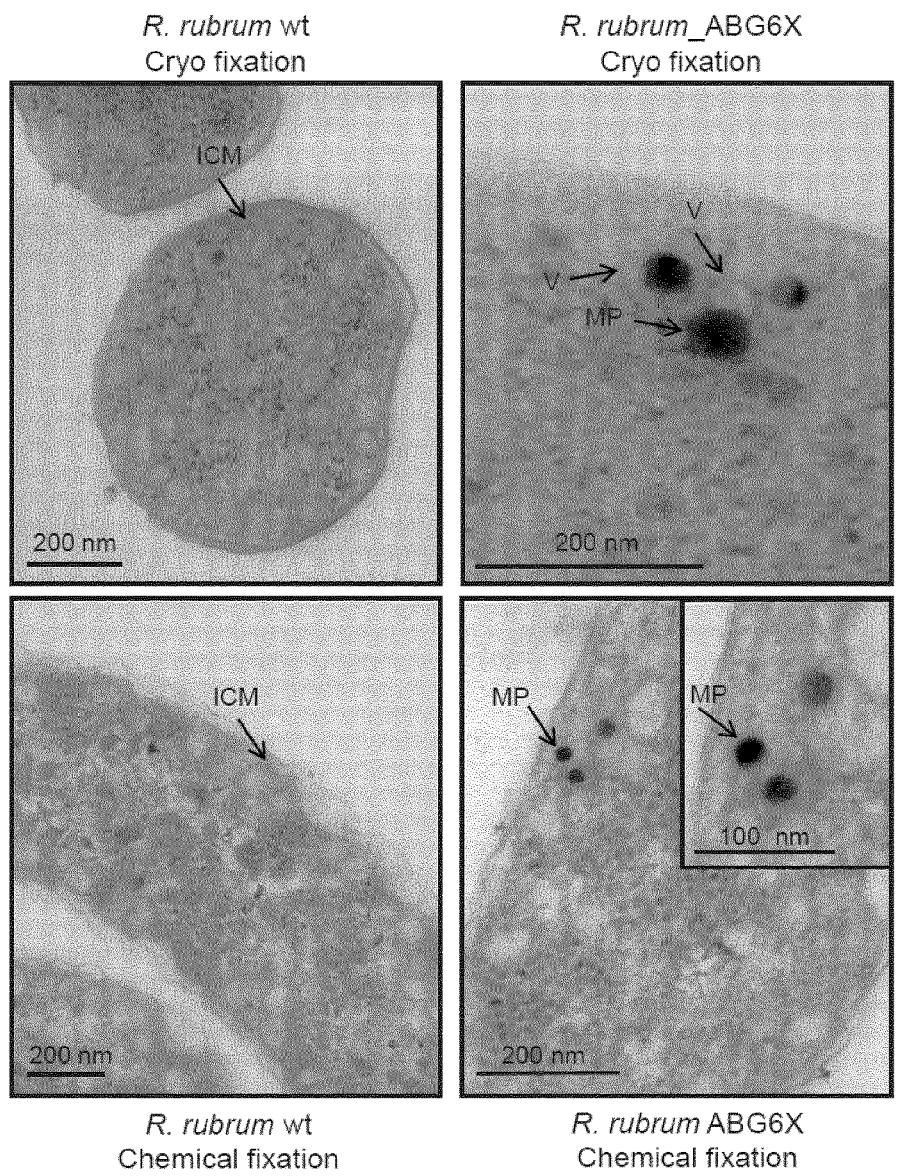

FIG. 11: TEM of cryo-fixed or chemically fixed, thin sectioned *Rhodospirillum rubrum* strains.

Cells were cultivated under photoheterotrophic conditions prior to ultrastructural analysis. ICM sizes of cryo-fixed *R. rubrum* wt (93±34 nm, n=95) and vesicles surrounding immature magnetosomes of cryo-fixed *R. rubrum* ABG6X (66±6 nm, n=6) were measured.

Figure 12:
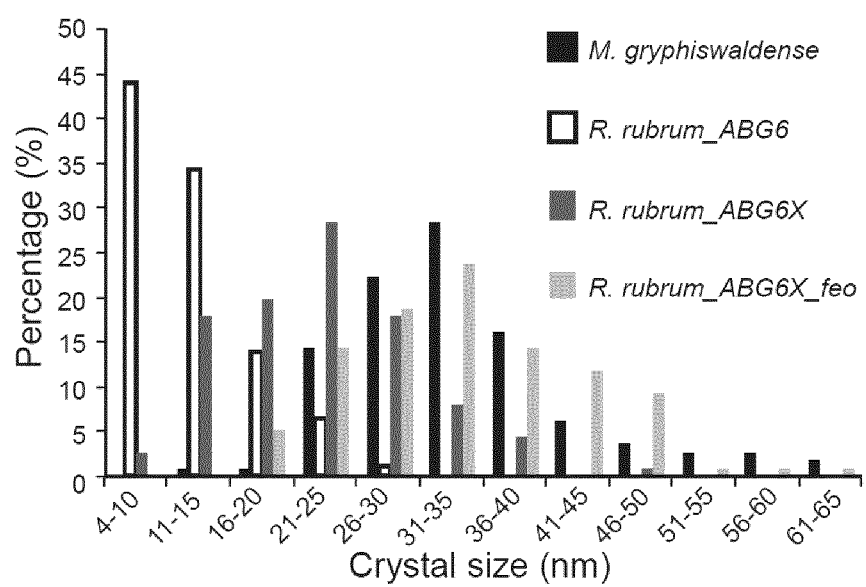

FIG. 12: Size distribution of magnetosome crystals in *Magnetospirillum gryphiswaldense* and different *Rhodospirillum rubrum* strains.

Whereas crystals of *R. rubrum*_ABG6 (n=303) and *R. rubrum*_ABG6X (n=306) were smaller than those of the donor *M. gryphiswaldense* (n=310), crystal sizes of *R. rubrum*_ABG6X_feo (n=301) were significantly larger, approaching those of the donor strain (see also Table 1).

Figure 13:
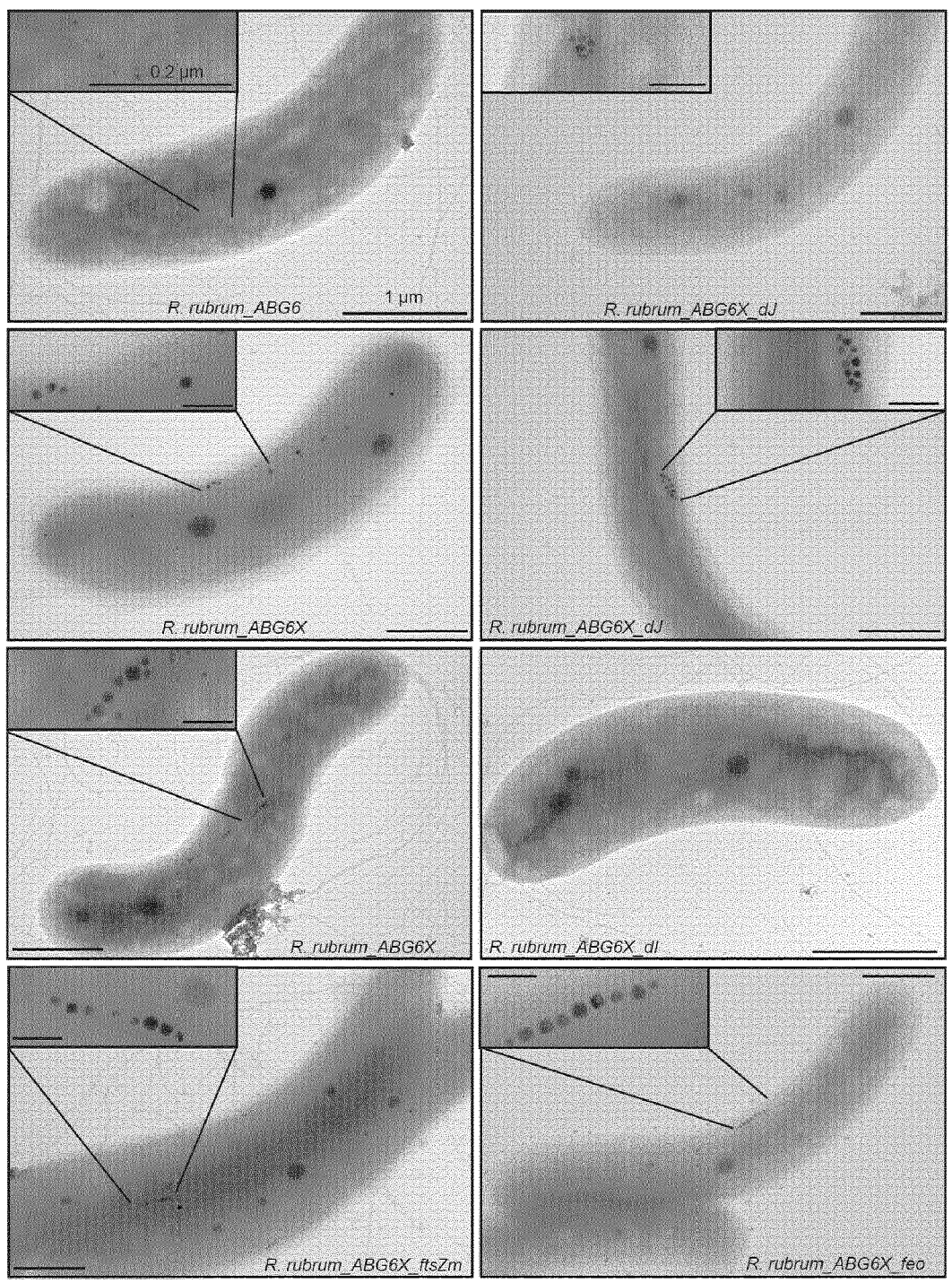

FIG. 13: Transmission electron micrographs of whole cells of different *Rhodospirillum rubrum* strains expressing magnetosome gene clusters. Scale bar: 1 µm, inset: 0.2 µm.

Figure 14:
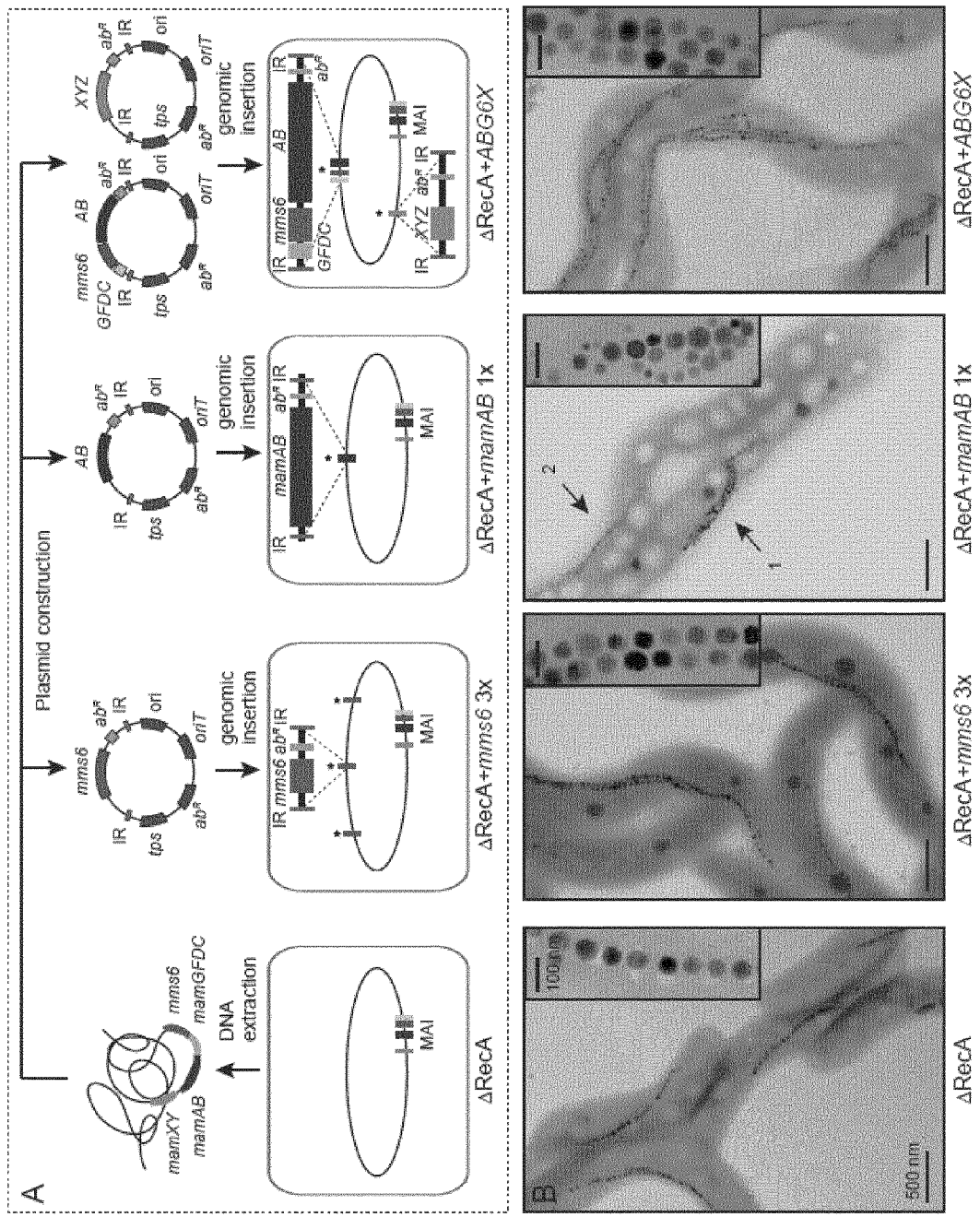

FIG. 14: Overexpression of magnetosome operons in *Magnetospirillum gryphiswaldense*.

Strategy for construction of overexpression strains by amplification of different magnetosome operons (14A). Insertional plasmids were constructed based on genomic DNA from *M. gryphiswaldense* MSR-1. Plasmids contain the magnetosome operons mamAB (blue, AB), mamGFDC (green, GFDC), mms6 (brown) and the mamXY operon lacking ftsZm (pale blue, XYZ). The vector backbone (genes are indicated in red) contains transposase gene (tps), inverted repeats (IR), origin of transfer (oriT), an R6K or p15A origin of replication (ori), and antibiotic resistance cassette ($ab^R$). After conjugative transfer of the plasmids, the transposase recognizes IR sequences and catalyzes chromosomal insertion of the target sequence. Additional copies of respective magnetosome operons in the chromosome (oval shape) are marked with asterisks. (14B) Transmission electron microscopy (TEM) analysis of overexpressing strains. Arrows labeled with 1 and 2 illustrate different magnetosome morphologies identified in strain ΔRecA+mamAB 1×.

Figure 15:
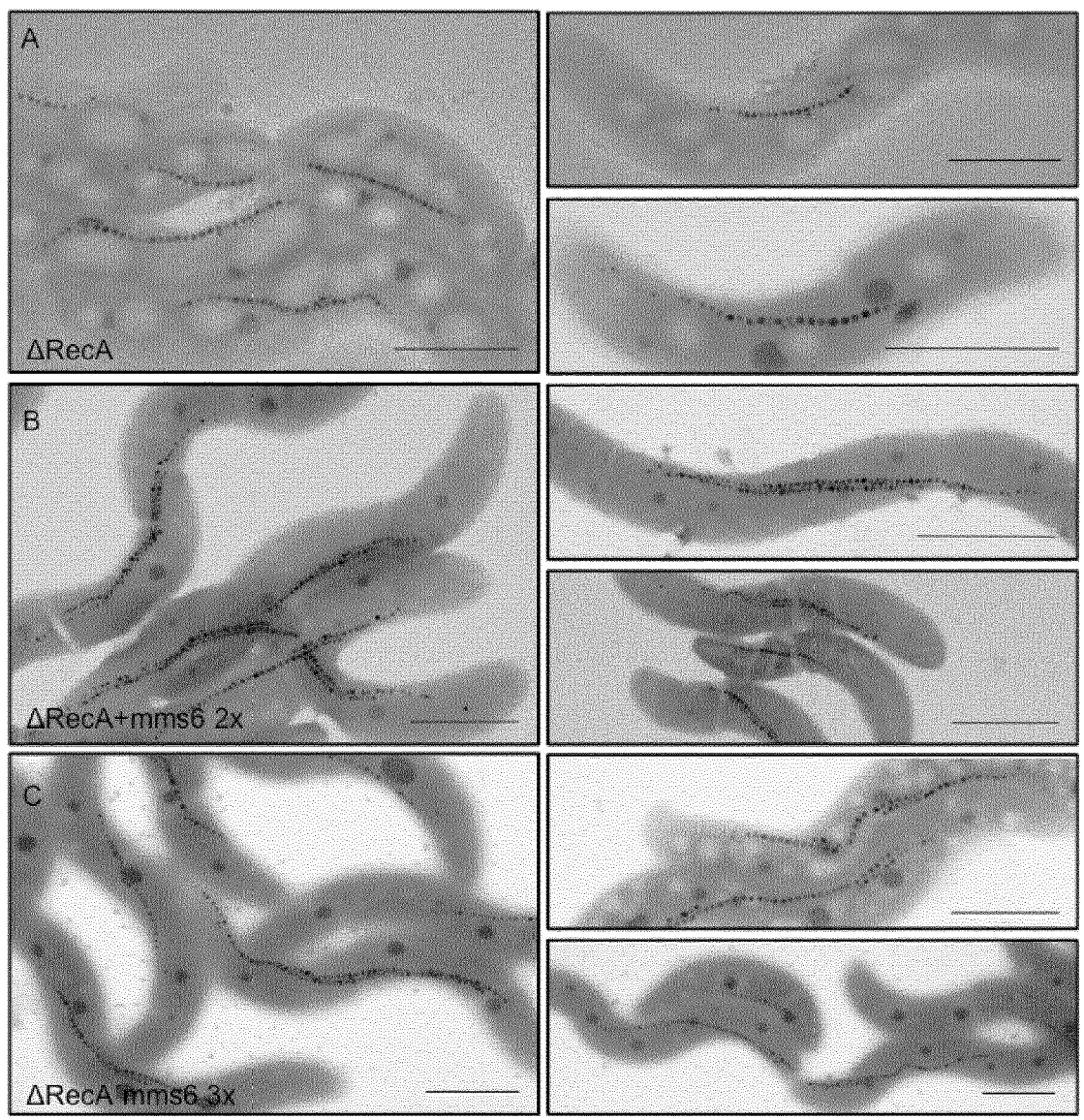

FIG. 15: Enhanced magnetosome formation by overexpression of the mms6 operon in *M. gryphiswaldense* MSR-1.

Representative TEM micrographs of ΔRecA (15A) and overexpressing strains ΔRecA+mms6 2× (15B) (two additional copies of mms6 operon; integrated in genome) and ΔRecA+mms6 3× (15C) (three additional copies of mms6 operon; integrated in genome).

Figure 16:
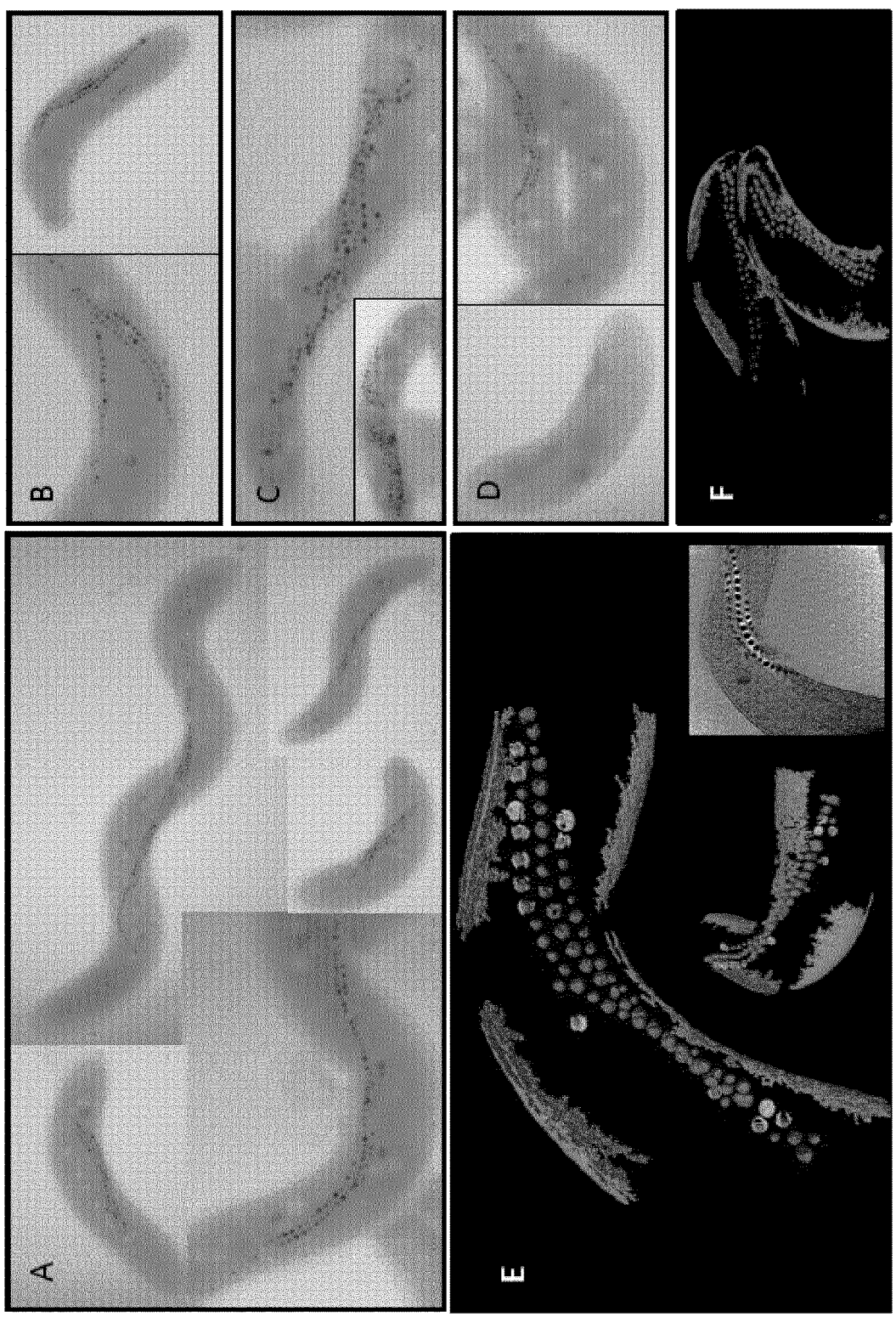

FIG. 16: Characterization of the mutant *M. gryphiswaldense* RecA+ABG6X (mms6, mamGFDC, mamAB and mamXY operons integrated into the genome of ΔRecA.

(16A-D) Representative TEM micrographs of mutant *M. gryphiswaldense* RecA+AB6GX exhibiting enhanced formation of magnetosomes. Mutant cells show various organizations of magnetosomes. (16E-F) Cryo-electron tomography (CET) of mutant cells. Cell membrane (blue); electron dense particles (red); magnetosome vesicles (yellow).

DETAILED DESCRIPTION OF THE INVENTION

The present invention is related to the unexpected finding that gene expression cassettes encoding all relevant genes being sufficient for the biomineralization of bacterial magnetic nanoparticles could be successfully transferred, in their entirety, either to a homologous (i.e., magnetotactic) to a heterologous (i.e., non-magnetotactic) host cell and, upon expression (or overexpression), resulted in the synthesis of functional magnetic nanoparticles.

The present invention will be described in the following with respect to particular embodiments and with reference to certain drawings but the invention is to be understood as not limited thereto but only by the appended claims. The drawings described are only schematic and are to be considered non-limiting.

Where the term "comprising" is used in the present description and claims, it does not exclude other elements or steps. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Where an indefinite or definite article is used when referring to a singular noun e.g. "a", "an" or "the", this includes a plural of that noun unless specifically stated otherwise.

In case, numerical values are indicated in the context of the present invention the skilled person will understand that the technical effect of the feature in question is ensured within an interval of accuracy, which typically encompasses a deviation of the numerical value given of ±10%, and preferably of ±5%.

Furthermore, the terms first, second, third, (a), (b), (c), and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Further definitions of term will be given in the following in the context of which the terms are used. The following terms or definitions are provided solely to aid in the understanding of the invention. These definitions should not be construed to have a scope less than understood by a person of ordinary skill in the art.

In one aspect, the present invention relates to a recombinant host cell, comprising in its genome:
  (i) a gene expression cassette capable of being expressed in the host cell, the gene expression cassette encoding a nucleic acid sequence encompassing at least 80% of the full-length sequence of the mamAB operon of a magnetotactic alpha-proteobacterium;
  (ii) a gene expression cassette capable of being expressed in the host cell, the gene expression cassette encoding a nucleic acid sequence encompassing at least 80% of the full-length sequence of the mamGDFC operon of a magnetotactic alpha-proteobacterium; and
  (iii) a gene expression cassette capable of being expressed in the host cell, the gene expression cassette encoding a nucleic acid sequence encompassing at least 80% of the full-length sequence of the mms6 operon of a magnetotactic alpha-proteobacterium;

wherein the recombinant host cell, upon expression of the gene expression cassettes in their entirety, is capable of producing magnetic nanoparticles.

In preferred embodiments, the recombinant host cell as defined herein further comprises:
  (iv) a gene expression cassette capable of being expressed in the host cell, the gene expression cassette encoding a nucleic acid sequence encompassing at least 80% of the full-length sequence of the mamXY operon of a magnetotactic alpha-proteobacterium; and/or
  (v) a gene expression cassette capable of being expressed in the host cell, the gene expression cassette encoding a nucleic acid sequence encompassing at least 80% of the full-length sequence of the feoAB1 operon of a magnetotactic alpha-proteobacterium.

The term "recombinant host cell", as used herein, refers to any type of host cells comprising in their genome (i.e. the lineom or the chromosome(s) as well as any additional episomal genetic entities such as vectors, plasmids, phagemids, phages, cosmids or artificial chromosomes) the above-referenced "mamAB, mamGDFC, mms6 gene expression cassettes" and optionally also the "mamXY and/or feoAB1 gene expression cassettes", these gene expression cassettes being introduced into the host cells by means of recombinant gene technology (see, e.g., Sambrook, J., and Russel, D. W. (2001) *Molecular cloning: A laboratory manual* (3rd ed.). Cold Spring Harbor, N.Y.: Cold Spring Harbor Laboratory Press), such as transformation, transfection, conjugation or transduction. The term "recombinant host cell", as used herein, also refers to any host cells having endogenous copies of any one or more of the mamAB, mamGDFC, mms6, mamXY, and feoAB1 operons (i.e. homologous host cells) but further comprising (i.e. in addition to the endogenous copies) the recombinant (exogenous) gene expression cassettes as defined herein, thus resulting in overexpression of relevant genetic elements. The gene expression cassettes as defined herein may be maintained in the host cells as part of independent episomal genetic entities or stably integrated in the host cell's genome (i.e. the lineom or the chromosome(s)), with the latter alternative being preferred. Stable integration into the genome may be accomplished by homologous or non-homologous recombination or by transposition, all of them well established in the art (see, e.g., Sambrook, J., and Russel, D. W. (2001) supra).

In preferred embodiments, the recombinant host cells do not have endogenous copies of any one or more of the mamAB, mamGDFC, mms6, mamXY, and feoAB1 operons (that is, any one, any two, any three, any four or all five). In other words, any one or more of gene expression cassettes as defined herein represent heterologous nucleic acid sequences with respect to the host cells employed (i.e., the host cells allow for heterologous gene expression).

In specific embodiments, the recombinant host cells to be employed are prokaryotic cells, such as bacterial or archeal cells, with bacterial cells being preferred. Examples of suitable prokaryotic cells include inter alia *E. coli*, and *Salmonella typhimurium*. In particular embodiments, the bacterial host cells are derived from an alpha-proteobacterium, that is, any species belonging to one of the orders Magnetococcales, Rhodobacterales, Rhodospirillales, Rickettsiales, Sphingomonadales, Caulobacterales, Kordiimondales, Parvularculales, Kiloniellales, and Sneathiellales (Williams, K. P. et al. (2007) *J. Bacteriol.* 189, 4578-4586). In preferred embodiments, the bacterial host cells are derived from the order Rhodospirillales, more preferably from the genus *Rhodospirillum*, and particularly preferably from the species *Rhodospirillum rubrum* (*R. rubrum*).

In a particularly preferred embodiment, the recombinant host cell having stably integrated in its genome the expression cassettes (i) to (v) as described above relates to the host cell being deposited on Nov. 14, 2013 under the Budapest Treaty at the *Deutsche Sammlung von Mikroorganismen and Zellkulturen* (Braunschweig, Germany) having the accession number DSM 28038. The deposited recombinant host cell has the taxonomic designation *Rhodospirillum rubrum* ATCC 11170 (which is herein also referred to as *Rhodospirillum rubrum*_ABG6X_feo).

In further preferred embodiments, the bacterial host cells are derived from the order Magnetococcales (herein also referred to as "magnetotactic alpha-proteobacteria") more preferably from the genus *Magnetospirillum*, and particularly preferably from the species *Magnetospirillum gryphiswaldense* (*M. gryphiswaldense*). Further suitable host cells include *M. magneticum*, *M. magnetotacticum*, MV-1, and MC-1. Such host cells typically comprise endogenous copies of any one or more of the mamAB, mamGDFC, mms6, mamXY, and feoAB1 operons (i.e., the host cells allow for heterologous gene expression, particularly overexpression of the relevant genetic elements).

In specific embodiments, the recombinant host cells to be employed are eukaryotic cells, such as yeast (e.g., *Saccharomyes* spec.), *Pichia pastoris*, and mammalian cells, with the latter ones being preferred. Examples of mammalian cells include mouse, rat, hamster, rabbit, cat, dog, pig, cow, horse, monkey, and particularly preferably human cells.

The term "magnetic nanoparticles", as used herein, denotes any particles having a size in the nanometer scale that exhibits magnetic properties (i.e. that orients in a magnetic field along the magnetic field lines), either being ferromagnetic or being superparamagnetic or exhibiting an intermediate characteristic. The term "nanometer scale", as used herein, refers to a particle diameter of less than 1000 nm (i.e. 1 µm), preferably of less than 500 nm, and particular preferably of less than 100 nm. The "magnetic nanoparticles" may comprise one or more magnetic crystals but are preferably "mono-crystalline". In preferred embodiments, the magnetic nanoparticles further comprise an outer lipid bilayer membrane surrounding the one or more crystals (Grünberg, K. et al. (2004) *Appl. Environ. Microbiol.* 70, 1040-1050): Particles comprising a lipid bilayer membrane are also referred to as "magnetosomes".

The magnetic nanoparticles/magnetosomes being produced by the recombinant host cells employed herein may consist of one or more metal oxides and/or metal sulfides, preferably of the elements in the fourth row of the periodic table (i.e., chrome, manganese, iron, cobalt, and nickel). In particular embodiments, the magnetic nanocrystals are made of a single metal oxide or a single metal sulfide, preferably of an iron oxide such as hematite ($Fe_2O_3$) and magnetite ($Fe_3O_4$) or an iron sulfide such as greigite ($Fe_3S_4$). In particularly preferred embodiments, the magnetic nanoparticles produced according to the present invention consist of magnetite.

The term "capable of producing magnetic nanoparticles", as used herein, denotes the capacity of the recombinant host cells employed to synthesis, upon concomitant expression of the respective "mamAB, mamGDFC, mms6 gene expression cassettes" and optionally also the "mamXY and/or feoAB1 gene expression cassettes", functional magnetic nanoparticles as described above.

The term "gene expression cassette", as used herein, typically denotes a nucleic acid sequence comprising sequence elements which contain information regarding to transcriptional and/or translational regulation, such regulatory sequences being "operably linked" to the nucleotide sequence encoding one or more polypeptides to be expressed (i.e. to be synthesized starting from the gene sequence). An operable linkage is a linkage in which the regulatory sequence elements and the sequence to be expressed (and/or the sequences to be expressed among each other) are connected in a way that enables gene expression. The precise nature of the regulatory regions necessary for gene expression may vary among species, but in general these regions comprise a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell. In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

The term "operon", as used herein, refers to a functional genetic unit of two or more genes, which are transcribed together into a single mRNA and are typically under the control of common regulatory sequence elements (i.e. promoters, terminators, and the like).

The mamAB, mamGDFC, mamXY, mms6 and feoAB1 operons encoded by the respective gene expression cassettes as described herein are derived from a "magnetotactic alpha-proteobacterium" (cf. the definition herein above), more preferably from the genus *Magnetospirillum*, and particularly preferably from the species *M. gryphiswaldense*. The exact nucleotide sequences of all these operons are known in the art and can be accessed under GenBank accession number AM085146.1 (relating to the complete 130 kb sequence of the magnetosome island of *M. gryphiswaldense* MSR-1; cf. also Ullrich, S. et al. (2005) *J. Bacteriol.* 187, 7176-7184). In specific embodiments, the mamAB, mamGDFC, mamXY, mms6 and feoAB1 operons encoded by the respective gene expression cassettes present in a particular host cell are all derived from the same magnetotactic alpha-proteobacterium, for example from *M. gryphiswaldense*. In other specific embodiments, the operons encoded by the respective gene expression cassettes present in a particular host cell are derived from two or more different magnetotactic alpha-proteobacteria, for example mamAB and mamGDFC from *M. gryphiswaldense*, and the remaining operons from *M. magnetotacticum*.

Each of the gene expression cassettes (that is, independently from each other) introduced into the genome of the recombinant host cell encode nucleic acid sequences encompassing at least 80% of the full-length sequence of the respective operon sequences. Sequence identity is calculated over the entire length of the full-length sequence of the respective operon, that is, the sequence present in each of the gene expression cassettes may be terminally truncated (either 5'-terminally or 3'-terminally or 5'- and 3'-terminally) and/or may include one or more deletions or substitutions of internal sequences (e.g., the deletion and/or replacement of one or more genes comprised in a given operon).

In preferred embodiments, one or more of the gene expression cassettes encode nucleic acid sequences encompassing at least 85%, at least 90% or at least 95% of the full-length sequence of the respective operon sequences. In particular embodiments, the one or more of the gene expression cassettes encode nucleic acid sequences encompassing the full-length sequence of the respective operon sequences. In specific embodiments, one or more of the gene expression cassettes encode nucleic acid sequences encompassing at least 50%, at least 60% or at least 70% of the full-length sequence of the respective operon sequences. Sequence identity may be determined based on the nucleotide sequence or on the amino acid sequence. Various software tools and algorithms for determining nucleotide sequence and/or amino acid sequence identity are well established in the art (e.g., BLAST, FASTA, ClustalW, UGENE).

For example, in one embodiment, the present invention relates to a recombinant host cell, comprising in its genome: a gene expression cassette capable of being expressed in the host cell, the gene expression cassette encoding a nucleic acid sequence encompassing at least 80% of the full-length sequence of the mamAB operon of *M. gryphiswaldense*; a gene expression cassette capable of being expressed in the host cell, the gene expression cassette encoding a nucleic acid sequence encompassing at least 90% of the full-length sequence of the mamGDFC operon of *M. gryphiswaldense*; and a gene expression cassette capable of being expressed in the host cell, the gene expression cassette encoding a nucleic acid sequence encompassing the full-length sequence of the mms6 operon of *M. gryphiswaldense*. In another, embodiment, the present invention relates to a recombinant host cell, comprising in its genome: a gene expression cassette capable of being expressed in the host cell, the gene expression cassette encoding a nucleic acid sequence encompassing at least 50% of the full-length sequence of the mamAB operon of *M. gryphiswaldense*; a gene expression cassette capable of being expressed in the host cell, the gene expression cassette encoding a nucleic acid sequence encompassing at least 80% of the full-length sequence of the mamGDFC operon of *M. gryphiswaldense*; and a gene expression cassette capable of being expressed in the host cell, the gene expression cassette encoding a nucleic acid sequence encompassing at least 90% of the full-length sequence of the mms6 operon of *M. gryphiswaldense*.

In another embodiment, the present invention relates to a recombinant host cell, comprising in its genome:
(i) a gene expression cassette capable of being expressed in the host cell, the gene expression cassette encoding a nucleic acid sequence encompassing at least 80% of the full-length sequence of the mamAB operon of a magnetotactic alpha-proteobacterium;
(ii) a gene expression cassette capable of being expressed in the host cell, the gene expression cassette encoding a nucleic acid sequence encompassing at least 80% of the full-length sequence of the mamGDFC operon of a magnetotactic alpha-proteobacterium;
(iii) a gene expression cassette capable of being expressed in the host cell, the gene expression cassette encoding a nucleic acid sequence encompassing at least 80% of the full-length sequence of the mms6 operon of a magnetotactic alpha-proteobacterium; and
(iv) a gene expression cassette capable of being expressed in the host cell, the gene expression cassette encoding a nucleic acid sequence encompassing at least 80% of the full-length sequence of the mamXY operon of a magnetotactic alpha-proteobacterium;
wherein the recombinant host cell, upon expression of the gene expression cassettes in their entirety, is capable of producing magnetic nanoparticles.

In another embodiment, the present invention relates to a recombinant host cell, comprising in its genome:
(i) a gene expression cassette capable of being expressed in the host cell, the gene expression cassette encoding a nucleic acid sequence encompassing at least 80% of the full-length sequence of the mamAB operon of a magnetotactic alpha-proteobacterium;
(ii) a gene expression cassette capable of being expressed in the host cell, the gene expression cassette encoding a nucleic acid sequence encompassing at least 80% of the full-length sequence of the mamGDFC operon of a magnetotactic alpha-proteobacterium;
(iii) a gene expression cassette capable of being expressed in the host cell, the gene expression cassette encoding a nucleic acid sequence encompassing at least 80% of the full-length sequence of the mms6 operon of a magnetotactic alpha-proteobacterium; and
(v) a gene expression cassette capable of being expressed in the host cell, the gene expression cassette encoding a nucleic acid sequence encompassing at least 80% of the full-length sequence of the feoAB1 operon of a magnetotactic alpha-proteobacterium;
wherein the recombinant host cell, upon expression of the gene expression cassettes in their entirety, is capable of producing magnetic nanoparticles.

In a preferred embodiment, the present invention relates to a recombinant host cell, comprising in its genome:
(i) a gene expression cassette capable of being expressed in the host cell, the gene expression cassette encoding a nucleic acid sequence encompassing at least 80% of the full-length sequence of the mamAB operon of a magnetotactic alpha-proteobacterium;
(ii) a gene expression cassette capable of being expressed in the host cell, the gene expression cassette encoding a nucleic acid sequence encompassing at least 80% of the full-length sequence of the mamGDFC operon of a magnetotactic alpha-proteobacterium;
(iii) a gene expression cassette capable of being expressed in the host cell, the gene expression cassette encoding a nucleic acid sequence encompassing at least 80% of the full-length sequence of the mms6 operon of a magnetotactic alpha-proteobacterium;
(iv) a gene expression cassette capable of being expressed in the host cell, the gene expression cassette encoding a nucleic acid sequence encompassing at least 80% of the full-length sequence of the mamXY operon of a magnetotactic alpha-proteobacterium; and
(v) a gene expression cassette capable of being expressed in the host cell, the gene expression cassette encoding a nucleic acid sequence encompassing at least 80% of the full-length sequence of the feoAB1 operon of a magnetotactic alpha-proteobacterium;
wherein the recombinant host cell, upon expression of the gene expression cassettes in their entirety, is capable of producing magnetic nanoparticles. In a particularly preferred embodiment, the gene expression cassettes (i) to (v) all encode nucleic acid sequences encompassing the full-length sequences of the respective operons.

The gene expression cassettes (i) to (v) as described above may be provided independently or any two, any three, any four or all five gene expression cassettes may be provided in combination (e.g. as part of a common genetic vector or transposon). For example, the gene expression cassettes (i), (ii), and (iii) may be provided in combination.

Preferably, the combination of the gene expression cassettes (i), (ii), and (iii) has a nucleic acid sequence as shown in SEQ ID NO. 35. Also preferably, gene expression cassette (iv) has a nucleic acid sequence as shown in SEQ ID NO. 36 and/or gene expression cassette (v) has a nucleic acid sequence as shown in SEQ ID NO. 37.

The total length of the gene expression cassettes (i) to (iii), and optionally also (iv) and/or (v) comprised in the genome of the recombinant host cell (each being present in single copy) is less than 100 kb, preferably less than 80 kb or less than 60 kb, and particularly preferably less than 40 kb or less than 35 kb.

The term "gene expression cassette capable of being expressed in the host cell", as used herein, denotes that the operon encoded by the gene expression cassette is under the control of regulatory elements being functional in the host cell employed. In preferred embodiments, gene expression of the respective operons is under the control of the endogenous regulatory elements, that is, the homologous regulatory elements naturally occurring in the particular organism from which the respective operon(s) is/are derived. For example, if the respective operons are derived from M. gryphiswaldense, the corresponding regulatory elements derived from the same organism may be employed. Typically, the gene expression cassettes may then comprise a nucleic acid sequence encompassing 100-800, preferably 200-600 nucleotides upstream (i.e., 5') of the respective operon and 100-800, preferably 200-600 nucleotides downstream (i.e., 3') of the respective operon. In other embodiments, the regulatory elements comprise non-endogenous sequences, that is exogenous inducible or constitutive promoters (e.g., tet, lac, CMV promoters) and terminators.

In further specific embodiments, the recombinant host cell comprises two or more copies of any one or more of the gene expression cassettes. Preferably, the copy numbers of all gene expression cassettes being present in a recombinant host cell are identical, for example two copies. In other embodiments, the copy numbers of the respective gene expression cassettes are different.

In a further aspect, the present invention relates to a method for the production of a recombinant host cell as defined herein, the method comprising the transfer of the gene expression cassettes into the host cell by means of genetic transposition, and in particular comprising a modular transfer of the gene expression cassettes.

The gene expression cassettes (i) to (v) as described above may be introduced in to the recombinant host cells independently or any two, any three, any four or all five gene expression cassettes may be introduced concomitantly on a common genetic vector or transposon.

In yet another aspect, the present invention relates to the use of a recombinant host cell as defined herein for the biotechnological production of magnetic nanoparticles.

In yet another aspect, the present invention relates to the use of a recombinant host cell as defined herein for the in vivo synthesis of magnetic nanoparticles for application in magnetogenetics or biomedical imaging.

The invention is further described by the figures and the following examples, which are solely for the purpose of illustrating specific embodiments of this invention, and are not to be construed as limiting the claimed subject matter in any way.

Examples

1. Materials and Methods 1.1 Bacterial Strains

Bacterial strains are shown in Table 4. *E. coli* strains were cultivated as previously described (Sambrook, J. & Russell, D. (2001) *Molecular cloning: a laboratory manual*. Vol. 3, Cold Spring Harbor Laboratory Press). 1 mM DL-α,ε-diaminopimelic was added for growth of BW29427 and WM3064.

Liquid cultures and single colonies of *Magnetospirillum gryphiswaldense* were cultivated in FSM medium or on agar plates (1.5% agar) incubated at 30° C. under microaerobic (1% $O_2$) conditions (Heyen, U. and Schüler, D. (2003) *Appl. Microbiol. Biotechnol.* 61, 536-544; Kolinko, I. et al. (2011) *J. Bacteriol.* 193, 5328-5334)

Cultures of *Rhodospirillum rubrum* strains were cultivated chemoheterotrophically (ATCC medium 112) with free gas exchange in the dark, microaerobically in M2SF medium (Ghosh, R. et al. (1994) *Appl. Environ. Microbiol.* 60, 1698-1700), or photoheterotrophically in Sistrom A medium (Sistrom, W. R. (1962) *J. Gen. Microbiol.* 28, 607-616) supplemented with Fe(III) citrate or Fe(II) sulfate at 18° C., 23° C. or 30° C. (10, 400, 1000, 9000 lux). The 16S rRNA similarity to *M. gryphiswaldense* is shown in Table 2.

1.2 Plasmid Construction and Conjugative Transfer

Plasmids and oligonucleotides used are shown in Table 4 and Table 5, respectively. Red/ET recombination was performed as previously described (Wang, J. et al. (2006) *Mol. Biotechnol.* 32, 43-53 (2006); Fu, J. et al. (2008) *Nucl. Acids Res.* 36, e113) in order to construct expression cassettes harboring a mariner transposon vector backbone and magnetosome operons obtained from a BAC sequence pSSK18 (Schübbe, S. et al. (2003) *J. Bacteriol.* 185, 5779-5790) (mamAB) and *M. gryphiswaldense* genomic DNA (mamGFDC, mms6, mamXY). Briefly, a cloning cassette was amplified by polymerase chain reaction (PCR) and transferred into electro-competent *E. coli* cells (DH10b) expressing phage-derived recombinases from a circular plasmid (pSC101-PBad-gbaA). After transfer of the cassette, recombination between homologous regions on the linear fragment and the plasmid occurred. For introducing of the magnetosome gene operons (cf. FIG. 4), triple recombination was used with cotransforming of two linear fragments, which recombined with a circular plasmid (Fu; j. et al. (2008) *Nucleic Acids Res.* 36, e113). Recombinants harboring the correct plasmids were selected by restriction analysis.

For construction of plasmids harboring fusion proteins, the mamDC promoter (XbaI, BamHI restriction sites added), mamGFDC operon or mamJ gene (NdeI, KpnI) and egfp (KpnI, EcoRI) were cloned into a pBAM1 plasmid (Martinez-Garcia, E. et al. (2011) *BMC Microbiol.* 11, 38) with a tetracycline resistance cassette (exchange of $km^R$ against $tc^R$ with SanDI and AatII). The replicative plasmid pFM211 (obtained from Dr. Frank Müller, Ludwig-Maximilians-Universität München, Germany, unpublished) harboring ftsZm with a mCherry fusion under control of an inducible lac promoter was recombined with pBAM1 to construct pBAM-ftsZm_mcherry. The resident $km^R$ exchanged by $tc^R$ using ET-recombination. For construction of pBAM_feoAB1, a fragment with $P_{mamH}$ and feoAB1 was amplified with PCR from pRU1feoAB (XbaI, EcoRI) and cloned into Tet-pBAM1. Conjugation experiments of *M. gryphiswaldense* deletion mutants (Lohsse, A. et al. (2011) *PLoS One* 6, e25561) were performed as described (Kolinko, I. et al. (2011) supra).

For conjugation of *R. rubrum*, cultures were incubated in ATCC 112 medium. Approximately $2*10^9$ cells were mixed with $1*10^9$ *E. coli* cells, spotted on ATCC agar medium and incubated for 15 h. Cells were flushed from the plates and incubated on ATCC 112 agar medium supplemented with appropriate antibiotics for 7-10 days (Tc (tetracycline): 10 µg/ml, Km (kanamycin: 20 µg/ml, Gm (gentamicin): 10 µg/ml). Sequential transfer of the plasmids resulted in $10^{-6}$-$10^{-8}$ antibiotic-resistant transconjugants per recipient, respectively. Two clones from each conjugation experiments were chosen for further analyses.

Transposition of the cassettes resulted in single-copy integration into the genome and stable maintenance for at least 40 generations in the absence of selection characterized transconjugants were indistinguishable from WT with respect to motility, cell morphology or growth during photoheterotrophic cultivation (FIG. 8).

1.3 Analytical Methods

Optical density of *M. gryphiswaldense* cultures was measured at 565 nm (Schüler, D. et al. (1995) *FEMS Microbiol. Ecol.* 132, 139-145). Optical density of *R. rubrum* cultures was measured at 660 nm (minimal absorption of bacteriochlorophyll a (Bchl a)) and 880 nm (maximal Bchl a absorption) (Ghosh, R. et al. (1994) supra). The ratio of 880/660 nm was used to determine yields of chromatophores within intact cells. Furthermore, Bchl a was extracted from cultures with methanol and absorption spectra were measured in an Ultrospec 3000 photometer (GE Healthcare). The spectra of photoheterotrophically cultivated *R. rubrum*_ABG6X cells were indistinguishable from those of the wild-type (FIG. 7).

Intracellular iron concentrations were determined after incubation under anaerobic conditions using a modified version of the ferrozine assay (Viollier, E. et al. (2000) *Appl. Geochemistry* 15, 785-790). In brief, 4 ml cultures were centrifuged for 1 min at 11.000 rpm and resuspended in 90 µl $HNO_3$ (65%) for 3 h at 99 C. The average magnetic orientation of cell suspensions (magnetic response) was assayed with a light scattering assay as previously described (Schüler, D. et al. (1995) supra). Briefly, cells were aligned at different angles to a light beam by application of an external magnetic field. Crystal size (n=120) and vesicle measurements (n=100) were performed with ImageJ software.

1.4 Sequencing

Genomic sequencing of strain *R. rubrum*_ABG6X was performed via Next-Generation Sequencing by using the SOLID EZ Bead System (Life Technologies GmbH, Darmstadt, Germany) according to the manufacturer's protocol. No mutations were detected, except for a deletion (aa 169-247) within the hypervariable non-essential CAR domain of mamJ.

1.5 Microscopy

For transmission electron microscopy (TEM), cells and isolated magnetosomes were absorbed on carbon-coated copper grids. Purified magnetosomes were stained with 1% phosphotungstic acid (PTA) or 2% Uranyl acetate (UrAc). Samples were viewed and recorded with a Morgagni 268 microscope. Crystal sizes and Vesicle sizes were determined using ImageJ software.

Chemical fixation, high pressure freezing and thin sectioning of cells was performed as previously described (Jogler, C. et al. (2011) *Proc. Natl. Acad. Sci. USA* 108, 1134-1139). In brief, for chemical fixation, cells were incubated in 2.5% glutardialdehyde containing fixative buffer (75 mM sodium cacodylate, 2 mM $MgCl_2$, pH 7.0), for 1 h at room temperature. Afterward, samples were rinsed several times in fixative buffer and post-fixed at room temperature for 1 h with 1% osmium tetroxide in fixative buffer. After two washing steps in water, the cells were stained enbloc for 30 min with 1% uranyl acetate in 20% acetone. Dehydration was performed with a graded acetone series. Samples were then in-filtrated and embedded in Spurr's low-viscosity resin. For high-pressure freezing, aluminum platelets were filled with concentrated cell suspensions and the cells immobilized by high-pressure freezing (Leica; HPM100). Freeze substitution was performed in acetone with 2% osmium tetroxide and 0.2% uranyl acetate, including 5% water. After embedding the samples in Epon, ultrathin sections were cut with a diamond knife and mounted onto uncoated copper grids. The sections were post-stained with aqueous lead citrate (100 mM, pH 13.0. Micrographs were taken with an EM 912 electron microscope (Zeiss) equipped with an integrated OMEGA energy filter operated at 80 kV in the zero loss mode). Vesicle sizes were determined using ImageJ software.

High-resolution TEM (HRTEM) was performed using a JEOL 3010 microscope, operated at 297 kV and equipped with a Gatan Imaging Filter (GIF) for the acquisition of electron energy-loss spectra and energy-filtered compositional maps. For TEM data processing and interpretation the DigitalMicrograph and SingleCrystal software were used (Uebe, R. et al. (2011) *Mol. Microbiol.* 82, 818-835).

Cryo-electron-tomography was performed as previously described (Katzmann, E. et al. (2011) *Mol. Microbiol.* 82, 1316-1329). In brief, a FEI Tecnai F30 Polara transmission electron microscope was used. All data collection was performed at 300 kV, with the energy filter operated in the zero-loss mode (slit width of 20 eV). Tilt series were acquired using Serial EM and FEI software. Quantifoil copper grids (Quantifoil Micro Tools GmbH, Jena) were prepared by placing a droplet of 10-15 nm colloidal gold clusters (Sigma) on each grid for subsequent alignment purposes. Additionally a droplet of culture was added onto the prepared grid, and after blotting embedded in vitreous ice by plunge freezing into liquid ethane (temperature $-170°$ C.). The specimen was tilted typically about one axis with $1.5°$ increments over a total angular range of $+/-65°$ to minimize the electron dose. The total dose accumulated during the tilt series was kept below 200 e/Å$^2$. To account for the increased specimen thickness at high tilt angles, the exposure time was multiplied by a factor of $1/\cos \alpha$. The pixel size in unbinned images was 0.805 at a magnification of 27500 and 1.10 at a magnification of 41000.

Fluorescence microscopy was performed with an Olympus BX81 microscope equipped with a Hamamatsu Orca-ER camera. Exposure time of 0.12-0.25 s was used. Image scaling and cropping was performed with Photoshop 9.0 software.

1.6 Isolation of Magnetic Particles, Electrophoresis and Immunochemical Detection Unless described otherwise, expression of magnetic particles in *R. rubrum* was performed under photoheterotrophic conditions at 23° C. and a light intensity of 1000 lux. Cells were harvested, washed and resuspended. Cell suspensions were lysed by sonication and cellular debris was removed by low-speed centrifugation.

Crystals were isolated from sonification-disrupted *R. rubrum*_ABG6X feo cells using magnetic separation (Uebe, R. et al. (2011) *Mol. Microbiol.* 82, 818-835). For TEM analysis, whole cells were directly absorbed on carbon-coated copper grids. Alternatively, cells were chemically fixed or high pressure frozen and thin sectioned prior to ultrastructural analysis (Jogler, C. et al. (2009) *Environ. Microbiol.* 11, 1267-1277). Electron dense particles of *R. rubrum* WT, *R. rubrum*_ABG, *R. rubrum*_ABG6 and *R. rubrum*_ABG6X were analyzed by HRTEM (Uebe, R. et al. (2011) *Mol. Microbiol.* 82, 818-835). Cryo-electron tomography was performed with cultures of *R. rubrum*_ABG6X or isolated magnetic particles from *R. rubrum*_ABG6X_feo as previously described (Katzmann, E. et al. (2011) supra). Magnetic particles were stained with 1% phosphotungstic acid (PTA) or 2% uranyl acetate (UrAc) to visualize organic material surrounding magnetic particles. Proteins of the organic layer were solubilized as previously described (Grünberg, K. et al. (2004) *Appl. Environ. Microbiol.* 70, 1040-1050; Lang, C. and Schüler, D. (2008) *Appl. Environ. Microbiol.* 74, 4944-4953) and analyzed by Western blotting and LC tandem MS.

Polyacrylamide gels were prepared according to the procedure of Laemmli (Laemmli, U. K. (1970) *Nature* 227, 680-685). Protein samples from different cellular fractions were resuspended in electrophoresis sample buffer and denatured at 98° C. for 5 min (Uebe, R. et al. (2011) supra). 10 µg of protein extracts were separated on a 15% SDS-polyacrylamide gel. Protein bands were visualized by Coomassie brilliant blue staining. Western blot analysis for detection of MamC was performed as previously described (Lang, C. and Schüler, D. (2008) supra).

1.7 Mass Spectrometric Analysis

For MS analyses, 25 µg solubilized proteins were tryptically in-gel digested as described previously (Klein, A. et al. (2012) *J. Cell. Biol.* 199, 599-611). For protein identification and quantification, the tryptic fragments were separated on a C18 reversed-phase column with a linear acetonitrile gradient and analyzed by nano-electrospray ionization-LC tandem MS (ESI-LC-MS/MS), recorded on an Orbitrap mass spectrometer. Resulting spectra were analyzed via Mascot™ software using the National Center for Biotechnology Information (NCBI) nr Protein Database and a database from *M. gryphiswaldense* (Richter, M. et al. (2007) *J. Bacteriol.* 189, 4899-4910).

2. Heterologous Production of Magnetosomes in *Rhodospirillum rubrum*

In the alpha-proteobacterium *Magnetospirillum gryphiswaldense* and related magnetotactic bacteria, biogenesis of functional magnetosomes is highly complex and involves the invagination of magnetosome vesicles from the cytoplasmic membrane, the magnetosomal uptake of iron and the crystallization of magnetite particles, as well as their assembly into chains along a dedicated cytoskeletal structure (Komeili, A. et al. (2006) *Science* 311, 242-245; Katzmann, E. et al. (2010) *Mol. Microbiol.* 77, 208-224). Recently, genes controlling magnetosome synthesis within several clusters of a larger (115 kb) genomic magnetosome island (MAI) were discovered, which are interspersed by transposases and genes of unknown function (Jogler, C. et al. (2009) supra; Jogler, C. et al. (2011), supra; Lefevre, C. T. et al. (2013) *Environ. Microbiol.*, April 1, doi: 10.1111/1462-2920.12128). Whereas the smaller mamGFDC (2.1 kb), mms6 (3.6 kb) and mamXY operons (5.1 kb) have accessory functions in biomineralization of properly sized and shaped crystals, the large mamAB operon (16.4 kb) encodes proteins essential for iron transport, magnetosome membrane assembly/formation, and crystallization of magnetosome particles as well as their assembly and intracellular positioning.

Using recombinant engineering based on phage driven homologous recombination (Zhang, Y. et al. (2000); *Nat Biotechnol* 18, 1314-1317; Fu, J. et al. (2008) *Nucl. Acids Res.* 36, e113), several compact modular expression cassettes were put together comprising all 29 genes (about 26 kb in total) of the four major/relevant operons in various combinations, but lacking the tubulin-like ftsZm. This gene was omitted from its native mamXY operon because of its observed interference with cell division during cloning. Regions 200-400 bp upstream of all operons were retained to ensure transcription from their native promoters (Schübbe, S. et al. (2006) *Appl Environ Microbiol* 72, 5757-5765) (FIG. 4).

Since in initial attempts conjugational transfer of multi-copy plasmids harboring large parts of the mamAB operon resulted in lack of functional expression and genetic instability due to extensive rearrangements and deletions (data now shown), transposition cassettes comprising the MycoMar transposase gene (tps) or Tn5 transposase gene, two corresponding inverted repeats, the origin of transfer oriT, and an antibiotic resistance gene were designed to enable transfer and chromosomal integration of the gene clusters in single copy. Chromosomal re-integration of all cassettes into different non-magnetic, single-gene as well as large operon deletion strains of *M. gryphiswaldense* resulted in stable and complete restoration of magnetosome biomineralization (FIG. 5).

Chromosomal re-integration of all cassettes into different non-magnetic single-gene and operon deletion strains of *M. gryphiswaldense* resulted in stable wild-type like restoration of magnetosome biomineralization, indicating that transferred operons maintained functionality upon cloning and transfer (FIG. 5).

Figure 1:
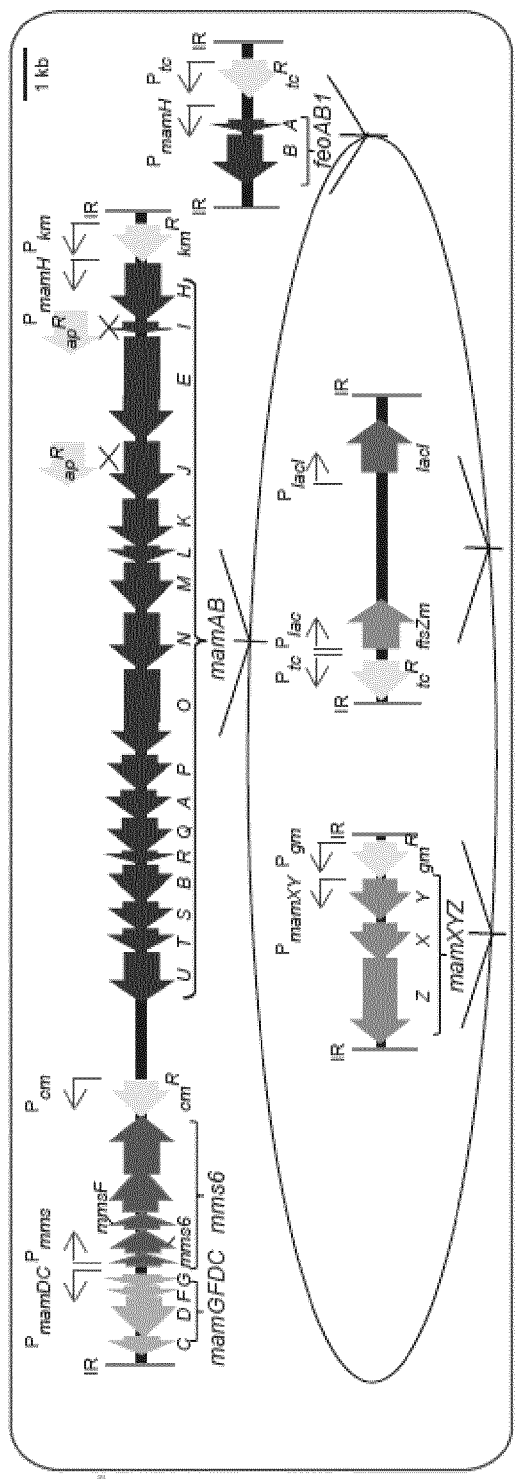
FIG. 1: Schematic representation of *Magnetospirillum gryphiswaldense* gene clusters that were transferred to the chromosome of *Rhodospirillum rubrum*.

Next, the transfer of expression cassettes to a foreign non-magnetic organism was analyzed. The photosynthetic alpha-proteobacterium *Rhodospirillum rubrum* was chosen as potential expression host due to the phylogenetic relationship between the Rhodospirillaceae and magnetotactic bacteria, which except magnetosome and photosynthetic gene functions, shares a high proportion of conserved genes (Richter, M. et al. (2007) *J Bacteriol* 189, 4899-4910) (FIG. 1).

Neither conjugational transfer of the mamAB operon alone (pTps_AB), which was reported to be sufficient for weak magnetosome biomineralization in its native host, nor in combination with the accessory mamGFDC genes (pTps_ABG) had any detectable phenotypic effect on cells with respect to iron content and magnetic response $C_{mag}$ (cf. TABLE 1). However, although no magnetic response after insertion of pTps_ABG6 (mamAB+mamGFDC+mms6 operons) could be detected, the cellular iron content of *R. rubrum*_ABG6 was increased 2.4-fold compared to the untransformed (i.e., wild-type) *R. rubrum*. Transmission electron micrography revealed the presence of irregularly shaped, flake-like electron dense particles (~12 nm) traversing the cell in a chain-like structure (FIG. 2a ii), which were identified as poorly crystalline hematite ($Fe_2O_3$) by analysis of lattice spacings in high-resolution TEM images (cf. FIG. 6), much as in the hematite particles previously identified in *M. gryphiswaldense* mutants affected in crystal formation (Uebe, R. et al. (2011) *Mol. Microbiol.* 82, 818-835)

Next, in order to further enhance biomineralization pTps_XY was transferred into *R. rubrum*_ABG6, resulting in strain *R. rubrum*_ABG6X harboring, in addition to mamAB, mamGFDC, and mms6, also mamXYZ, thus encompassing all 29 relevant MAI (magnetosome island) genes, except for frftsZm. Intriguingly, cells of this strain exhibited a magnetic response in the classical light scattering assay for *Magnetospirillum* ($C_{mag}$≈0.3) (Schüler, D. et al. (1995) supra) and were "magnetotactic" (TABLE 1), i.e., within several hours accumulated as a visible pellet near the pole of a permanent magnet at the edge of a culture flask (FIG. 2b). TEM revealed the presence of cuboidal electron dense particles with an average size of 25 nm, which were aligned in short, fragmented chains loosely dispersed within the cells (FIG. 2a iii). Electron diffraction identified the electron dense particles as single or twinned crystals of magnetite ($Fe_3O_4$) (FIG. 11). Despite their smaller sizes (average: 24 nm) the particles strongly resembled the magnetosomes of the donor strain with respect to their projected outlines and thickness contrast, suggestive of cubooctahedral or octahedral crystal morphologies (FIG. 2d).

Separate insertion of the ftsZm gene, which was first omitted from pTps_XY because of its observed interference with cell division during cloning, under control of the inducible lac promoter did not further increase the intracellular iron content and number and size of the crystals compared to strains *R. rubrum*_ABG6X (FIG. 1a iv; TABLE 1), despite of an increased $C_{mag}$, possibly due to subtle effects on cell morphology. Although it was implicated in biomineralization in *M. gryphiswaldense* (Ding, Y. et al. (2010) *J. Bacteriol.* 192, 1097-1105), the tubulin-like FtsZm does not appear to have a crucial role for biomineralization in *R. rubrum*.

Subsequently, the relationship between magnetite formation and growth conditions of the metabolically versatile *R. rubrum* was investigated. During both photoheterotrophic and microoxic chemotrophic growth in the dark a magnetic response of strain *R. rubrum*_ABG6X was detectable. No magnetic response was detectable under aerobic conditions (FIGS. 7 and 8). In contrast to extracellular iron speciation (ferric vs. ferrous iron at various concentrations), which did not affect particles formation, biomineralization was completely inhibited by higher temperatures (>30° C.) under microoxic conditions, which was also observed after serial passages under phototrophic conditions. Phototrophic growth with moderate light intensity (1000 lux) at 23° C. was found to support highest magnetic responses and reasonable/robust growth compared to low light conditions or high light intensity (<400 lux, 9000 lux). Therefore, cells were grown under these conditions in all subsequent experiments.

To test whether known mutation phenotypes from *M. gryphiswaldense* could be replicated in *R rubrum*, variants of expression cassettes were constructed, in which single genes were omitted from the mamAB operon by deletion within the cloning host *E. coli*. The small (77 amino acids) MamI protein was previously implicated in MM vesicle formation and found to be essential for magnetosome synthesis (Murat, D. et al. (2010) *Proc. Natl. Acad. Sci. USA* 107, 5593-5598). *R. rubrum*_ABG6X-dI failed to express magnetosome particles (FIG. 13), which resembles the phenotype of a mamI deletion in the related *M. magneticum*. Another tested example was MamJ, which is assumed to connect magnetosome particles to the cytoskeletal magnetosome filament formed by the actin-like MamK (Scheffel, A. et al. (2006) *Nature* 440, 110-114). As in *M. gryphiswaldense*, deletion of mamJ caused agglomeration of magnetosome crystals in about 65% of *R. rubrum*_ABG6X-dJ cells (FIGS. 2a v and 13, TABLE 1). Altogether, these observations indicate that magnetosome biogenesis and assembly within the foreign host are governed by very similar mechanisms and structures as in the donor, which are conferred by the transferred genes.

In *M. gryphiswaldense* and other magnetotactic bacteria, magnetite synthesis occurs within intracellular vesicles surrounded by the magnetosome membrane (MM). In cells of *R. rubrum*_ABG6X vesicular structures surrounding small, immature magnetite crystals were occasionally detected in thin-sectioned cells or by cryo-electron tomography (CET) that, however, were difficult to be distinguished from the highly abundant intracytoplasmic membranes (ICMs) having diameters of 93±34 nm (FIG. 11). Particles that were isolated from disrupted cells by magnetic separation and centrifugation were clearly surrounded by a layer of organic material (3.6±1.2 nm), resembling the magnetosome membrane attached to isolated magnetosomes of *M. gryphiswaldense* (3.2±1.0 nm). This organic layer could also be seen by means of CET (3.4±0.9 nm). Smaller, apparently immature crystals (19±6 nm) were sometimes surrounded by partially empty vesicles (66±6 nm) visible both in micrographs of negatively stained samples and cryo-electron tomograms (FIG. 11). Although these vesicular structures overlapped with the reported size range of *R. rubrum* chromatophores (50-150 nm) (Cohen-Bazire, G. and Kunisawa, R. (1963) *J Cell Biol* 16, 401-419), no vesicles larger than 100 nm surrounding the magnetic particles were detected, whereas 28% of ICM vesicles had a size of 100-170 nm. Biomineralization was severely impaired in the absence of ICM, as transfer of the entire gene set into an ICM deficient mutant of *R. rubrum* (strain GN21) resulted in a very weak magnetic response ($C_{mag}$=0.02), with only a minor portion of cells (~10%) harboring magnetic particles of 27 nm, if grown under microoxic conditions in the dark. Occasionally empty vesicles were observed in GN21_ABG6X (FIG. 11), which were absent from untransformed cells. These observations seems to point towards a scenario in which the ability to synthesize magnetosome membrane-like structures is conferred by the transformed magnetosome operons, rather than adopting pre-existing chromatophore vesicles synthesis of magnetic particles.

Organic material potentially identical with a MM could be solubilized from isolated magnetite crystals of *R. rubrum*_ABG6X by 1% SDS, and less effective also by Triton X-100 treatment (FIGS. 3 and 9), similar as reported for MM of *M. gryphiswaldense* (Grünberg, K. et al. (2004) supra). 1D SDS-PAGE of proteins that co-purified with magnetic particles resolved a complex pattern that displayed several bands of identical size also present in MM preparations from *M. gryphiswaldense* (FIG. 9, arrows). An antibody against MamC, the most abundant protein in the MM of *M. gryphiswaldense* (Grünberg, K. et al. (2004) supra), revealed a band of 12.4 kDa, which was absent from the soluble fraction, but also yielded a faint signal in the non-magnetic membrane fraction, possibly originating from incomplete magnetic separation of the particles during the isolation process or colocalization in empty membrane vesicles (FIG. 9).

In addition to several proteins characteristic for the specialized ICM systems of *R. rubrum* (LH complex, reaction center, cytochrome C, ATP synthases) (Smith, L. (1954) *Bacteriol. Rev.* 18, 106-130; Pace, G. W. et al. (1979) *European J. Appl. Microbiol. Biotechnol.* 6, 271-278 (1979); Wang, Z. Y. et al. (2005). *J. Mol. Biol* 347, 465-477), mass spectrometry identified several magnetosome proteins from *M. gryphiswaldense* (MamJ, MamK, MamC, MamD, MamE, MamO, MamH, MamY, Mms6, MamA, MmsF, MamF, MamM) among most abundant proteins in the putative MM). These findings might indicate a physical connection between magnetosomes and ICMs, or alternatively presence of highly abundant chromatophore proteins might simply result from cross-contamination during cell disruption. The subcellular localization of selected single magnetosome proteins in *R. rubrum* dependent on the presence of further determinants encoded by the transferred genes. Whereas GFP fusions to either MamJ, or MamC in displayed a dispersed pattern in the untransformed *R. rubrum*, a filamentous/chain-like fluorescent signal became apparent in the *R. rubrum*_ABG6X background in which the full complement of magnetosome genes is present, reminiscent to the magnetosome-chain localization of these proteins in *M. gryphiswaldensis* (Scheffel, A. et al. (2006) *Nature* 440, 110-114; Lang, C. and Schüler, D. (2008) supra) (FIG. 8).

In order to further verify whether phenotypic effects known from magnetosome gene mutations in *M. gryphiswaldense* could be replicated in *R. rubrum*, variants of the expression cassettes were constructed, in which single genes were deleted from the mamAB operon.

For example, *R. rubrum*_ABG6X-dI failed to express magnetic particles as revealed by $C_{mag}$ and TEM, which phenotypicxally paralleled the deletion of mamI in *M. magneticum* (Murat, D. et al. (2010) *Proc. Natl. Acad. Sci. USA* 107, 5593-5598). Another example is MamJ, which is assumed to connect magnetosome particles to the actin-like cytoskeletal magnetosome filament formed by MamK. Deletion of mamJ did not affect biomineralization, but caused agglomeration of magnetic particles in *R. rubrum*_ABG6X-dJ (FIG. 3), much as observed in *M. gryphiswaldense* (Scheffel, A. et al. (2006) supra), indicating that also the chain-like assembly of magnetosome crystals is genetically controlled in *R. rubrum*_ABG6X (FIG. 13).

The size of the magnetic particles in *R. rubrum*_ABG6X was still smaller compared to those formed in the donor organism *M. gryphiswaldense*. This raised the question whether full expression of biomineralization may depend on the presence of auxiliary gene functions, which were recently identified also outside the transferred gene clusters (refs nap, feo). Thus, we genetically introduced a ferrous iron transporter (FeoAB1), which has been found to exhibit accessory functions for magnetosome biomineralization (Rong, C. et al. (2008) *Res. Microbiol.* 159, 530-536). Genomic insertion of feoAB1, in addition to the mamAB, mamGFDC, mms6, and mamXY operons, into strain *R. rubrum*_ABG6X resulted in strain *R. rubrum*_ABG6X_feo, which displayed a further increased iron content size of the particles increased significantly, approaching the crystal size of *M. gryphiswaldense*. (FIG. 3).

As magnetosomes in *R. rubrum*_ABG6X were still smaller than those of *M. gryphiswaldense*, it was asked whether full expression of biomineralization may depend on the presence of further auxiliary functions possibly encoded outside the canonical magnetosome operons. For instance, deletion of feoB1 encoding a constituent of a MTB-specific ferrous iron transport system caused fewer and smaller magnetosomes in *M. gryphiswaldense* (Rong et al. (2008) supra). Strikingly, insertion of feoAB1 into *R. rubrum* strain ABG6X resulted in even larger, single-crystalline and twinned magnetosomes and longer chains (440 nm) (FIG. 2a vi, TABLE 1). The size (37 nm) of the crystals approached that of the donor and cellular iron content was substantially increased (0.28% of dry weight) compared to R. rubrum_ABG6X (0.18%), although still lower than in M. gryphiswaldense (3.5%), partly owing to the considerably larger volume of R. rubrum cells (FIG. 2c).

Magnetosome particles could be purified from disrupted cells by magnetic separation and centrifugation and formed stable suspensions (FIG. 3). Isolated crystals were clearly enclosed by a layer of organic material resembling the MM attached to magnetosomes of M. gryphiswaldense. Smaller, immature crystals were surrounded by partially empty vesicles (FIG. 3c inset) that were also seen in thin-sectioned cells (FIGS. 3a and 11) and on average were smaller (66±6 nm) than the abundant photosynthetic intracytoplasmic membranes (ICM) (93±34 nm (FIG. 11). Organic material of the putative MM could be solubilized from isolated magnetite crystals of R. rubrum_ABG6X by various detergents (FIG. 3d), similar as reported for MM of M. gryphiswaldense (Grünberg et al. (2004) supra). Proteomic analysis of the SDS-solubilized MM revealed a complex composition (FIG. 9), and several genuine magnetosome proteins (MamKCJAFDMBYOE, Mms6, MmsF) were detected among the most abundant polypeptides (TABLE 3). An antibody against MamC, the most abundant protein in the MM of M. gryphiswaldense, recognized a prominent band with the expected mass (12.4 kDa) also in the MM of R. rubrum_ABG6X (FIG. 9).

The subcellular localization of selected magnetosome proteins in R. rubrum depended on the presence of further determinants encoded by the transferred genes. For example, GFP fusions of MamC displayed a punctuate pattern in the R. rubrum wild-type background. In contrast, a filamentous fluorescent signal became apparent in the majority of cells (79%) of the R. rubrum_ABG6X background in which the full complement of magnetosome genes is present (FIG. 10), reminiscent of the magnetosome-chain localization of these proteins in M. gryphiswaldense.

The heterologous production of magnetic nanoparticles in R. rubrum should result in a significant increase in yield as compared to M. gryphiswaldense. From large cultures of M. gryphiswaldense, a maximal cell yield of 1 g fresh weight per liter of culture can be typically obtained, resulting in a final yield of 10 mg magnetic nanoparticles (i.e. magnetite) per liter of culture. With R. rubrum, a cell yield of up to 60 mg per liter can be accomplished (by means of high cell-density fermentation). However, in R. rubrum, the relative amount of magnetite per cell mass can be estimated to be only about 20% of that in M. gryphiswaldense. Nevertheless, due to the much higher cell density of R. rubrum, a final yield of 100-120 mg magnetic nanoparticles (i.e. magnetite) per liter of culture can be calculated, that is, an increase by a factor of 10-12 as compared to M. gryphiswaldense.

In a further analysis, a recombinant M. gryphiswaldense strain harboring, in addition to its endogenous copies of the mamAB, mamGFDC, mms6, and mamXY operons, additional (i.e. genetically introduced) copies of the respective four expression cassettes, produced about two times the amount of magnetic nanoparticles than the corresponding wild-type strain (data not shown), thus suggesting the "gene copy number" as a further important determinant for improving the overall yield of magnetic nanoparticles produced.

3. Homologous Overexpression of the Pathway for Producing Magnetosomes in *Magnetospirillum gryphiswaldense*

3.1 Overexpression of the mms6 and mamGFDC Operons

In order to control overexpression of different magnetosome operons, M. gryphiswaldense MSR was engineered by mariner- or Tn5 transposon-driven random chromosomal insertion (FIG. 14). Transconjugants were obtained at frequencies between $2\text{-}5 \times 10^{-7}$, and chromosomal insertions were stably inherited as indicated by the ability of transformed strains to grow in the presence of kanamycin after 120 generations without antibiotic selection. All insertants essentially displayed wild type-like growth.

Chromosomal duplication of the mms6 operon resulted in strain ΔRecA+mms6 1× that possesses one native and one inserted mms6 operon, and remarkably increased magnetosome biomineralization. The mutant strain synthesized 36% more crystals per cell (47 compared to 34 magnetosomes per cell within ΔRecA (TABLE 6)) with an increased size of 46 nm (ΔrecA=36 nm) and formed a high proportion of multiple chains that were less frequently observed in ΔRecA. Intracellular iron content of ΔRecA+mms6 1× was increased by 14.9±2.9%. Insertion of two further mms6 operons (one native and two inserted mms6 operons) in strains ΔrecA+mms6 2× lead in average (n=1183) to 54 magnetite particles per cell with a size of 48 nm that corresponds to an increase in number by 58%, size by 35%, and intracellular iron content of 34.8±2.5% compared to ΔRecA (FIG. 14, TABLE 6). ΔRecA+mms6 3× carrying four copies of mms6 operon produced 58 magnetite crystals per cell with a diameter of 44 nm and an intracellular iron content increased from 2.68% to 3.73% iron per dry weight, which represents only a slight further increase compared to ΔrecA+mms6 2× (increase by 38.8±2.5% compared to ΔRecA (FIG. 14, TABLE 6). Cultivation under anaerobic conditions with 50 μM or 500 μM iron did not significantly increase iron uptake of ΔRecA+mms6 3× compared to cultivation under microaerobic conditions with 50 μM iron. Insertion of four additional copies of the mms6 operon in ΔRecA+mms6 4× (5 mms6 operons in total) did not further increase biomineralization, but caused a size reduction of 13% and 6% compared to ΔRecA+mms6 2× and ΔRecA+mms6 3×, respectively. Cultivation of overproducing strains ΔRecA+mms6 2× at higher iron concentrations (250 μM iron) did not further increase magnetosome numbers, although size distributions were slightly shifted towards to larger crystals with maximum sizes up to 85 nm.

In anaerobically grown cells of ΔRecA+mms6 2× and ΔRecA+mms6 3× a variable proportion of enlarged vesicle with were visible in cryo-electron tomograms (FIG. 14). These vesicles appeared as regularly shaped as in the wild type, but their size was increased up to 119 nm (ΔRecA+mms6 2×), whereas wild type (WT) vesicles had a maximum size of 54 nm. However, the ratio between the size of the vesicle and the particle sizes measured by means of tomography was similar and not significantly increased (ΔRecA+mms6 2×: 2.8±0.8; ΔRecA+mms6 3×: 2.3±0.9; WT: 2.1±1.4).

As the parental strain ΔRecA, all overexpression strains had a variable proportion of small vibrioid and elongated cells. On average, cells became more elongated with increasing copy number of inserted mms6 operons (4.53±1.59 µm; 4.56±1.46 µm; 5.10±1.95 µm; and 5.3±1.7 µm for ΔRecA+mms6 1×, 2×, 3×, and 4×, respectively, as compared to 4.44±1.26 µm for ΔRecA (FIG. 15A). Shorter cells (<10 µm) of ΔRecA+mms6 2× contained fewer particles with smaller magnetite crystals (43 nm), whereas highly elongated cells (>10 µm) had significantly more (53-138 particles, mean: 104; n=572, equivalent to a 206% increase) and larger magnetite crystals (49 nm) with a maximum size of 80 nm (FIG. 14). As observed via TEM, in ΔRecA+mms6 2×, and 3× cells, the magnetosome chains were persistently located at the mid of the cells and split into two sub-chains during cell division, similar as in the wild type (Katzmann, E. et al. (2011) *Mol. Microbiol.* 82, 1316-1329). However, cells of ΔRecA+mms6 2× and 3× frequently remained connected by tubular extensions at advanced stages of constriction, which kept the daughter cells attached to each other and hampered their separation. In these tubular extensions, few magnetosome particles (2-10) were encapsulated and separated from daughter chains (FIG. 15B).

Next, overexpression of the mamGFDC operon, which is adjacent to the mms6 operon, was investigated. While duplication of mamGFDC alone had only a weak effect on crystal number per cell (mean: 36; n=419), the duplication of both the mms6 and mamGFDC operons (RecA+mms6/GFDC) caused the synthesis of 32% more crystals per cell (mean: 45; n=483). Intracellular iron content of RecA+mamGFDC was increased by 7.4%±1.1% and even further by 14.1%±1.9% in RecA+mms6/GFDC. RecA+mamGFDC and RecA+mms6/GFDC produced 26%, and 27% larger crystals, respectively, as compared to ΔRecA (TABLE 6).

In summary, the genomic insertion of up to additional three mms6 operons resulted in enhanced biosynthesis of magnetosomes with both increased particle sizes and numbers. However, the introduction of either additional mms6 operon copies or the combined overexpression of mamGFDC did not further increase biomineralization, thus suggesting that magnetosome synthesis was limited by factors encoded elsewhere, which control growth of magnetite particles other than by vesicle sizes, such as iron transport, activation and nucleation of crystals. Hence, it was attempted to overexpress the large mamAB operon that encodes most magnetosome proteins being essential for magnetosome formation.

3.2 Overexpression of the mamAB Operon

Transfer and single-copy chromosomal insertion of the mamAB operon was achieved by mariner transposon based gene delivery into random sites with a conjugational efficiency of $10^{-7}$-$10^{-8}$. As with the smaller mms6 and mamGFDC operons, the mamAB operon was also stable for 40 generations, after repeated passaging under metabolic stress (cold storage, oxidative stress). ΔRecA+mamAB 1× (encompassing one endogenous and one inserted mamAB operon) showed a similar magnetic response like the parent strain ($C_{mag}$=0.8±0.2) and the iron content was not significantly increased (by 0.4±0.5%; TABLE 6). Cells were slightly elongated (4.81±1.82 µm; as compared to ΔRecA: 4.44±1.26 µm; FIG. 15A) and displayed no obvious morphological abnormalities. However, transmission electron microscopy (TEM) analyses revealed phenotypic heterogeneity with respect to magnetosome formation with two distinct "morphotypes" being present in variable proportions, comprising (i) about 47% cells in which the number of regular-sized magnetosomes was increased to 77, (ii) 42% cells in which the number of magnetosomes increased (68) with aberrant crystal sizes and intracellular localization, and (iii) 10% wild type (WT)-like cells (FIG. 16).

Mutant strain ΔRecA+mamAB 2× was constructed by transfer of pTps-mamAB-Gm into insertion mutant ΔRecA+mamAB 1×. The mutant showed a similar phenotype as ΔRecA+mamAB 1×, and the number of magnetosomes did not further increase (68), despite of a slightly increased intracellular iron content (by 9.4±0.5%). The $C_{mag}$ value of ΔRecA+mamAB 2× was even lower than that of the parent strain ($C_{mag}$=0.5±0.2), presumably caused by altered cell dimensions (5.98±2.58 µm, as compared to 4.44±1.26 µm in ΔRecA (TABLE 6, FIG. 15A).

The magnetosome membrane of magnetosome particles isolated from strain ΔRecA+mamAB 1× had the same appearance and thickness of 5.4±1.8 nm as compared to ΔRecA 5.2±1.9 nm. Coomassie-stained SDS-PAGE profiles of magnetosome membranes from strain ΔRecA+mamAB 1× revealed similar patterns compared to ΔRecA. However, in strain ΔRecA+mamAB 1× several bands including magnetosome proteins MamA and MamM, showed higher intensities between 51% and 145%. Western Blot analysis of selected proteins confirmed that MamM and MamA were more abundant in strain ΔRecA+mamAB 1× (by 128% and 145%, respectively), whereas the abundance of MamC was not significantly increased (by 9%), although the Coomassie-stained MamC band appeared more intense in ΔRecA.

In summary, the overexpression of the mamAB operon alone did not consistently enhance magnetosome formation and therefore it appears as if further regulators for biogenesis are necessary to increase magnetosome yield.

3.3 Overexpression of the mamGFDC, mms6, mamAB, and mamXY Operons

In order to generate a mutant strain overexpressing all four operons, the mamAB, mms6, and mamGFDC operons were simultaneously integrated into the genome of ΔRecA that was further modified by insertion of the mamXY operon using mariner transposon based gene delivery, resulting in strain RecA+AB6GX.

The intracellular iron content of the resulting mutant strain was drastically increased to 3.77% iron per dry weight, which is an increase of 140.7%±2.4% as compared to ΔRecA. TEM revealed that the number of magnetosomes per cell was increased by 117% as compared to the parental strain (TABLE 6, FIG. 16A). 28% of the cells contained more than 100 magnetosomes, whereas ΔRecA did not produce more than 58 particles per cell. Most cells formed multiple magnetosome chains (2-4), whereas the wild type exhibited not more than two chains per cell. Aside from cells with proper (WT-like) magnetosome chains localized at the inner convex curvature of the cell, cells with one chain located at the inner convex cell curvature and up to three magnetosome chains at the concave curvature were also frequently observed (FIG. 16B). Additionally, the particles in some cells lacked a clearly ordered chain-like alignment, but were "stuffed" into compact bundles or clusters (FIG. 16C). Notably, the mean size of crystals was only slightly increased to 39 nm.

While strain RecA+mamAB 1× showed two distinct magnetosome "morphotypes", in strain RecA+ABG6X only 12% cells had scattered magnetosomes and aberrant crystal sizes (RecA+mamAB 1×: 42%). The magnetic response of RecA+AB6GX was not affected by the altered biomineralization and consistent with the $C_{mag}$ of parent strain ΔRecA (i.e. $C_{mag}$=0.7).

Mutant cells of strain RecA+ABG6X exhibited delayed growth at 30° C., but wild type growth at 23° C. Additionally, mutant cells were longer (FIG. 16), and in dividing cells tubular extensions during or after cell division were observed. In contrast to the giant magnetosome membrane vesicles observed by cryo-electron tomography (CET) in strains RecA+mms6 2× and RecA+mms6 3×, magnetosome membrane vesicles in strain RecA+ABG6X were not significantly enlarged in relation to the crystals (FIGS. 16E and 16F).

The expression of the FeoAB proteins increased particle size in a heterologous host, suggesting that overexpression of these proteins also enhances particle synthesis. Therefore, the genes feoA and feoB were inserted into RecA+AB6GX by Tn5 transposition. However, crystal sizes were only slightly increased in strain ΔRecA+ABG6X+feo (41 nm as compared to 39 nm in RecA+AB6GX), while crystal numbers per cell even slightly decreased (69 particles as compared to 74 in strain RecA+AB6GX).

4. Conclusions

So far, significant efforts have been made to genetically or metabolically magnetize prokaryotic and eukaryotic organisms/cells (Vainshtein, M. et al. (2002). *Biol Cell* 94, 29-35; Nishida, K. and Silver, P. A. (2012) *PLoS Biol* 10, e1001269). However, engineering resulted in only few undefined, delocalized and poorly crystalline Fe deposits.

This has prompted ideas to transfer genetic parts/the entire pathway for producing magnetic nanoparticle from magnetotactic bacteria in other organisms. Successful transfer and heterologous expression has been demonstrated for other bacterial gene clusters encoding mostly soluble metabolic pathways such as nitrogen fixation (Temme, K., et al. (2012). *Proc. Natl. Acad. Sci. USA* 109, 7085-7090) or synthesis of secondary metabolites (Fischbach, M. and Voigt, C. A. (2010) *Biotechnol. J.* 5, 1277-1290). Furthermore, the ability to synthesize structures, such as microcompartments and gas vesicles by the transfer of few genes has also been shown in foreign hosts (Li, N. and Cannon, M. C. (1998) *J. Bacteriol* 180, 2450-2458 (1998) Bonacci, W. et al. (2012) *Proc Natl Acad Sci USA* 109, 478-483).

However, transfer and reconstitution of a structurally and genetically similarly complex gene pathways or organelles, which requires the balanced expression of a multitude of structural and catalytic membrane-bound factors has not yet been achieved. The present findings are important for a number of reasons. First, they demonstrate that the 30 genes derived from the mamAB, mamXY, mamGFDC and mms6 operons constitute a minimal gene set which supports the biomineralization and assembly of magnetosome chains in heterologous host cells, but auxillary functions encoded outside the genomic MAI are required for magnetosome formation as well, although the mamAB operon alone has been shown to be sufficient for some rudimentary biomineralization in *M. gryphiswaldense* (Lohsse, A. et al. (2011) supra).

The distribution of similar MAI-like gene clusters in all the phylogenetically diverse magnetotactic bacteria analyzed stimulated two different hypotheses: horizontal gene transfer vs. vertical inheritance from a magnetic ancestor. However, the inheritance of magnetosome genes has remained unsolved so far. The present results provide first experimental evidence that the gene pathway for the production of magnetosomes can be transferred horizontally to a phototrophic organism and thus pointing towards a possible evolutionary link between magnetosome formation and phototrophy. In addition, the data demonstrate that genetic multiplication of the entire biosynthesis pathway results in significant overproduction of magnetic nanoparticles in homologous host, also indicates a feasible and promising strategy for high-yield production in heterologous hosts Functional reconstitution of the magnetosome pathway will provide for an analysis of gene functions by "surrogate genetics" in genetically more amenable host cells, thus resulting in an improved/and sustainable production of magnetic nanoparticles as compared to the homologous system. Furthermore, the present findings might also enable synthetic biology approaches for production of tailored magnetic nanoparticles in both prokaryotic and eukaryotic organisms, for example, for the in vivo synthesis of magnetic nanoparticles for applications in "magnetogenetics" such as magneto-thermal and magneto-mechanical stimulation of ion channels, or for the endogenous expression of a magnetic reporter for biomedical imaging (e.g., MRI).

The present invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modifications and variations of the inventions embodied therein may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

TABLE 1

Summary of magnetic responses ($C_{mag}$), intracellular iron content and crystal size and number of various strains (median values, ± = standard deviation).
If not indicated otherwise, cells were grown in the presence of 50 μM ferric citrate. Magnetic response and total iron content were measured with (n) biological replicates under identical conditions. For determination of crystal size and number per cell, (n) cells of one clone were analyzed by TEM. The Mann-Whitney test (http://elegans.som.vcu.edu/~leon/stats/utest.html) was performed for crystal size comparison of R. rubrum_ABG6X and R. rubrum_ABG6X_feo: the difference was highly significant (p < 0.001, two tailed test). Crystal size comparison of R. rubrum_ABG6X_feo and M. gryphiswaldense revealed no significant difference ($p \geq 0.05$, two tailed test).

| Strain | ($C_{mag}$) | Iron content (% dry weight) | Crystal size (nm) | Crystal number per cell |
|---|---|---|---|---|
| M. gryphiswaldense MSR-1 | 1.4 ± 0.2 (n = 3) | 3.5 (n = 3) | 36 ± 9 (n = 310) | 24 ± 8 (n = 52) |
| M. gryphiswaldense ΔmamAB_AB | 1.2 ± 0.2 (n = 3) | n.d. | 37 ± 10 (n = 112) | 23 ± 7 (n = 24) |
| M. gryphiswaldense MSR-1B_AB | 0.2 (n = 3) | n.d. | 17 ± 6 (n = 112) | 16 ± 6 (n = 20) |
| M. gryphiswaldense MSR-1B_ABG | 0.6 ± 0.1 (n = 3) | n.d. | 25 ± 6 (n = 104) | 13 ± 6 (n = 20) |
| M. gryphiswaldense MSR-1B_ABG6 | 0.9 ± 0.2 (n = 3) | n.d. | 35 ± 8 (n = 103) | 18 ± 8 (n = 22) |
| R. rubrum ATCC 11170 | — | 0.07 ± 0.04 (n = 3) | — | — |
| R. rubrum_AB | — | 0.08 (n = 3) | — | — |
| R. rubrum_ABG | — | 0.10 ± 0.01 (n = 3) | — | — |
| R. rubrum_ABG6 | — | 0.17 (n = 4) | 12 ± 6 (n = 304) | 26 ± 10 (n = 50) |
| R. rubrum_ABG6X | 0.3 ± 0.2 (n = 3) | 0.17 ± 0.02 (n = 4) | 24 ± 7 (n = 307) | 10 ± 4 (n = 50) |
| R. rubrum_ABG6X 500 μM ferric citrate | 0.3 (n = 4) | n.d. | 25 ± 7 (n = 301) | 11 ± 5 (n = 51) |
| R. rubrum_ABG6X 100 μM ferrous sulfate | 0.2 (n = 4) | n.d. | 24 ± 8 (n = 312) | 10 ± 5 (n = 52) |
| R. rubrum_ABG6X_ftsZm | 0.6 ± 0.1* (n = 3) | 0.18 ± 0.03 (n = 3) | 26 ± 9 (n = 300) | 11 ± 4 (n = 51) |
| R. rubrum_ABG6X_dJ | 0.2 (n = 3) | 0.18 ± 0.01 (n = 3) | 27 ± 9 (n = 300) | 9 ± 4 (n = 50)** |
| R. rubrum_ABG6X_dI | — | 0.09 ± 0.07 (n = 3) | — | — |
| R. rubrum_ABG6X_feo | 0.8 ± 0.1 (n = 3) | 0.28 ± 0.07 (n = 3) | 37 ± 10 (n = 300) | 10 ± 4 (n = 52) |

*The slightly increased $C_{mag}$ is likely due to effects of the genuine cell division protein FtsZm on cell morphology, as no difference in iron content and crystal size or number per cell was detectable.
**64% of mutant cells (n = 32) harbored clustered magnetosomes, whereas 36% still showed a chain-like alignment of magnetosomes (n = 18).

TABLE 2

Results of BLAST analysis of 16S rRNA gene of M. gryphiswaldense against R. rubrum and potential production strains.
Organisms were selected based on their close phylogenetic affiliation, availability of a genetic system or predominant role in heterologous protein expression.

| Organism | Phylogenetic class | 16S rRNA gene identity (%) | NCBI Accession number |
|---|---|---|---|
| Rhodospirillum rubrum | Alphaproteobacteria | 90 | NR_074249 |
| Caulobacter crescentus | Alphaproteobacteria | 88 | AE005673 |
| Rhodobacter sphaeroides | Alphaproteobacteria | 87 | CP000144 |
| Rhodobacter capsulatus | Alphaproteobacteria | 86 | NR_102927 |
| Agrobacterium tumefaciens | Alphaproteobacteria | 88 | AJ012209 |
| Escherichia coli | Gammaproteobacteria | 83 | U00096 |

TABLE 3

Magnetosome proteins identified in the MM of strain R. rubrum_ABG6X by nano-electrospray ionization-LC tandem MS (ESI-LC-MS/MS).
Spectra were analyzed via Mascot™ software using the NCBI nr Protein Database and a database from M. gryphiswaldense (asterisks; Richter, M. et al. (2007) J. Bacteriol. 189, 4899-4910). Proteins are listed in the order of their exponentially modified protein abundance index (emPAI). The data have been deposited to ProteomeXchange with identifier PXD000348 (DOI 10.6019/PXD000348).

| Protein | Acc. No. | Coverage (%) | No. of spectrum matches | No. of seq. peptides | MW (kDa) | emPAI | Putative function |
|---|---|---|---|---|---|---|---|
| MamK | MGR_4093 | 57 | 9 | 9 | 39.6 | 1.51 | Magnetosome chain assembly/positioning |
| MamC | MGR_4078 | 32 | 4 | 3 | 12.4 | 1.01 | Crystal size and shape control |
| MamJ | MGR_4092 | 32 | 10 | 6 | 48.6 | 0.76 | Magnetosome chain assembly |
| MamA | MGR_4099 | 37 | 1 | 1 | 23.9 | 0.65 | TPR-like protein assoc. with the MM |
| MamF | MGR_4076 | 17 | 1 | 1 | 12.4 | 0.60 | Magnetosome size and shape control |
| Mms6 | MGR_4073 | 19 | 1 | 1 | 12.7 | 0.58 | Magnetosome crystallization |

TABLE 3-continued

Magnetosome proteins identified in the MM of strain *R. rubrum*_ABG6X by nano-electrospray ionization-LC tandem MS (ESI-LC-MS/MS). Spectra were analyzed via Mascot ™ software using the NCBI nr Protein Database and a database from *M. gryphiswaldense* (asterisks; Richter, M. et al. (2007) *J. Bacteriol.* 189, 4899-4910). Proteins are listed in the order of their exponentially modified protein abundance index (emPAI). The data have been deposited to ProteomeXchange with identifier PXD000348 (DOI 10.6019/PXD000348).

| Protein | Acc. No. | Coverage (%) | No. of spectrum matches | No. of seq. peptides | MW (kDa) | emPAI | Putative function |
|---|---|---|---|---|---|---|---|
| MamD | MGR_4077 | 20 | 3 | 3 | 30.2 | 0.49 | Crystal size and shape control |
| MamM* | MGR_4095 | 15 | 3 | 3 | 34.7 | 0.42 | Iron transport/MM assembly |
| MmsF* | MGR_4072 | 8 | 2 | 1 | 13.9 | 0.23 | Crystal size and shape control |
| MamB* | MGR_4102 | 7 | 1 | 1 | 32.1 | 0.21 | Iron transport/MM assembly |
| MamY* | MGR_4150 | 18 | 2 | 2 | 40.9 | 0.16 | Tubulation and MM formation |
| MamO* | MGR_4097 | 6 | 3 | 3 | 65.3 | 0.15 | Magnetosome crystallization |
| MamE | MGR_4091 | 4 | 2 | 2 | 78.3 | 0.08 | Magnetosome crystallization |

TABLE 4

Strains and plasmids used in this study.

| Strain or plasmid | Characteristics | Reference or source |
|---|---|---|
| *M. gryphiswaldense* MSR-1 | Wild-type (wt) | DSM-6361; Schleifer, K. et al. (1991) Syst. |
| *M. gryphiswaldense* MSR-1B | spontaneous unmagnetic mutant lacking parts of the MAI | Schübbe, S. et al. (2993) J. Bacteriol. 185, 5779-5790 |
| *M. gryphiswaldense* ΔmamAB | mamAB deletion mutant | Lohsse, A. et al. (2011) *PLoS One* 6, e25561 |
| *M. gryphiswaldense* ΔmamAB_AB | Km$^R$, transposon mutant with inserted mamAB operon | This study |
| *M. gryphiswaldense* MSR-1B_AB | Km$^R$, transposon mutant with inserted mamAB operon | This study |
| *M. gryphiswaldense* MSR-1B_ABG | Km$^R$, Spec$^R$, transposon mutant with inserted mamAB and mamGFDC operon | This study |
| *M. gryphiswaldense* MSR-1B_ABG6 | Km$^R$, Cm$^R$, transposon mutant with inserted mamAB, mamGFDC an mms6 operon | This study |
| *R. rubrum* ATCC 11170 | Wild-type (wt) | Pfenning, N. H. G. (1971) *Int. J. Syst. Bacteriol.* 21, 19-24 |
| *R. rubrum*_AB | Km$^R$, transposon mutant with inserted mamAB operon | This study |
| *R. rubrum*_ABG | Km$^R$, Spec$^R$, transposon mutant with inserted mamAB and mamGFDC operon | This study |
| *R. rubrum*_ABG6 | Km$^R$, Cm$^R$, transposon mutant with inserted mamAB, mamGFDC and mms6 operon | This study |
| *R. rubrum*_ABG6X | Km$^R$, Cm$^R$, Gm$^R$ transposon mutant with inserted mamAB, mamGFDC, mms6 and mamXY operon (without ftsZm) | This study |
| *R. rubrum*_ABG6X_dJ | Km$^R$, Cm$^R$, Gm$^R$, Ap$^R$ transposon mutant with inserted mamAB (mamJ deletion), mamGFDC, mms6 and mamXY operon (without ftsZm) | This study |
| *R. rubrum*_ABG6X_dI | Km$^R$, Cm$^R$, Gm$^R$, Ap$^R$ transposon mutant with inserted mamAB (mamI deletion), mamGFDC, mms6 and mamXY operon (without ftsZm) | This study |
| *R. rubrum*_ABG6X_ftsZm | Km$^R$, Cm$^R$, Gm$^R$, Tc$^R$ transposon mutant with inserted mamAB, mamGFDC, mms6 and mamXY operon (without ftsZm) and ftsZm under control of an inducible lac promoter | This study |
| *R. rubrum*_ABG6X_feo | Km$^R$, Cm$^R$, Gm$^R$, Tc$^R$ transposon mutant with inserted with inserted mamAB, mamGFDC, mms6, mamXY and feoAB1 operon | This study |
| *R. rubrum*_GFDC-EGFP | Tc$^R$ transposon mutant with inserted mamGFDC-EGFP | This study |
| *R. rubrum*_ABG6X_GFDC-EGFP | Km$^R$, Cm$^R$, Gm$^R$, Tc$^R$ transposon mutant with inserted mamAB, mamGFDC, mms6 and mamXY operon (without ftsZm) and mamGFDC-EGFP | This study |

TABLE 4-continued

Strains and plasmids used in this study.

| Strain or plasmid | Characteristics | Reference or source |
|---|---|---|
| R. rubrum_J-EGFP | Tc$^R$ transposon mutant with inserted mamGFDC-EGFP | This study |
| R. rubrum_ABG6X_J-EGFP | Km$^R$, Cm$^R$, Gm$^R$, Tc$^R$ transposon mutant with inserted mamAB, mamGFDC, mms6 and mamXY operon (without ftsZm) and mamJ-EGFP | This study |
| E. coli DH10b | F- mcrA Δ(mrr-hsdRMS-mcrBC) φ80lacZΔM15 ΔlacX74 recA1 endA1 araD139 Δ(ara leu) 7697 galU galK rpsL nupG λ- | Invitrogen |
| E. coli BW29427 | dap auxotroph derivative of E. coli strain B2155 | K. Datsenko & B. L. Wanner, unpublished |
| E. coli WM3064 | thrB1004 pro thi rpsL hsdS lacZΔM15 RP4-1360 Δ(araBAD)567 ΔdapA1341::[erm pir] | W. Metcalf, kindly provided by J. Gescher, KIT Karlsruhe |
| pSC101-BAD-gbaA | Tc$^R$, replicative plasmid containing redα/redβ recombinases under the control of a L-Arabinose inducible promoter, temperature sensitive origin of replication | Wang, J. et al. (2006) Mol. Biotechnol. 32, 43-53 |
| p15A-Tps-oriT-Km | Km$^R$, BSD$^R$, oriT, p15A origin of replication, mariner tps, cloning cassette | Fu, J. et al. (2008) Nucleic Acids Res. 36, e113 |
| pSSK18 (BAC_mamAB) | BAC containing the mamAB operon from M. gryphiswaldense | Schübbe, S. et al. (2993) J. Bacteriol. 185, 5779-5790 |
| pTps_AB | Km$^R$, BSD$^R$, mariner tps vector containing mamAB operon | This study |
| pTps_ABG | Spec$^R$, Km$^R$, BSD$^R$, mariner tps vector with mamAB and mamGFDC operon | This study |
| pTps_ABG6 | Cm$^R$, Km$^R$, BSD$^R$, mariner tps vector with mamAB, mamGFDC, and mms6 operon | This study |
| pTps_XYZ | Gm$^R$, BSD$^R$, mariner Tps vector with mamY, mamX and mamZ | This study |
| pTps_ABG6_dJ | Cm$^R$, Km$^R$, BSD$^R$, Ap$^R$, mariner tps vector with mamAB, mamGFDC, and mms6 operon, (mamJ deletion) | This study |
| pTps_ABG6_dI | Cm$^R$, Km$^R$, BSD$^R$, Ap$^R$, mariner tps vector with mamAB, mamGFDC, and mms6 operon, (mamI deletion) | This study |
| pBAM1 | Km$^R$, Ap$^R$, γR6K origin of replication, oriT, Tn5 vector | Martinez-Garcia, E. et al. (2011) BMC Microbiol. 11, 38 |
| Tet-pBAM1 | Tc$^R$, Ap$^R$, γR6K origin of replication, oriT, Tn5 vector | This study |
| pBam_mamGFDC-EGFP | Tc$^R$, Ap$^R$, mamGFDC operon under control of P$_{mamDC}$ with a C-terminal EGFP fusion, Tn5 vector | This study |
| pBam_MamJ-EGFP | Tc$^R$, Ap$^R$, mamJ under control of P$_{mamDC}$ with a C-terminal EGFP fusion, Tn5 vector | This study |
| pRU-1feoAB | Km$^R$, broad host range pBBRMCS2, feoAB1 operon under the control of P$_{mamH}$ | R. Uebe, unpublished |
| pBam-feoAB1 | Tc$^R$, Ap$^R$, feoAB1 operon under the control of P$_{mamH}$, Tn5 vector | This study |
| pBam-ftsZm_mCherry | Tc$^R$, Ap$^R$, ftsZm, lacI with a C-terminal mCherry fusion under control of inducible P$_{lac}$, Tn5 vector | This study |
| pFM211 | Km$^R$, broad host range pBBRMCS2, lacI, ftsZm with C-terminal mCherry fusion, mamK with N-terminal EGFP fusion | F. Müller, unpublished |

Km$^R$ = kanamycin resistance, Tc$^R$ = tetracycline resistance, Ap$^R$ = ampicillin resistance, BSD$^R$ = blasticidin S resistance, Cm$^R$ = chloramphenicol resistance, Gm$^R$ = gentamicin resistance, Spec$^R$ = spectinomycin resistance.

TABLE 5

Oligonucleotides used in this study.

| SEQ ID NO: | Primer | Nucleotide sequence (5'-3')$^a$ | Product |
|---|---|---|---|
| 1 | Mam-tps5 | AATTCGCACGGACTATAGCAACGAATCGAGGTCGGTTGACAAGCCATAAATCAGAAGAACTCGTCAAGAAGGC | p15A-Tps-oriT-Km, ET-recombination with BAC_mamAB, pTps_AB |
| 2 | Mam-tps3 | GAACGAAGATGAGACAGAAATCCGTGGCGCCGAGCGTAAGCATCCGGTGAGAACCTCATTCCCTCATGATACAG | |
| 3 | mamGFC3 | TATCATGAGGGAATGAGGTTCTCACCGGATGCTTACGCTCGGCGCCAGAGCACATCGGGGTGAATGACGAC | mamGFDC operon, ET-recombination with pTps_AB |
| 4 | mamGFC5 | CGCTAGCTGCGGGTTATTCGCATTTGC | |
| 5 | spectMam3 | TCAAAACCCGCGCAGAGGCAAATGCGAATAACCCGCAGCTAGCGTTATAATTTTTTTAATCTGTTATT | Spectinomycin resistance cassette, ET-recombination with pTps_AB |
| 6 | spectMam5 | TGATCCGCTATGGTAAGCGCATCATGTCCGGATCCCATGGCGTTCCGCTCGTAACGTGACTGGCAAGAGATATT | |
| 7 | mms6cm5 | TACTGCGATGAGTGGCAGGGCGGGGCGTAAGCTTACAATTTCCATTCGCCATTC | mms6 operon, ET-recombination with pTps_ABG |
| 8 | mms6mam3 | GTGCTTCGCTGTGTCCACAAGAACC | |

TABLE 5-continued

Oligonucleotides used in this study.

| SEQ ID NO: | Primer | Nucleotide sequence (5'-3')[a] | Product |
|---|---|---|---|
| 9 | cm-mms6-3 | TGGCGAATGGAAATTGTAAGCTTACGCCCCGCCCTGCCACTC | Chloramphenicol resistance cassette, ET-recombination with pTps_ABG |
| 10 | cm-mms6-5 | TGATCCGCTATGGTAAGCGCATCATGTCCGGATCCCATGGCGTTCCGCTCGTCCTGGTGTCCCTGTTGATACC | |
| 11 | IK097 | TCTAGAGGGCCCCAACTTTTTCGCTTTACTAGCTCTTAGTTCTCCAATAAATTCCCTGCGTCGA | $P_{mamDC}$ in pBAM1 |
| 12 | IK098 | CATATGCTGATCTCCGGCAAGTGTATGCACGATTCCCTCTCTGCCCTTAAAATCGACGCAGGGAAT | |
| 13 | IK107 | CATATGATCAAGGGCATCGCGGG | mamGFDC operon in pBAM1 |
| 14 | IK101 | GGTACCGGCCAATTCTTCCCTCAGAA | |
| 15 | IK102 | GGTACCGGAGGCGGAGGCGGT | egfp in pBAM1 |
| 16 | IK103 | GAATTCTTACTTGTACAGCTCGTCCATG | |
| 17 | IK163 | GAATTCTTAGCCGATTCGCAG | mamXY-operon (without ftsZm), ET-recombination with p15A-Tps-oriT-Gm |
| 18 | IK164 | GAGCTCGGCAGCCTCATTTAAA | |
| 19 | IK173 | CCGGAATTGCCAGCTGGGGCGCCCTCGGTAAGGTTGGGAAGCCCTGCAACGTATAATATTTGCCCATG | Gentamicin resistance cassette, ET-Recombination with p15A-Tps-oriT-Km |
| 20 | IK174 | AGGCGATAGAAGGCGATGCGCTGCGAATCGGGAGCGGCGATACCGTAAAGCGATCTCGGCTTGAA | |
| 21 | IK208 | CCCGGTACCCAGCTTTTGTTCCCTTTAGTGAGGGTTAATTGCGCGCTTGGCCTCATTCCCTCATGATACAGAGAC | p15A-Tps-oriT-Gm, ET-recombination with mamXY |
| 22 | IK209 | GGCGTTACCCAACTTAATCGCCTTGCAGCACATCCCCCTTTCGCCAGCTGTCTCGGCTTGAACGAATTG | |
| 23 | IK213 | GACGTCGAGCCACGGCG | Tetracycline resistance cassette in pBAM1 |
| 24 | IK214 | GGGTCCCTCAGGTCGAGGTGGC | |
| 25 | IK215 | TCTAGACTACAAGAATGTCCCGC | feoAB1 operon + $P_{mamH}$ in pBAM1 |
| 26 | IK216 | GAATTCGGCATCCTGATCGGT | |
| 27 | IK217 | CATATGATGGCAAAAACCGG | mamJ in pBAM1 |
| 28 | IK218 | GGCGGTACCTTTATTCTTATCTTCAGCATCAC | |
| 29 | IK235 | GGGTGGAGCGGGATAATGGCAAAAAACCGGCGTGATCGGCACGGCTAAATACATTCAAATATGTATCC | Ampicillin resistance cassette insertion into mamJ of pTps_ABG6 |
| 30 | IK236 | CTATTTATTCTTATCTTCAGCATCACATTTCGGCGATGAACAACTACCTTACCAATGCTTAATCAGTG | |
| 31 | IK239 | CGCCGCTTGTGTTCTGTATCAAGACTGGAGAACGTTTATGCCAACTAAATACATTCAAATATGTATCC | Ampicillin resistance cassette Insertion into mamI of pTps_ABG6 |
| 32 | IK240 | TCAACCATCGATGTTAGGGTCTGAGTTCGCCCTCTTACCGGCAGGTTACCAATGCTTAATCAGTG | |
| 33 | IK251 | AAACCGCCCAGTCTAGCTATCGCCATGTAAGCCCACTGCAAGCTACCTGCCCTCATTCCCTCATGATACA | Tet-pBam1, ET-recombination with pFM211 |
| 34 | IK252 | CAGCACATCCCCCTTTCGCCAGCTGGCGTAATAGCGAAGAGGCCCGCACCGGATTTTGAGACACAAGACGTC | |

TABLE 6

Characteristics of overexpressing M. gryphiswaldense strains.

| Strain | Geno-type | Crystal size | [%] size increase as to WT | Crystal number per cell | [%] increase in no. as to WT | [%] Cells w. >100 crystals | [%] iron content as to ΔRecA | Cell length [μm] |
|---|---|---|---|---|---|---|---|---|
| WT | 1 × MAI | 35.6 ± 13.0 | — | 34.3 ± 8.4 | — | 0 | — | — |
| ΔRecA | 1 × MAI | 36.2 ± 11.0 | 1.7 | 33.9 ± 10.3 | −1.2 | 0 | 100 | 4.44 ± 1.26 |
| ΔRecA + mamGFDC | 2 × mamGFDC | 44.9 ± 13.5 | 26.1 | 36.3 ± 12.4 | 5.8 | 0 | 7.4 ± 1.1 | |
| ΔRecA + mms6 1x | 2 × mms6 | 45.7 ± 14.2 | 28.4 | 46.5 ± 14.3 | 35.6 | 0 | 14.9 ± 2.9 | 4.53 ± 1.59 |
| ΔRecA + mamGFDC/ mms6 | 2 × mms6 2 × mamGFDC | 45.1 ± 12.2 | 26.7 | 45.1 ± 14.3 | 31.5 | 0 | 14.1 ± 1.9 | |

TABLE 6-continued

Characteristics of overexpressing M. gryphiswaldense strains.

| Strain | Geno-type | Crystal size | [%] size increase as to WT | Crystal number per cell | [%] increase in no. as to WT | [%] Cells w. >100 crystals | [%] iron content as to ΔRecA | Cell length [μm] |
|---|---|---|---|---|---|---|---|---|
| ΔRecA + mms6 2× | 3 × mms6 | 47.9 ± 12.8 | 34.6 | 54.3 ± 29.9 | 58.3 | 9.3 | 34.8 ± 2.5 | 4.56 ± 1.46 |
| ΔRecA + mms6 3× | 4 × mms6 | 44.4 ± 13.2 | 24.7 | 57.8 ± 26.9 | 68.5 | 7.8 | 38.8 ± 2.5 | 5.10 ± 1.95 |
| ΔRecA + mms6 4× | 5 × mms6 | 41.9 ± 12.0 | 17.7 | 46.0 ± 14.8 | 34.1 | 0 |  | 5.30 ± 1.70 |
| ΔRecA + mamAB 1× | 2 × mamAB | 34.0 ± 17.6 | −4.5 | 73.4 ± 43.1 | 114.0 | 21.9 | 0.4 ± 0.5 | 4.81 ± 1.82 |
| ΔRecA + mamAB 2× | 3 × mamAB |  |  |  |  |  | 9.4 ± 0.5 | 5.98 ± 2.58 |
| ΔRecA + ABG6X | 2 × mamGFDC 2 × mms6 2 × mamAB 2 × mamXY | 38.7 ± 11.9 | 8.7 | 74.5 ± 34.9 | 117.2 | 28.8 | 140.7 ± 2.4 |  |

The invention claimed is:

1. A recombinant isolated host cell, comprising in its genome:
   (i) a gene expression cassette capable of being expressed in the host cell, the gene expression cassette encoding a nucleic acid sequence encompassing the full-length sequence of the mamAB operon of a magnetotactic alpha-proteobacterium;
   (ii) a gene expression cassette capable of being expressed in the host cell, the gene expression cassette encoding a nucleic acid sequence encompassing the full-length sequence of the mamGDFC operon of a magnetotactic alpha-proteobacterium; and
   (iii) a gene expression cassette capable of being expressed in the host cell, the gene expression cassette encoding a nucleic acid sequence encompassing the full-length sequence of the mms6 operon of a magnetotactic alpha-proteobacterium;
   wherein the recombinant isolated host cell, upon expression of the gene expression cassettes in their entirety, is capable of producing magnetic nanoparticles, wherein the recombinant isolated host cell allows for heterologous expression of the gene cassettes in their entirety.

2. The recombinant isolated host cell of claim 1, further comprising:
   (iv) a gene expression cassette capable of being expressed in the host cell, the gene expression cassette encoding a nucleic acid sequence encompassing the full-length sequence of the mamXY operon of a magnetotactic alpha-proteobacterium; or (v) a gene expression cassette capable of being expressed in the host cell, the gene expression cassette encoding a nucleic acid sequence encompassing the full-length sequence of the feoAB1 operon of a magnetotactic alpha-proteobacterium; or (vi) both (iv) and (v).

3. The recombinant isolated host cell of claim 1, wherein the magnetotactic alpha-proteobacterium is a *Magnetospirillum* species.

4. The recombinant isolated host cell of claim 1, wherein the gene expression cassettes are stably integrated into the host cell's genome.

5. The recombinant isolated host cell of claim 1 wherein the magnetic nanoparticles are magnetosomes.

6. The recombinant isolated host cell of claim 1, wherein any one or more of the gene expression cassettes are under the control of their respective endogenous regulatory sequences.

7. The recombinant isolated host cell of claim 1, wherein the host cell comprises two or more copies of any one or more of the gene expression cassettes.

8. The recombinant isolated host cell of claim 1, wherein the host cell is a prokaryotic cell.

9. The recombinant isolated host cell of claim 8, wherein the host cell is *Rhodospirillum rubrum*.

10. Method for the production of a recombinant isolated host cell as defined in claim 1, the method comprising the transfer of the gene expression cassettes into the host cell by means of genetic transposition, and in particular comprising a modular transfer of the gene expression cassettes.

11. A method of making magnetic nanoparticles, comprising culturing the recombinant isolated host cell according to claim 1.

12. The method of claim 11, wherein said magnetic nanoparticles are suitable for application in magnetogenetics or biomedical imaging.

13. The recombinant isolated host cell of claim 2, wherein the magnetotactic alpha-proteobacterium is a *Magnetospirillum* species, and optionally is *Magnetospirillum gryphiswaldense*.

14. The recombinant isolated host cell of claim 2, wherein any one or more of the gene expression cassettes are under the control of their respective endogenous regulatory sequences.

15. The recombinant isolated host cell of claim 2, wherein the host cell comprises two or more copies of any one or more of the gene expression cassettes.

16. The recombinant isolated host cell of claim 2, wherein any one or more of the gene expression cassettes represent heterologous nucleic acid sequences.

17. Method for the production of a recombinant isolated host cell as defined in claim 2, the method comprising the transfer of the gene expression cassettes into the host cell by means of genetic transposition, and in particular comprising a modular transfer of the gene expression cassettes.

18. The recombinant isolated host cell of claim 3, wherein the magnetotactic alpha-proteobacterium is *Magnetospirillum* gryphiswaldense.

19. The recombinant isolated host cell of claim 5, wherein the magnetic nanoparticles are magnetosomes consisting of magnetite.

20. The recombinant isolated host cell of claim 8, wherein the host cell is an alphaproteobacterium.

21. The recombinant isolated host cell of claim 13, wherein the magnetotactic alphaproteobacterium is *Magnetospirillum gryphiswaldense*.

22. The recombinant isolated host cell of claim 2, comprising gene expression cassettes (i) to (iv).

23. The recombinant isolated host cell of claim 22, wherein the gene expression cassettes all encompass the full-length sequences of the respective operons; and wherein the total length of the gene expression cassettes comprised in the genome is less than 35 kb.

* * * * *

SEQUENCE LISTING

```
<160> NUMBER OF SEQ ID NOS: 37

<210> SEQ ID NO 1
<211> LENGTH: 73
<212> TYPE: DNA
<213> ORGANISM: artificial sequence
<220> FEATURE:
<223> OTHER INFORMATION: oligonucleotide primer Man-tps5

<400> SEQUENCE: 1
aattcgcacg gactatagca acgaatcgag gtcggttgac aagccataaa tcagaagaac      60
tcgtcaagaa ggc                                                        73

<210> SEQ ID NO 2
<211> LENGTH: 74
<212> TYPE: DNA
<213> ORGANISM: artificial sequence
<220> FEATURE:
<223> OTHER INFORMATION: oligonucleotide primer Man-tps3

<400> SEQUENCE: 2
gaacgaagat gagacagaaa tccgtggcgc cgagcgtaag catccggtga gaacctcatt      60
ccctcatgat acag                                                       74

<210> SEQ ID NO 3
<211> LENGTH: 71
<212> TYPE: DNA
<213> ORGANISM: artificial sequence
<220> FEATURE:
<223> OTHER INFORMATION: oligonucleotide primer mamGFC3

<400> SEQUENCE: 3
tatcatgagg gaatgaggtt ctcaccggat gcttacgctc ggcgccagag cacatcgggg      60
tgaatgacga c                                                          71

<210> SEQ ID NO 4
<211> LENGTH: 27
<212> TYPE: DNA
<213> ORGANISM: artificial sequence
<220> FEATURE:
<223> OTHER INFORMATION: oligonucleotide primer mamGFC5
```

```
<400> SEQUENCE: 4
cgctagctgc gggttattcg catttgc                                          27

<210> SEQ ID NO 5
<211> LENGTH: 68
<212> TYPE: DNA
<213> ORGANISM: artificial sequence
<220> FEATURE:
<223> OTHER INFORMATION: oligonucleotide primer spectMam3

<400> SEQUENCE: 5 tcaaacccg cgcagaggca aatgcgaata acccgcagct agcgttataa ttttttttaat     60 ctgttatt                                                               68

<210> SEQ ID NO 6
<211> LENGTH: 74
<212> TYPE: DNA
<213> ORGANISM: artificial sequence
<220> FEATURE:
<223> OTHER INFORMATION: oligonucleotide primer spectMam5

<400> SEQUENCE: 6
tgatccgcta tggtaagcgc atcatgtccg gatcccatgg cgttccgctc gtaacgtgac     60
tggcaagaga tatt                                                        74

<210> SEQ ID NO 7
<211> LENGTH: 54
<212> TYPE: DNA
<213> ORGANISM: artificial sequence
<220> FEATURE:
<223> OTHER INFORMATION: oligonucleotide primer mms6cm5

<400> SEQUENCE: 7
tactgcgatg agtggcaggg cggggcgtaa gcttacaatt tccattcgaa attc           54

<210> SEQ ID NO 8
<211> LENGTH: 25
<212> TYPE: DNA
<213> ORGANISM: artificial sequence
<220> FEATURE:
<223> OTHER INFORMATION: oligonucleotide primer mms6mam3

<400> SEQUENCE: 8
gtgcttcgct gtgtccacaa gaacc                                            25

<210> SEQ ID NO 9
<211> LENGTH: 42
<212> TYPE: DNA
<213> ORGANISM: artificial sequence
<220> FEATURE:
<223> OTHER INFORMATION: oligonucleotide primer cm-mms6-3

<400> SEQUENCE: 9
tggcgaatgg aaattgtaag cttacgcccc gccctgccac tc                         42

<210> SEQ ID NO 10
<211> LENGTH: 73
<212> TYPE: DNA
<213> ORGANISM: artificial sequence
<220> FEATURE:
<223> OTHER INFORMATION: oligonucleotide primer cm-mms6-5

<400> SEQUENCE: 10
```

```
tgatccgcta tggtaagcgc atcatgtccg gatcccatgg cgttccgctc gtcctggtgt    60
ccctgttgat acc                                                       73

<210> SEQ ID NO 11
<211> LENGTH: 64
<212> TYPE: DNA
<213> ORGANISM: artificial sequence
<220> FEATURE:
<223> OTHER INFORMATION: oligonucleotide primer IK097

<400> SEQUENCE: 11
tctagagggc cccaactttt tcgctttact agctcttagt tctccaataa attccctgcg    60
tcga                                                                 64

<210> SEQ ID NO 12
<211> LENGTH: 67
<212> TYPE: DNA
<213> ORGANISM: artificial sequence
<220> FEATURE:
<223> OTHER INFORMATION: oligonucleotide primer IK098

<400> SEQUENCE: 12
catatgctga tctccggcaa gtgtatgcac gattccctct ctgcccctta aaatcgacgc    60
agggaat                                                              67

<210> SEQ ID NO 13
<211> LENGTH: 23
<212> TYPE: DNA
<213> ORGANISM: artificial sequence
<220> FEATURE:
<223> OTHER INFORMATION: oligonucleotide primer IK107

<400> SEQUENCE: 13
catatgatca agggcatcgc ggg                                            23

<210> SEQ ID NO 14
<211> LENGTH: 26
<212> TYPE: DNA
<213> ORGANISM: artificial sequence
<220> FEATURE:
<223> OTHER INFORMATION: oligonucleotide primer IK101

<400> SEQUENCE: 14
ggtaccggcc aattcttccc tcagaa                                         26

<210> SEQ ID NO 15
<211> LENGTH: 21
<212> TYPE: DNA
<213> ORGANISM: artificial sequence
<220> FEATURE:
<223> OTHER INFORMATION: oligonucleotide primer IK102

<400> SEQUENCE: 15
ggtaccggag gcggaggcgg t                                              21

<210> SEQ ID NO 16
<211> LENGTH: 28
<212> TYPE: DNA
<213> ORGANISM: artificial sequence
<220> FEATURE:
<223> OTHER INFORMATION: oligonucleotide primer IK103

<400> SEQUENCE: 16
gaattcttac ttgtacagct cgtccatg                                       28
```

<210> SEQ ID NO 17
<211> LENGTH: 28
<212> TYPE: DNA
<213> ORGANISM: artificial sequence
<220> FEATURE:
<223> OTHER INFORMATION: oligonucleotide primer IK163

<400> SEQUENCE: 17
gaattcttag ttgtacagct cgtccatg                                           28

<210> SEQ ID NO 18
<211> LENGTH: 22
<212> TYPE: DNA
<213> ORGANISM: artificial sequence
<220> FEATURE:
<223> OTHER INFORMATION: oligonucleotide primer IK164

<400> SEQUENCE: 18
gagctcggca gcctcattta aa                                                 22

<210> SEQ ID NO 19
<211> LENGTH: 69
<212> TYPE: DNA
<213> ORGANISM: artificial sequence
<220> FEATURE:
<223> OTHER INFORMATION: oligonucleotide primer IK173

<400> SEQUENCE: 19
ccggaattgc cagctggggc gccctctggt aaggttggga agccctgcaa cgtataatat        60
ttgcccatg                                                                69

<210> SEQ ID NO 20
<211> LENGTH: 65
<212> TYPE: DNA
<213> ORGANISM: artificial sequence
<220> FEATURE:
<223> OTHER INFORMATION: oligonucleotide primer IK174

<400> SEQUENCE: 20
aggcgataga aggcgatgcg ctgcgaatcg ggagcggcga taccgtaaag cgatctcggc        60
ttgaa                                                                    65

<210> SEQ ID NO 21
<211> LENGTH: 75
<212> TYPE: DNA
<213> ORGANISM: artificial sequence
<220> FEATURE:
<223> OTHER INFORMATION: oligonucleotide primer IK208

<400> SEQUENCE: 21
cccggtaccc agcttttgtt ccctttagtg agggttaatt gcgcgcttgg cctcattccc        60
tcatgataca gagac                                                         75

<210> SEQ ID NO 22
<211> LENGTH: 69
<212> TYPE: DNA
<213> ORGANISM: artificial sequence
<220> FEATURE:
<223> OTHER INFORMATION: oligonucleotide primer IK209

<400> SEQUENCE: 22
ggcgttaccc aacttaatcg ccttgcagca catccccctt tcgccagctg tctcggcttg        60
aacgaattg                                                          69

<210> SEQ ID NO 23
<211> LENGTH: 18
<212> TYPE: DNA
<213> ORGANISM: artificial sequence
<220> FEATURE:
<223> OTHER INFORMATION: oligonucleotide primer IK213

<400> SEQUENCE: 23
gacgtcgagc cacggcgg                                                18

<210> SEQ ID NO 24
<211> LENGTH: 22
<212> TYPE: DNA
<213> ORGANISM: artificial sequence
<220> FEATURE:
<223> OTHER INFORMATION: oligonucleotide primer IK214

<400> SEQUENCE: 24
gggtccctca ggtcgaggtg gc                                           22

<210> SEQ ID NO 25
<211> LENGTH: 23
<212> TYPE: DNA
<213> ORGANISM: artificial sequence
<220> FEATURE:
<223> OTHER INFORMATION: oligonucleotide primer IK215

<400> SEQUENCE: 25
tctagactac aagaatgtcc cgc                                          23

<210> SEQ ID NO 26
<211> LENGTH: 21
<212> TYPE: DNA
<213> ORGANISM: artificial sequence
<220> FEATURE:
<223> OTHER INFORMATION: oligonucleotide primer IK216

<400> SEQUENCE: 26
gaattcggca tcctgatcgg t                                            21

<210> SEQ ID NO 27
<211> LENGTH: 21
<212> TYPE: DNA
<213> ORGANISM: artificial sequence
<220> FEATURE:
<223> OTHER INFORMATION: oligonucleotide primer IK217

<400> SEQUENCE: 27
catatgatgg caaaaaaccg g                                            21

<210> SEQ ID NO 28
<211> LENGTH: 32
<212> TYPE: DNA
<213> ORGANISM: artificial sequence
<220> FEATURE:
<223> OTHER INFORMATION: oligonucleotide primer IK218

<400> SEQUENCE: 28
ggcggtacct ttattcttat cttcagcatc ac                                32

<210> SEQ ID NO 29
<211> LENGTH: 70
<212> TYPE: DNA
<213> ORGANISM: artificial sequence

```
<220> FEATURE:
<223> OTHER INFORMATION: oligonucleotide primer IK235

<400> SEQUENCE: 29
gggtggagcg ggataatggc aaaaaaccgg cgtgatcgcg gcacggctaa atacattcaa      60
atatgtatcc                                                             70

<210> SEQ ID NO 30
<211> LENGTH: 68
<212> TYPE: DNA
<213> ORGANISM: artificial sequence
<220> FEATURE:
<223> OTHER INFORMATION: oligonucleotide primer IK236

<400> SEQUENCE: 30
ctatttattc ttatcttcag catcacattt cggcgatgaa caactacctt accaatgctt      60
aatcagtg                                                               68

<210> SEQ ID NO 31
<211> LENGTH: 68
<212> TYPE: DNA
<213> ORGANISM: artificial sequence
<220> FEATURE:
<223> OTHER INFORMATION: oligonucleotide primer IK239

<400> SEQUENCE: 31
cgccgcttgt gttctgtatc aagactggag aacgtttatg ccaactaaat acattcaaat      60
atgtatcc                                                               68

<210> SEQ ID NO 32
<211> LENGTH: 65
<212> TYPE: DNA
<213> ORGANISM: artificial sequence
<220> FEATURE:
<223> OTHER INFORMATION: oligonucleotide primer IK240

<400> SEQUENCE: 32
tcaaccatcg atgttagggt ctgagttcgc cctcttaccg gcaggttacc aatgcttaat      60
cagtg                                                                  65

<210> SEQ ID NO 33
<211> LENGTH: 70
<212> TYPE: DNA
<213> ORGANISM: artificial sequence
<220> FEATURE:
<223> OTHER INFORMATION: oligonucleotide primer IK251

<400> SEQUENCE: 33
aaaccgccca gtctagctat cgccatgtaa gcccactgca agctacctgc cctcattccc      60
tcatgataca                                                             70

<210> SEQ ID NO 34
<211> LENGTH: 72
<212> TYPE: DNA
<213> ORGANISM: artificial sequence
<220> FEATURE:
<223> OTHER INFORMATION: oligonucleotide primer IK252

<400> SEQUENCE: 34
cagcacatcc ccctttcgcc agctggcgta atagcgaaga ggcccgcacc ggattttgag      60
acacaagacg tc                                                          72
```

<210> SEQ ID NO 35
<211> LENGTH: 26564
<212> TYPE: DNA
<213> ORGANISM: artificial sequence
<220> FEATURE:
<223> OTHER INFORMATION: gene expression cassette comprising the mamAB, mamGDFC, and mms6 operons of Magnetosprillum gryphiswaldense

<400> SEQUENCE: 35

| | | | | | |
|---|---|---|---|---|---|
| acaggttggc | tgataagtcc | ccggtcttca | cgctgccgca | agcactcagg | gcgcaagggc | 60 |
| tgctaaagga | agcggaacac | gtagaaagcc | agtccgcaga | ggcggtgctg | accccggatg | 120 |
| aatgtcagct | actgggctat | ctggacaagg | gaaaacgcaa | gcgcaaagag | aaagcaggta | 180 |
| gcttgcagtg | ggcttacatg | gcgatagcta | gactgggcgg | ttttatggac | agcaagcgaa | 240 |
| ccggaattgc | cagctggggc | gccctctggt | aaggttggga | agccctgcaa | agtaaactgg | 300 |
| atggctttct | tgccgccaag | gatctgatgg | cgcagggggat | caagatctga | tcaagagaca | 360 |
| ggatgaggat | cgtttcgcat | gattgaacaa | gatggattgc | acgcaggttc | tccggccgct | 420 |
| tgggtggaga | ggctattcgg | ctatgactgg | gcacaacaga | caatcggctg | ctctgatgcc | 480 |
| gccgtgttcc | ggctgtcaga | gcaggggcgc | ccggttcttt | ttgtcaagac | cgacctgtcc | 540 |
| ggtgccctga | atgaactgca | ggacgaggca | gcgcggctat | cgtggctggc | cacgacgggc | 600 |
| gttccttgcg | cagctgtgct | cgacgttgtc | actgaagcgg | gaagggactg | gctgctattg | 660 |
| ggcgaagtgc | cggggcagga | tctcctgtca | tctcaccttg | ctcctgccga | gaaagtatcc | 720 |
| atcatggctg | atgcaatgcg | gcggctgcat | acgcttgatc | cggctacctg | cccattcgac | 780 |
| caccaagcga | aacatcgcat | cgagcgagca | cgtactcgga | tggaagccgg | tcttgtcgat | 840 |
| caggatgatc | tggacgaaga | gcatcagggg | ctcgcgccag | ccgaactgtt | cgccaggctc | 900 |
| aaggcgcaca | tgcccgacgg | cgaggatctc | gtcgtgaccc | atggcgatgc | ctgcttgccg | 960 |
| aatatcatgg | tggaaaatgg | ccgcttttct | ggattcatcg | actgtggccg | gctgggtgtg | 1020 |
| gcggaccgct | atcaggacat | agcgttggct | acccgtgata | ttgctgaaga | gcttggcggc | 1080 |
| gaatgggctg | accgcttcct | cgtgctttac | ggtatcgccg | ctcccgattc | gcagcgcatc | 1140 |
| gccttctatc | gccttcttga | cgagttcttc | tgatttatgg | cttgtcaacc | gacctcgatt | 1200 |
| cgttgcctat | agtccgtgcg | aattggaggt | gaattgtgac | gggaatggaa | cctggcagat | 1260 |
| cagaagttga | ggggcaccag | cgcaacgccc | tttatttatt | gtcggcgttg | tgcatggttt | 1320 |
| tcatgactct | cgtcgttgct | attcagccgc | ttttttttgcg | aaacgttctt | aatatcccct | 1380 |
| tcgagactgc | cggggcagtc | aatgccaatg | tgcaggtggt | gaccgaggtc | cttgatcttt | 1440 |
| tcatctttgc | ctatcttggt | tacctgtcag | atcgcattgg | ccgggtccgg | atcatcgtgg | 1500 |
| cgggcttttct | cgtcgctgcg | gtcggcgctg | tgatcgcgcc | gctaagtccc | tgggttggcg | 1560 |
| gagcctccat | tggggcgctg | gtggtctact | acgtttcgcg | ggtcatcatg | tctgcgggca | 1620 |
| gcggtgctgt | gtggccgcaa | ttgtcggccc | tggccggtga | tttcagtgac | gacagcaacc | 1680 |
| gggctcggct | gctgtccaat | accgccttta | tgatggcgtt | cggcgtgacg | ctggtctatg | 1740 |
| cggtcctgat | gcagatccct | ggccatgcgg | gtattacggt | gaccatgttg | ctgactgcgg | 1800 |
| ccatttccgt | ggccggtgct | tggctggcgc | gcaaatttct | cgtggatgtg | gctccgcgca | 1860 |
| ccgtcgagac | ctctgtcccc | tggcgggccg | tttgggatct | ggtgaaggcg | gagccgcgcc | 1920 |
| tgcggctggc | ctttgcaagt | tcattgttcg | ctcgaagcga | tatggtgttt | gtcggactgt | 1980 |
| tcctcatgct | gtggttcatc | tacttcgccg | acctcgtaaa | ggtcgggcag | gcggaggcgg | 2040 |

-continued

```
ctgcaagggc gggcatgttg atcggattga tgggggcggt ggtcatgctc tcgattccgg    2100
tctggcgctc gtttatcgag cgtttcgggc gcattcaggc cgtttttattg gggatgatgc   2160
tatccgccct tggatttata atgctcggat ttgtggtcaa tccatttgac ggatttattg    2220
tgttttccat tctgttggtt tcggccgggc aagctggttg ctttgttgct ccgcaaatac    2280
taaccgttga tcatgcacca aaagacttgc tcggttctgt tctcggcgca tttaatgtta    2340
ttgggtgcct gggaattatt ttttttgttc agattggtgg gttttttattt gattacattg   2400
gccctcctgc gccttttatc tttacgggcg ttggaaattt gattatatca gcatatgcgt    2460
tgcgtcttgt gaaaagtgag gcgcgtgggg ttggcggggg taacaccccca ggggatgacc   2520
aagtggccta gcgccgcttg tgttctgtat caagactgga gaacgtttat gccaagcgtg    2580
attttcgggc tgctggcgct tgccattgga ttgctgggggc tgacggcgtg gtggtggtcg   2640
gtgaccgagt ttctgcgtgg tgcggtgccg gtggctctga tcatcttcgg cttggttgcg    2700
ctggccgcag gggtccagtc ggtgcgagtg cctcctgccg gtaagagggc gaactcagac    2760
cctaacatcg atggttgatg accatgttca atggtgatgt ggaagacggt ggccgttcca    2820
atgtctcttg cggcaaagac ctgaagcgct acctgatgct catgggcgtt gtcgccctgg    2880
tcgtcctgtt cggcgcgttc atctatcggc agtcctcggg cggtcttcgc ctgggcgcca    2940
tgatggagca gatgacaggc gcacgcggcg cagtgaacgt tcctgcgcag catggcgcgc    3000
cgtcggcggt ggtcgatccg gcgatgtcgg ttccggctag ggcgcgcgtg gcgccgccct    3060
cggctgccgg tgctatcgcg accttccctc cggtggtgga ttttggaccg gccccggtgg    3120
tgagcggtgg cccgttcacc ggcgtcgtaa cccttctgcg caatagcgtg gttagcgtga    3180
ccgcctcctc atccggcggc caagtcatgc ccgatcccctt ggggttggtc aatcccgacg    3240
gtcttccccg tttcgccaat cccaccactc ggtcggtgga gaatatcggc accggcgtta    3300
tcgtccgcaa tgacggcttc atcgtcacca attaccatgt ggtgcgcggg gccaattcgg    3360
tgtacgtcac cgtaaaggac gatgtgggtt cgatccgcta ttccggcgag atcgtcaaga    3420
tggatgaggc gctggatctc gctttgctca agatcacccc caaggtccag cttaccgctg    3480
cggttctggg cgacagcgat gcggtgaacg tcgctgacga ggtgatcgcc atcgggactc    3540
ccttcggcct ggatatgacc gtcagccgcg gcatcatttc cgccaagcgc aaaaccatgg    3600
tcatcgaagg gatgacgcac tccaacctgc tgcagaccga cgcggcgatc aatcagggta    3660
attccggcgg tccactggtg gcggccaacg gcacggtcgt cggcatcaat acggcaatct    3720
ataccccaa tggtgcgttt gctgggatcg gctttgccgt gcccagcaat caggcccgcc    3780
ttttcgcact ggatgaagtg ggctggttgc cgacatccac cgccgagggg ccggccatgg    3840
gactggtggc catgcagcgg cccatggggtg tcggtgtcgg tgcggcaggt ccggtgattg    3900
ctgcgggtac tccgtcgccg catgtggatg gccgccagaa catggattgc agcaattgtc    3960
acgatattat tcccgccggt aatggttttcc aggcgccgat gatgcccgtg gctgctcccg    4020
tgccgccacc gccgattccc gcgaatgccg tatcacctca caccgatggt cggcaaaaca    4080
tgacctgcaa cacatgccac cagttcgtcg gtggtgcggc agccggtccg atcgcctttg    4140
gccaaccgat gatgcccatt gccgcaccgc agcaacccgc accggcgatt cgggccaatg    4200
ccgccaaccc tcacacggac ggtcggcaga acatgaactg cgccagctgc catcagatca    4260
tcggctccgt cggcgcggct cccatcgccg cgccggagc tggggggcgcc tatcgctttt    4320
cccagccgcc agggagcctg gccatcaata tccaggggcc gcgcggtggg caggggctg    4380
ttgccggaag tggtggtagc cgggcctcgc tcctgggggc ggctttgacc cccttgaccc    4440
```

```
agcgtctggg gctgcaggct aacctgcctg ctggtcgcgg ggtgttcgtg aacggcgtta      4500
ctcccaatac ccctgccgca tctgcggggc tgcgtcctgg cgacgttatc ctcaaagtcg      4560
atggccgtcc cgtgcatcaa cccgaggaag tggcagccat catggccgag atgcccaacg      4620
gtcgttcggt gcgaatcgga gtcctgcgtg ccggcgatgt gagcaacatg tctcttgtca      4680
ccggcccatc gggtctggcg gctgccgtgg ttcaggcacc tacggctccg gtcgtgatgg      4740
cggggggcgc tcccacggtt cctggcgttc agcctgttat tccgaaggta ccgaccgagt      4800
tcaactggct ggggatggag atcgagactt ttatggctcc gcagccggtg gtcggcatgc      4860
cgggcgctac tcctgttgcc gggggggggta aaggggctca ggtggccgag gtgttggccg      4920
gatcacgcgc cgcagtggcg gggcttcagg ccaatgatct tatcatcgag gtaaataatc      4980
ggccggtgac aagccccgct cggcttgatg ccgccattaa ggcggcgacg gccgccgggc      5040
agcagatttt gctcaaggtc catcgcaatg ccaagagtt ctggattgtt ctttgagggt      5100
ggagcgggat aatggcaaaa aaccggcgtg atcgcggcac ggaccttcct ggcgatggcg      5160
atcaaaagat ctcgacgggg ccggagattg tttcggtgac ggtccatccc tcgccgaacc      5220
ttgctgcggc ggccaagccg gtgcagggcg acatttgggc tagcttgctt gaaagttcgc      5280
cgtggtcagc taatcaaggg gggctggtcg agacggcaca acctccttcc gcccccattc      5340
gttcccagga ccctgtgccg gttgccgatc tggtcaaccg ttggtcacag ccgatctggc      5400
gaacagcccc gctggccggg aatgcagaat cctctgagga gggcgtcgta gctccttcgc      5460
tgacgcagtc ggattctgtg cttgccgtgt ctgatctggt gattgatgtc cagccggaaa      5520
cgaatgccga ggttgaagtt tccatcgagc cggaacccgc gctggtcgag ccggtgatcg      5580
agatcgaagc cgaagccgcc gaagtcgagc cggaacctgc cccggttgcc gatctggtca      5640
accgttgggc acagccgatc tggcgaacag ccccgctggc cgggaatgca gaatcctctg      5700
aggagggcgt cgtagctcct tcgctgacgc agtcggattc tgtgcttgcc gtgtctgatc      5760
tggtgattga tgtccagccg gaagcgaatg ccgaggttga agtttccatc gagccggaac      5820
ccgcgctggt cgagccggtg atcgagatcg aagccgaagc cgccgaagtc gagccggaac      5880
ccgcgccggt tgagccggcg atcgagatcg aagccatcag ggttgaactg gaacctgtaa      5940
ttatcgacca ggtagtcgag ttggtgaccg agttcgagta ttcgcaggcg gagagcgttg      6000
catcagcgga tttgatcgct aatcccgcac ctgctgaaag ctcccgtctt gccgagcttc      6060
tggatgaggc tgctgctatt gctgctcccg ccgttgctgt ggcggtcgaa gccacccgcc      6120
agcctaacaa gatcaccgcg tcagttaaga agcgcgcccc ggttcaggaa gttcccgtgg      6180
aagaccttct gggggggatt ttcggcgtcg ccggatcggc ggtgcggggt gtgttcacta      6240
ttggcggcg attcgtcgat ggagtggtca agggaggccg cctcgttgga agcaatgtgg      6300
tcgccgggac gcgccggttg gcgcaaacta tcgaggtaag ttgcggtagt tgttcatcgc      6360
cgaaatgtga tgctgaagat aagaataaat agagacctgt ggattgatct gttagcacgc      6420
gaacggagtg acaaaatgag tgaaggtgaa ggccaggcca agaacaggtt gttccttggc      6480
atcgaccttg ggacttccca taccgcggtg atgacgagcc ggggaaagaa gttcctgctg      6540
aagtcagtgg ttggataccc gaaggatgtc attggcttga agctgctcgg tcgcccctat      6600
gtggttggcg atgaagcctt cgagatgcgc tcctatctgg atctccgcta tccgctccag      6660
gacggtgtgc tcagcgagat cagtgaccgc gacatcgagg tggcgcgtca cctgctgacc      6720
catgtggtga agtcggcgga gccgggcgcc aacgacgaga tttgcgcggt catcggcgtg      6780
```

```
ccggcccgag cgtcgggagc caacaaggcg ctgttgctta agatggccca agaagtggtt   6840
cacaccgcgc tggtggtatc cgagccgttc atggtcggct atggcttgga caagctgaac   6900
aataccatca ttgtcgatat cggcgccggg accacggata tctgcgccct aaagggcacc   6960
gtgcccggac ccgaggatca ggtgaccctg accaaggcgg caattatct ggacgagcgc    7020 ctgcagaacg ccattttgga acgccatccc gaattgcaaa tgaatacgaa tgtggcctgc   7080
gcggtgaaag agcaatttc attcgtcggc gcgcgcggcg aagcagccac cttcgagttc     7140
cgcgccgccg gcaagcccgt gcgttgcgat gtgaccgaat cggtaaagat cgcctgcgaa   7200
gcgctgatgc ccgatatcat tgaaagcatc gagattttgt tgcggtcctt ccagccggaa   7260
tatcaggcca ccgtgctgca aaatatcgta tttgccggcg gcggctcgcg gattcgcggt   7320
ttggcagcct atgtgaaaga taaactgcgc ccgttcggca atgcggacgt gacttgcgtc   7380
aaggacccga cttttgatgg ttgccggggc gctctgcggc tggcagaaga acttccgccc   7440
cagtattggt gtcagcttgg tgacgtttcc ggtcagtgat gggggatgtc attttggttg   7500
gcgaagatgc gtggctgtcc aggacattgg tatggtaaga gtgatcggat cgttggtgtt   7560
cggcggcttg atcctgctgc tggcatcgtc aacgcccat atggtggaaa cccgatttgg     7620
gccactgata atgcttgcgc cacatttcgt ggttcttggc attacgtttt tcttggtttt   7680
cgccattggg attgtgttgg tgtttgcgaa tgttatgaaa cggagcaagc ataaactgcc   7740
tgggaaaaac atcgtcatta agcgctgacg ttccatgctc cgtcggagct gggccggggc   7800
tttggagtag gtaaggatga ggaagagcgg ttgcgcggtc tgcagcagga gcatcggctg   7860
ggttggcctg gcggtgagta ccgtgctcat ggtgatgaag gcattcgtcg gcctgatcgg   7920
tggatcgcag gctatgctcg ccgatgccat gtattcgctg aaggacatgc tgaacgccct   7980
gatggtgatt attgggacca ccattccag caagccgctg atgccgagc atccctacgg      8040 ccatggcaag gtcgaattca tcctgtccat ggtggtcagc gtggtcttca tcgtgctgac   8100
cggctacctg ctggtccatg ccgtccagat cctgttggac gagagcctgc accggacgcc   8160
acacctgatc gtgctgtggg cggccctggt ttccatcggc gtcaatgtgg gcatgtattt   8220
ctattcccgc tgtgtcgcca ttgagactaa cagccccctc atcaagacca tggccaagca   8280
tcaccatggc gacgccaccg cctcgggcgc ggtcgcgctg ggtatcatcg gcgcccatta   8340
tctcaatatg ccctggattg atccgcggt cgctctgtgg gagaccatcg acctgcttct   8400
gctgggtaag gtcgtcttca tggatgccta tcgtgggctg atggatcaca ccgcgggtga   8460
ggcggtgcag aaccggattg ttgaggcggc ggagcgcgtt cctggggtca ggggcgtcat   8520
ccatctgcgg gctcgctatg tgggccaaga catctgggcc gacatgatta ttggcgtcga   8580
tcccgagaac accgtggaac aggcgcatga aatttgcgag gcggtgcagg ccgctgtctg   8640
cggaaagata cgccgcatcg aatccctgca tgtcagcgca gaagcgcgcg aaatcggcga   8700
tacgaccaag ccgagtttct ccgatcagcc gctgagtttc gacgaggtca tgctgtccaa   8760
ggtggataac taggtggttg gatttatcac cctcgctgtg ttcatcgcga cgttcgccgt   8820
aatctatcgg tgggcggagg gcagccatct ggccgttttg gccggagcag cggtgttggt   8880
ggtgattgga accatcagcg gcacctacac cccgcgtatg gccgtgcagt cgatttattt   8940
cgagacccct tgcgttgatct tcggcatggc tgccatctcc gctcttttgg cccgatccgg   9000
cgtctatgcc tatttggcgg ccgggacggc ggaattgtcg cagggccaag gcgctggat    9060 tctggtgatg atggctttgg tgacctacgg gatttctttg gccagtaaca gtcttatcac   9120
agtggccgta gtcgttccgg ttacgctgac cgtatgtttc cgcactggaa ttgatccggt   9180
```

```
acccgtgatc attgctgaga ttatcgccgc caatctgggc ggttcctcga ccatgatcgg    9240
cgattttccc aatatgatcc tggcctcggc aggcaagctt catttcaatg atttcatcgg    9300
tggaatgatg ccggcctgtc tgatcttgct ggcggtgact ttcttgtttt tcgagtaccg    9360
ccagggcgac tggaagaagg cggaaattcc cgtggattta gcttgggtta gaggcgagca    9420
gctacggtac agcgatatcg accatcggct cctgcgctat gggctgatca ttttttttcat   9480 taccgtcatt gggttggttc tggcgggacc gctgaaggtt cggccgggct ggatcgcctt    9540
tgtcgccggt ctcactgcgc tggcgctggg gcgcttcaag gacgaggaat tcttttccgc    9600
ctgcggcgga agcgatatct tattctttgg cggattgttc gtgatggtgg gagcgttgac    9660
ctcggttggg attctcgatt gggccgtggc ttggcttgaa ggagttaccg ccgggcatga    9720
ccgcgtaaga gccattctgc tgatgtggat ggcggcgggc gtaaccattt tcgtcggcgg    9780
cggcacttcg gctgcggttt tcgccccggt ggcggcgacg cttcgcctgg acggcgatgg    9840
acaggcggct tggtgggcgc tggcccttgg catcatggcc ggctcgtgtg ccgcgctatc    9900
gggcgccacc gccggtgcgt tggccatgaa ccaatattcc ggcttcgtga agcggcaccc    9960
ggaattggct tcggctgccg ccgcgggatt gcaattcacc catcgggaat atgtccgttg   10020
gggattgccg ctgatgggga tttttttggt gttgtcgacc gtgtacatcg ccgttctcgc   10080
aggatgaccg atgacgacag gaactcgaat gaacgtggaa agcggccatg attgaaattg   10140
gcgagaccat gggtgatcag cccaccaaca aaatcgtctt ttgcgagcgg tcgtggaaag   10200
cgcctgtctc catcctggcg ttcctgatcc tagtgacttt cgcctggggg gcctatctcc   10260
tcgacaacta cgacgaggac gactacttcc gtggtagcga cgatatgtcg gtcggccaat   10320
tcctggtccg caacgtcgcc atgcctgatg tgcagcggct gtactataca gtaccaccgg   10380
cggtggtcgg tgtgggggc ggcggcgtca atgccggtcc cgtcgcttcg ggtgccatcg    10440
ttggcgccaa tggctatgtc attacgaccc tgcattccgt cgccaatgtg ccggacatca   10500
cggtccaggt tgccacctct gctggaatcc gtcggtttcc cgcccaggtg gtcaagacca   10560
ttccgggcca taatctcgcg ctgctgaagt tgcagacgac cgagaagttc ttgcatttcc   10620
gcatggcaaa cattcaaacc gtggtccccg gccagcaggt tttcgccttc ggtcggaaca   10680
tggccggtgc gcctctggta cggcagggca tggtgcaatc ctccgatgct ccgctggcgg   10740
tggggaccac tcagatcacc catctgctgc gttccgacgc ggtctatagc tgggagcaga   10800
ccggcgggcc tctggtcaat gctcagggtg atctggtcgg tatcaacatt gccgcaaccg   10860
gtcccaccgg caaggtcgaa ggctttaccg ttcctgctca ggtgatcgtc tcccatctta   10920
aggacgtcgt gcgattcaag accggtggcg ccgcgggagt tgctcctccc gcggcccaaa   10980
ctgtggccat gggatcctct agctggtggt ctaaggccaa agcggtggtc ggagggccga   11040
ccgccgtacc gggaatgggc atgaatgtgg tgcaagggac ggtgacgacc gggattccct   11100
cgggcatgcc gtttgtcgat accgaccatg tgggagggc caagatcggc ggatattcca   11160
tcgccgatat tctcggccta ggcatgcttg ccctggcggc cggtgtcacg ggtggcatga   11220
tgaccatggg cggcggagtg cttcaggtcg ctggcatgat ggtcttcttc ggctatggca   11280
tgtatctgat ccgccggtg gtcttcctga ccaatgtcgt ggtctatggc gcagcggcgc   11340
ttcgcaatga taaggcccaa ctggttcagt gggacaaggt gaaaccgctg atcccttggg   11400
gcgtcgctgg cgtggtcatc ggttatttca tcggtaacgc catcggagat tccgtggtgg   11460
gcgtgctgct tggtctcttc gccctgatca tggcaggcaa ggcggtgttg gaaattctgc   11520
```

```
aacccaatgc gggggaggat acggctgaag ccattgctgc cgccgaggct ggcgatgaga   11580
tggacgaact gatggctctg gcggaaggaa caaccaggcc caagaccagc ggcattgctt   11640
tgccagaggg gccgacccgt tcagcggtgc tggggctgcc catgggcctg ttcagcggca   11700
ttctcgggat cagcggcggc gtcatcgagg ttccgttgca gcgttatatt gggcggatca   11760
gtctgcagaa cgccattgcc aacagttcgg tcctggtgtt ctgggcctcg gtcgccggtt   11820
cagtggtagc cttttattcat ggcggcagca ccggtcttat tcattgggag ctccggtaa   11880 cattggcgct ggtgatgatc ccaggtgctt atgttggcgg cattctcggc gctcggttga   11940
tgcgggtgtt gcctgtccgg gtgcttaagg gtatctatgc ggcaaccatg gccgctatcg   12000
ccatcaagat gctgacaacg gtgtgatgga tatggttttg ggattagccg ggaatgaata   12060
gcaaactcgt cctgctggtg gtgggtgtcg tttttgcact ggtgcttgtc attgggcggc   12120 agggggggcgt cgttgctcct cagtcgatca gcgtttcgcc tcagatgtcg actgcggctc   12180
cggtcgctgc cccgattgct tttccgcagg cgaccaatgt ggccatggcg gtggagccca   12240
tggccgcggc gggtggtacc gtggctgcaa tggagtcgcc cttgcccaat ttcgttccga   12300
gcaatctcaa ggtctttgaa ggccattggc agggcatgga cggacgtctg atgaccgagg   12360
aactggcccg aaagttgaac tatcctcgtg gagtgcaggg cgttctgttg ggcgaggtta   12420
ctttgaacgc ggcgttcagc ggtctgttgg ggggggatgt cgtcgttcgg attgatgaca   12480
ctccagtcac caatatggaa aatttccagg cagctacccg caatgtggcg aaccggtccg   12540
aggcgcggat cagcgtgatc cgtaaggaca accgtcccgg caccccggtc ttgcgcaaac   12600
tgaccgtggt tttgcgcgcg gccgaaggcg gtttgggctt tgcccagttg gaaggcgccc   12660
ccatgatcct tccgggcgat cctcggcccc atggatatcg cggcgcctgc accgattgcc   12720
atccggtagg ccagggattc gaattgtcgc ccgatcctga tctcatcagc ctgccgcctt   12780
cggccataac gcgtgatgcg gttacccggg gcgtcagtcc ccacgaagtt cgtggcccgt   12840
gcgaagcttg ccacgtgata aattagccag agccaccgga ttgggatttt ggagaacagt   12900
atgtctagca agccgtcgaa tatgcttgat gaagttaccc tgtatactca ctacggccta   12960
tccgtggcga agaagctcgg tgcgaatatg gtcgatgctt ccggtcggc cttttcggtc   13020 aatgatgaca ttcgtcaggt gtattaccgc gacaagggca tctctcacgc caaagccggt   13080
cgttattccg aggcagtggt gatgctcgag caggtttacg atgccgatgc cttcgacgtg   13140
gaagtggcgc tgcatttggg aatcgcctac gttaagaccg gggccgttga tcgcggcacc   13200
gagttgcttg agcgctccat cgccgatgcg cctgacaaca tcaaggtcgc gaccgtcctt   13260
ggcctgacct atgtgcaggt gcaaaaatat gatttggccg tgcctctact ggtcaaggtg   13320
gcggaagcca atccgtgaa tttcaatgtc cgcttccgtc tcggggtggc gctggataat   13380
ctggcccgct ttgacgaagc catcgacagt ttcaagatcg ctttgggct gcgtcccaat   13440 gaaggcaagg tgcatcgcgc aatcgcgtac agctacgagc agatgggctc gcacgaagag   13500
gctttgccgc atttttaagaa ggccaatgaa ctcgatgaac gttcggccgt ctaagcagtc   13560
gatgtagaag gtctcattga gatgacgata gcaacgaggc ggatatggca gtaagcgatg   13620
cggacgccag ttcggtcgat aaggtcgaat ccattaccct acaacgggtc aagcagtcgg   13680
aggaactgct ggcccaattg tatgtggttg aggaatcgcc ccggcgcatg ggacggggc   13740 cggtgcaact catgctggcc atctcggtgc tgtcgctggt tgccttcatc accaccttgc   13800
tgatgcgcta taacgccttt gtcaccatgt acgaggatgc ccaggccaag cgctccaatt   13860
tcgaggtcat gattcaacgc cgcgacaatc tgtttggcaa tttggtcaag ttgacgctga   13920
```

```
atcatgccgc tttggaacac tccatcttct ctcacacttc cgacaagcgt aaggagtccg    13980
tggaagccgg caagggcggc ccgatcggtt cggccatcga gcaattgatg aagcagggcg    14040
gaatcggaaa attgctgggc gatggcgggg ccggcaaggc cctgttgggg gccgatggtg    14100
gtttcggcaa cgcgctgggg cggctgatgg ccattgtcga gcagtatccc accgttcagt    14160
cggcggatac ctacaagcat atgatgacct cgctggtgga tatggaagac cggatcgcca    14220
gcaagaggga ggaatttaac gcatctgccg cgacctataa tgtggcaatc accaagtggc    14280
cgtgggatta tctggcaatg atcaccgggt tcaagcgcgt ggagtatttc acgaaaagc    14340
ctgcaggcga cacgccgatc attacgccac agattttcca ggaactactg cctctcaccc    14400
attcgcagga atccaagaat tgatttggac agcagtgatc aagggaagtg ccttgatgac    14460
ctttgttcag ggcgccatgg ctctggtgga caaggtattt ggcgaggaaa ttctgccgca    14520
ccgcatctat agcagcggtg aagcggcgca gttgctggga atggaacggc tgcaggtgct    14580
tgagatggtc cgggcgggga cgatcaaggc gaagaaggtt ggcgataatt atcgaatcct    14640
gggctccaat cttgtggaat acatgaaccg atgaagttcg aaaattgcag agactgccgg    14700
gaagaggtcg tgtggtgggc attcaccgcc gatatctgca tgacccttt caaaggcatc    14760
ttggggctga tgagcggcag cgtcgttctg gtggccgatt cgctgcattg gggtgccgat    14820
gtggttgcca gcgcgtgac ccagctgagt cttaagatct cgaataagcc tgcggatgag    14880
cgctacccgt tcggatacgg aaatatccaa tacatctcgt cggccatcgt ggggtcgctg    14940
ctgctgatag gcgccagctt cctgatgtat gggtcggtgg tgaagctgat ttcgggcaca    15000
tacgaggcgc ccagcatttt cgccgccttg ggcgcgtcgg tgacggtgat cgtcaacgag    15060
ctgatgtatc gctaccagat ctgtgttggc aacgaaaata acagcccggc catcatcgcc    15120
aatgcctggg acaaccgttc ggacgccatt tcctcggcgg cggtgatggt tggagtgatc    15180
gcctcggtga tcggttttcc catcgccgac accatcgccg ccatcggcgt gtcggccctg    15240
gtcggtgaca tcggtctgga attgatcgga aaggcggttc acggcctgat ggacagctcc    15300
gtggataccg aactcttgca gacggcttgg cagatcgcca cggatacgcc gctggtccac    15360
agcatctatt ttctgcgtgg acgccatgtg ggcgaggacg tgcagttcga tatccgtctg    15420
cgcgtcgatc ccaatttgcg gatcaaggac agctcgatgg tggccgaggc ggtacgccag    15480
cgcatccagg atgaaatccc acacgcccga gatatccgcc tgttcgtcag cccggctccc    15540
gccgcagtga cggtccgggt ctgatcagga gagggaatc atggactttc ggcctgatca    15600
agtggtagcc cgcatccggg cgcggtgga aggcgctttg accgctcaat ccgtgcttgg    15660
aatcggggc gctctagtct tgattctggt tgttatagcc ctgcttcccg atcgctttac    15720
ccgtggggaa ggcaagaccg ccaccgccgt gtcctctggc gccgcgcagg cccttcccgc    15780
cgccttgcct gggttatccc ccttcacgcc agccaagccc ctgcagttca gcgggcgcgt    15840
cacccaggtt gccagcatcg gcaatgatgt gggctggggg caggtccatg tctggatcga    15900
caacggtaca ggggccttgc aggaaatttc ggtggcgccg caatcctatc tcaaccagat    15960
tggctgcccg tcctttgacg gggcgcggat cagcggcatt ggtttcttgt tcgatgcggg    16020
acgtcccaat gccgagcttt acgccaagtc cgttctggtg gggggcgga catgcaagtt    16080
gcgcgatgac gagggtttgg cgctgtggat gaccgtgcag tgagccatat gggacagaga    16140
gggtgaacat gggtacgcca gggggcggcc gtcgctggat gaccttgatc tcgatcacct    16200
tgctgatggt ggtcggactg ggactctatt gggatgagct gtccctctcc gccggcatct    16260
```

```
ccccgccac atcgccccgt cggcggagg ggcttttgtt ggggcggctg cccttgccca      16320
tggagccttc gattctgtcg ccgctggagc atctcattga ccgccgctt cagtacaagc      16380
tgatgaccat tcgtcatatc ccgccggtaa tgccggggac aggcatgccc catccctatg      16440
tgggggattg catccaatgc catctgatgg tcggtggccc cgctgccgga tcacagttca      16500
agacgcccta tggcgccgta ctggaaaacc tgtcgcgggt ccgcaaactg gggcctccca      16560
ttcttcccac gacgcgccag ccgcatccgc ctgccgggcg ctgcattaag tgccatgaca      16620
ttgtggtcaa ggtgcctgtg gaaaagaagt ccggcattaa atggctgttg taagcgccgg      16680
tgtcgtcctt cgctgaacag gggctgtgtg gaagatgcgg atcgccgcaa tcatcaatgc      16740
gcgggccgga accgtgcttc ggatgtcgcc ctccgccgtg acggagcgac tatcggtcgt      16800
ttggggctcg cttgggcatg atgccgcgat cattcttgcc gaaggtaagg acatggggcg      16860
gatggtccgg aaggcttgcc gcgatcccga catacgggcg atcatcatcg gcggcggtga      16920
cggatctctg tcacgggctc tcgaacatgt gctcgcaagc ggcaaatcgc tgggtgtcct      16980
gccctgggc accatgaact acatggcgcg tcagatcgga atgccgttgg atctggccca      17040
ggcggcggtg gccttggcgg gagccgtcca gactcccatg gatgtgggac gggtcaatga      17100
tcgttatttc cttatccgag cctgtttcgg gcgctttccc gaattcattc agtcgcgcga      17160
ccgggtccgg cgcaagggg gaagcttttct tgaaggcgcc ctggccggat tgagcggagt      17220
ggcgcggcgc tatcggattg tggaggcgga attgtccagc caggggggc gcgcccggat      17280
cgccacaagc ttcctgatga tttccaacaa tctgtgccgg gactccgacc cgttcctgct      17340
ggagcgtgaa cggatggatg gcggatccct ggggtttat gtgggcgca gcgccggacc      17400
ggtcgggctc atggaattgg gacttcaggc cgctatgggg cggtgggcca gcaacgaagc      17460
cttgttccag ggtgagatgc actggctgga ggttcaaacc gaacagcgca agccgctgat      17520
ttccattgat ggcgaggtgg agaaaatgga aggtcccttc cgcttcgaca ttctgcccgg      17580
agcgctttcc atactggttc cgaaataacg ccgccatggc catggtggtg cagttgcctt      17640
ccataccgcc ctactgccat ggaactggcg cccgctgccg cgcgtcgccg acagtcaggc      17700
agcctgatcg gtcagcaggg tggccccgga gccgactagg ccggcgtggg taggcttcct      17760
cgagatctta tccctgcatg gttatttcat tcaaaggggg gagtgtcaga ttacagtgcg      17820
ttgactgata cttttggcgc gaccgaatct acgcttgcgc gttgcgccgt ttttaatccc      17880
gtgttaccaa tgaattggaa acttttgttc acgttgcccc gaagagatgg gctcggtcat      17940
gaaaatatt gcggaccccc ttccgtttga cggtgacgaa ccaatgccca ggcgccttca      18000
tatcgtcagc gggcaggtgg aaccgttgcc ggacgacaac acggaccagg cgttgatagc      18060
ccaacagccc gcagccatgg aggagacgga catcgtcgct ctgctgcagg aatgtgaggg      18120
cgacgaggac ggccttccca ccgcggcctt cgataccccc ttcccttccc ttcccaaacc      18180
cgaacccgaa gcgctggccg agaaggtacg ggcccctgtc cctatgtcag gcatcggcga      18240
tcacggggat gccatcatgg ccgtgattcg tgacgccctt gaggcggagc ggcaccatgc      18300
cgatcaggac cttgtggcgg ctcgcattcg gaccgaaacg ctgagcgccg agatcgacga      18360
cctgcgccgc tcggtcgagg atgttcgccg ctcggcctca gagcaggtcg aggccactcg      18420
cgcggtggcg gctgagcaga tcgaggccgc ccggtcggat gcggccgagg ccattgggca      18480
actgaccctg acgttggatc aagttcggca gttgcgggct caggtagact cccagagtaa      18540
acatttatcc gccctgatcg gcattgagga aaaagcccgt agcctcgacg cgcaattggt      18600
cgaagagagg acccgcaacg ccgaattaca ggagcgcatg caggtggtcg ccgagggccg      18660
```

```
gactgctgcg gaggaaacgg ccgcgaaggc gcgggcggcg gccgagttgg cccgacgcga   18720
actggccgcc ggaagggcgc tccatgccga accgagtggt gtcggcgaga ttgtggcaga   18780
acatcgtgtt ccggtggtgt atggcggcgc cgtgtcgggc gcgctgtttc cggttcagat   18840
taccgcggtg gtcgaaaccc agacctcggc cgaagatcgc accggcctcg gcgccctatt   18900
cgatatccgg ctcgccaccg ccattccttt ggacaccgcc agtgggccgg catctcccca   18960
cgaagtggtg gaccgggtgg tcagcctcgc ccattccatg tatccgaacg cggtgctgac   19020
catcgctttc ggcgacgatg gcgaccgccg ggccgtacag ggccgctatc aggatgtcac   19080
cttcacctcc gccgatgtcg atgaccgtcg gcgcaaggcg gcccaagtgc tggccatcgc   19140
cgcaggcaac ttgtcgcagt agcctgatcc gctatggtaa gcgcatcatg tccggatccc   19200
atggcgttcc gctcgtcctg gtgtccctgt tgataccggg aagccctggg ccaacttttg   19260
gcgaaaatga gacgttgatc ggcacgtaag aggttccaac tttcaccata atgaaataag   19320
atcactaccg ggcgtatttt ttgagttatc gagattttca ggagctaagg aggctaaaat   19380
ggagaaaaaa atcactggat ataccaccgt tgatatatcc caatggcacc gtaaagaaca   19440
ttttgaggca tttcagtcag ttgctcaatg tacctataac cagaccgttc agctggatat   19500
tacggccttt ttaaagaccg taaagaaaaa taagcacaag ttttatccgc cctttattca   19560
cattcttgcc cgcctgatga atgctcatcc ggaattccgt atggcaatga agacggtga   19620
gctggtgata tgggatagtg ttcacccttg ttacaccgtt ttccatgagc aaactgaaac   19680
gttttcatcg ctctggagtg aataccacga cgatttccgg cagtttctac acatatattc   19740
gcaagatgtg gcgtgttacg gtgaaaacct ggcctatttc cctaaagggt ttattgagaa   19800
tatgtttttc gtctcagcca atccctgggt gagtttcacc agttttgatt taaacgtggc   19860
caatatggac aacttcttcg ccccgttttt caccatgggc aaatattata cgcaaggcga   19920
caaggtgctg atgccgctgg cgattcaggt tcatcatgcc gtttgtgatg cttccatgc   19980
cggcagaatg cttaatgaat tacaacagta ctgcgatgag tggcagggcg gggcgtaagc   20040
ttacaatttc cattcgccat tcaggctgcg caactgttgg gaagggcgat cggtgcgggc   20100
ctcttcgcta ttacgccagc tggcgaaagg gggatgtgct gcaaggcgat taagttgggt   20160
aacgccaggg ttttcccagt cacgacgttg taaaacgacg gccagtgagc ggcgtaata   20220
cgactcacta tagggcgaat tggagctcca ccgcggtggc ggccgctcta gaactagtgg   20280
atccttcatg tactgcggaa cagtcgcggc gtctccatgc tcgacgcagt tgtggcgggt   20340
ggcagcaacg cctcctcggc cttaaccgac gcgtccact caatggtggc gacaccagcg   20400
caggacgggc aacaagccgc ccacgcctcc accacgcgag cacaagcacc acagacccaa   20460
gcaggagaga gcgaagcctc atgctcccgc cgccgccaga tctcagccga ccgcgccgac   20520
cctccaggct ccctttcctc gatttcggcc atcagccgac atcccagcgc atcgggagcg   20580
atcttcaatg ccgccatgat gtggcggcgt gccacccccc atttctgaac ggcaaaggca   20640
gcctctccgg cggccaagtg cccatcggga tgatgggggg cgattgccgc cagggcctcc   20700
agcctcttca ggcaagcatc ctgatcctcg tcgcgccaca atggtgcaca agcatcaagc   20760
agcactcgag caggaacatg tggccaaacg gacgccagca gggtctcggc ctctgccttg   20820
cgtccctcgg aaacctcggc ccggatcacg tgcaacgcag gaggcagaaa agtctggtcc   20880
gccgccatag cctcgcgcgc cagacgcaag ggacgagcgg gatcaccggg ggatgcctcc   20940
aaagcttgtc cctcaagcgc caccgatcgc caccgcgcag ccaccaaggg cgtcagccga   21000
```

```
ccagccagaa ccgcctcacc aatccaggcc tgggctgccc ccccattcccc agcccggatc   21060 ttggcggaaa aggcctctaa atcctctcgg ctcggcccgg cgggagcggc ggcgagtttt   21120
tcaacgacga caggctgtat cttatccacc accggagtcg gcggtggtgg cgggcccggc   21180
tttcgcgcga acagacgccc cttcgcggcc tccaaccggg tcggcgccac cggctgtgcg   21240
ggcgggcgcg gcaaaagccg gtccaggcgg gcggcaagtc cgggattgtt cagcagccgc   21300
gcagcctcgg ccgcgaagcg gcggccttcg ccgacatccc cactctctgc cgcatccagg   21360
gccgccagca aggcactcat gccttttttcc agcccccgtg cctgccggga tttccccagt   21420
ttggagggta ggtcggccac caatgccgaa agacgcgaca gggcggaaaa atcagaaac    21480 accaccagga tcacggccag aagaaccggc atattgctgt ccacgtgcca gccaagccat   21540
tccacctgca ccgatccgac attgtctgag aaccacaggg tggcaaacac aaccggcgac   21600
atgaaaatca acaggacgat caggcgtaat agcatggatc actcgtctcg agacgaggcg   21660
acggtcatgg ccatcgccga caattcagac aatgcagcat ccgcggacag acgcaattcc   21720
gccgcctcca gccagggttg gatggccgca agggacggcc cttccgcgcg acggagcaag   21780
gcggcagccc cggctaaatc gcccccggcc agcaaccggg aagtgctgtt caggatacca   21840
tccagcccct cttcgccccc ctcggtgcgt ctgatcaata ccgcacctcc cagccaccgc   21900
cggatatttg gtggcaccca accggaatcc gcgggacat caagcttacg tgccgcggcg   21960
gccgtcaccc gaaaactttc ggccaaaccc acacgggtga cgattcccgt cgccgagccc   22020
atcaccagcg gcgccagctt atcggcggtg cctttctcgg ccagtatcat ggccgctttc   22080
atctgtgcag ggtaaggact gccccggtca accgcttccc gcaattgtcc gagtgcggcc   22140
aggaacaagg gcgcgcgatc ccgccgctcg gcgatacgtc ggaaagccgc ctccgccttc   22200
tccaccgcac cggagagctt ggttgcgccc ccttcatccg ccgccaactt gcgaacaatc   22260
tccaagtccc cttaagcgt tgcgatctcc gccgccatcc aagacatctg ctccggatcg   22320
gcggaaacac cagccgcctc tttacgaggg tcttccccccg ccgtgcgggg attagcctct   22380
agcatggcta ggcgccggtc ggcctccgcg atccgcatag ccaggggagc cagggcggct   22440
tccaccatat ccatccgttc atccagggtc gcggacgcg gagcgccaac agatccgccg   22500
tcacctatcc aggacagcaa tgagccagga aaactcccaa ggcgaggtgc caaccaaggc   22560
catgccagca cggctacgac cacggcgatg ccagataca gaaccaggac ctgtccacca    22620
ccatcccggc gtcgagccgg acggcgacca ctcggtcccg gtgcctttc gttgatgtcc    22680 attggctccg cttccgctag ctgcgcggcc tgcaaccggg cccaaccgcc ccgcaacggc   22740
gattttcacg atcaccgatc cctttggcaa gacattaata ttatagatga aacggtcctg   22800
aaacagctga tgccctgcac agccgggcat cagacgtaaa tcacccgagg ccgaacctca   22860
gatccggtcg gccacccagc tgaccacggg cagtttccat gcccgctgga acaccacgga   22920
gaccaagccc agaagggaga ataccaggac ccccatggat gaaaacccga aaatccactt   22980
ccccagaacg ggaacatgca gcgcgaacag cgccagcacg ccccacatcc agatcaccag   23040
accctgcttg gcgtggaagt agacaaactc gtcgtcccga tccaccagca gcggaacgaa   23100
gcacaggacg ctgagataag acagcgccgc catgacggtc gtgcgcgcgc caagagtgct   23160
ccgaaggatt gcttcaacca tgtccccccc ccccgttca ggacagcgcg tcgcgcagtt    23220
cgacttcttc atcgctctgt gccgcttcga tatcacggct cttcatatag gcgtagactg   23280 cccccggcccc gacgacaccg aggatgagcg gcccccaagc ccaaggccc ataccgagcc    23340 ccagggcaag ccccttaccg gaccagatgg tgccgccgac agccttggcg ccggcgccga   23400
```

```
ccttcccaac gccaaccgca gcggccttgg ccccagcgcc ctgcgccgcg acaaccttgg   23460
ttccagcccc ctgcgccgcg gcgggcgcgg ctccggcctt ggcagcgcca accttgcccg   23520
cgccaacctt ggcagtcgcg ccttcgcgtt ccatttcacc cagggcggcg gccttggttc   23580
cgaccggaac cccagggggg caaaccattc cgttggcgat ctgagcaggc accagagttc   23640
tccttagcaa tcaagtagtg cgggactgaa aaacatcagc ctcaccagac atacaattca   23700
ataccatgag gttgccgaat aggacaacct gtatggggct aaaaaacact attacatgga   23760
agttacgagc gattattatc tgcaccgccc ccgctagctg cgggttattc gcatttgcct   23820
ctgcgcgggt tttgacagca gcccctgttg cacccggccc cgctgtcgcg gttcttgtgg   23880
acacagcgaa gcaccgcagc tcccgccaaa accacaagcc caataattgt cgacaaatcc   23940
caaagagtaa gcacgggacg atcccttaac gccaatgacc accaccacct taaacctccc   24000
cacagaaatc tgccaccgtg agcaaagcac cctgtttggc aggcatggcg cgcagcgatg   24060
accagggaag gaattgacag gtggagtcca gtcagcccta cctaagcgcc cacgacagca   24120
taaggaataa ctctattttt gcacaccccg tcgcctgaag ccaccttgac agaaattgat   24180
atctattctc aacttttttcg ctttactagc tcttagttct ccaataaatt ccctgcgtcg   24240
attttaaggg gcagagaggg aatcgtgcat acacttgccg gagatcagat gatcaagggc   24300
atcgcgggag ttggcggaac cgccccttgg cgtcggtggcg gagttgccgc ccctccggtc   24360
tctgccgctg ctgtcggcag caccttgctg gccggcaagg gggtgtgcct ggggctgggg   24420
cttggcctcg gtgcttgggg tcccgttctt ctcggcgttg ccggattggc ttgcgccgcc   24480
tccctatgtg attatctgaa gaatcgcaaa gcgcaggctg aggcctccgc cgagcctgct   24540
taagcgaggg caaagcaatg gccgagacta ttttgatcga aactaaaacc gctggcggca   24600
actgccgttc atatctgatg gcgggcgcta gctatctggg catcctctgc ttcgtcccgc   24660
tgcttatgag ccgcgatgac gaatatgtgt acttccatgc caagcagggg ctggtgctgt   24720
ggatgtggag catcctggcc atgttcgcgc tgcatctgcc gggcatcggc aagtggctct   24780
tcggcttctc gtccatgggc gtcctgatgc tgtccgtggt cggcttggtc tcggtggcgc   24840
tgcgccgcac ctggcgtctg cccctgatca gccatgtagt cgcccgatc tgacggcgag   24900 cgatctaacg gacccggaca gcagcgcaag caggcgaccg gagtcctttg ctttggagtc   24960
ccaagcggct tctgccatgt aggcgcagtt tcgtctcagg aaaggccaat accatgcagg   25020 accttttttct cgccaaggtc gaaagcgcca tgcaggcgtc ccaggtcggg gcacttgccg   25080
gtcagacggc gacggtctcg tcagtctcgg ccacgaccaa tctggccacc ataaccccaa   25140
ccaccgccgg gcaggcccct atcatcgtca aactggacgc ggcacggcag gtgacggagt   25200 tgcaggcccct gatgggaaag accgtgctgg tcggaaagac cccgaccacc atcggcggca   25260
tcggaaactg gattgccttg accccggcgg cgggagccaa gaccggcgct gccgtggccg   25320
gaaccggtca gctggtcatg atgaaggtcg agggcaccgg cgcggccatc aagcttcccg   25380
ccctggcggg taagagcttc atcgtcgccc agcccccgt agccgccgga accaaagcgg   25440
cgggcatgct ctatctgaat ccggttggcg gtggtgatat ggtggccatc aacattcaga   25500
acgccatgac ccagaccggc ggcttggtcg gcaagacctt caccgtcgcc cccagccccg   25560
tcattggcgg caccaccggt aaattcctgg tcctgaagcc catggcgacc ggggtcggca   25620
aggcggtggg cagcggcgcc gtcgtcgcca agttcgtacc cgccgccgtc accggcacgg   25680
gcggagcggc ggctatcggg gccggatccg ccaccaccct gatggccacg ggcgccagta   25740
```

```
cgatcacccc cgtcactgcc gccgccgctg gcagcgccat gctgacagcc aaaggtgttg    25800
gcctcgggct tggcctgggc ctcggcgcct gggggccgtt cgccctaggg gctatcggcc    25860
tagcgggtgt tgtcgcgctt tatacctggg cgcgccgccg ccatggcgct cccgatgttt    25920
ccgatgacgc tcttctggcg gctgtcgcg  aggaataagc ctgacccttg aattaaggac    25980
aacagcgatg agctttcaac ttgcgccgta cttggcgaaa tccgtccctg gaatcggcat    26040
tctcggcggc attgtcggtg gcgccgccgc ccttgccaag aatgcccgcc ttttgaagga    26100
caagcagata accggcacag aagcggccat cgacaccggc aaggaagccg ccggcgccgg    26160
gcttgccacc gctttctccg ccgtcgccgc caccgccgtc ggcggtgggt tggtggtctc    26220
gttgggaacc gccctaatcg ccggcgtcgc cgccaaatac gcctgggacc tgggtgtcga    26280
tttcatcgag aaggaattgc gtcacggcaa gtccgccgag gcgacagcgt ccgacgaaga    26340
cattctgagg gaagaattgg cctgaaatat tgggctggtt cacggcattc agacaccggc    26400
ggaggccagg gcgttggttg ttgttatcta aacaacgccc tggcagaacc gaacaagaac    26460
actgtcgtca ttcaccccga tgtgctctgg cgccgagcgt aagcatccgg tgagaacctc    26520
attccctcat gatacagaga ccggggactt atcagccaac ctgt                     26564
```

<210> SEQ ID NO 36
<211> LENGTH: 5549
<212> TYPE: DNA
<213> ORGANISM: artificial sequence
<220> FEATURE:
<223> OTHER INFORMATION: gene expression cassette comprising the mamXY
      operon of Magnetosprillum gryphiswaldense

<400> SEQUENCE: 36

```
acaggttggc tgataagtcc ccggtcttca cgctgccgca agcactcagg gcgcaagggc      60
tgctaaagga agcggaacac gtagaaagcc agtccgcaga acggtgctg  accccggatg     120 aatgtcagct actgggctat ctggacaagg gaaaacgcaa gcgcaaagag aaagcaggta     180
gcttgcagtg ggcttacatg gcgatagcta gactgggcgg ttttatggac agcaagcgaa     240
ccggaattgc cagctggggc gccctctggt aaggttggga agccctgcaa cgtataatat     300
ttgcccatgg acgcacaccg tggaaacgga tgaaggcacg aacccagttg acataagcct     360
gttcggttcg taaactgtaa tgcaagtagc gtatgcgctc acgcaactgg tccagaacct     420
tgaccgaacg cagcggtggt aacggcgcag tggcggtttt catggcttgt tatgactgtt     480
tttttgtaca gtctatgcct cgggcatcca agcagcaagc gcgttacgcc gtgggtcgat     540
gtttgatgtt atggagcagc aacgatgtta gcgagcagca acgatgttac gcagcagggc     600
agtcgcccta aaacaaagtt aggtggctca gtatgggca  tcattcgcac atgtaggctc     660
ggccctgacc aggtcaaatc catgcgggct gctcttgatc ttttcggtcg tgagttcgga     720
gacgtagcca cctactccca acatcagccg gactccgatt acctcgggaa cttgctccgt     780
agtaagacat tcatcgcgct tgctgccttc gaccaagaag cggttgttgg cgctctcgcg     840
gcttacgttc tgcccaggtt tgagcagccg cgtagtgaga tctatatcta tgatctcgca     900
gtctccggcg agcaccggag gcagggcatt gccaccgcgc tcatcaatct cctcaagcat     960
gaggccaacg cgcttggtgc ttatgtgatc tacgtgcaag cagattacgg tgacgatccc    1020
gcagtggctc tctatacaaa gttgggcata cgggaagaag tgatgcactt tgatatcgac    1080
ccaagtaccg ccacctaaca attcgttcaa gccgagaggc agcctcattt aaacattcag    1140
gacgcgctgc catattatac tattccgaaa ttaatactta gcaccacttt cccaacggac    1200
```

-continued

```
tcttaggcaa tgcaggtcct cacaaacaaa aggcggtgtt gcgattaatg cgcatcttcc    1260
ggtattgacg gactcgccac aaagccatat ctatcccttg tgtccaagct accttgccgg    1320
tcagcttgct gttactgtgg cagtatccta tacacaccag aacattttgg cgaccaccac    1380
agccaccacg ggagcagccc ttatgttgat gaactttgtc aacaatgtat caaagacgat    1440
taacggagga gcccgcatcg tatatgtcgg atcgttctcc tgggctgtct tatcacttct    1500
ttttgtcacc gctttcagtg gctggaataa tattttctca atgctccccc acgagatttt    1560
tattctagtt ctaaccattt cacttccgat tgctctgatt gttttgatct tcatgctctc    1620
gcagattgtg agaaccgtcg agagcgtgaa gtctgaaatt ccaccctgt cccagcggga     1680 tcctgtttcc gaagaggcgg tcaccatgct ggccgatctg ttccgcgaac atcgcgatgc    1740
cgttgccgcc caggtggcag cccaagtcga ggccaccgcc cagttggtcc agatcaatca    1800
ggacaaccgc gccctcgccg cgccctcgcc ggattcaggc gacgaaaacc ccctggcctt    1860
gctggcccaa atgttccgcg aataccgcga cagtgacg gcgcagctgg aagcgcaaat     1920
ctcggccacc acccagttgg tggaggcaag ccgtgacagc cgcgacggca tcgtcgatga    1980
actgcgctcc caacgggttc tgtcccagga aatcacccaa gaactatccc atatcgccca    2040
aagccggaat gtggttccgg tcgccagccc ggcctcgac ccgtcgcagc ggatcgaccg     2100
catgcgggcg ttggcggagg tgctggggct ggccctcaat gacctcagca tgaccgcaac    2160
ccagctcctg agcgagcacc tgaacgcggc ccatggcgac agggagggaa cacaaaagtt    2220
tatttcgacc ctgactaacg cctatttcgc gggtgacaag aacgtctttt ccgcagctt     2280 ggtcagcgag gtcgtcaacc attccgacca attgcagcaa tgcgcgattg gtgccgagaa    2340
tgtgcgccag cagatttcca aaatcctgcg cgaggcccgt gagatccgct cgctggtgtc    2400
cgcctgcgac cctaatgatc tggtccggat cgtcttcgag gatggcgagt gtgggccttt    2460
ggaaaaggcc ctggccgagc acttcctcat cgatggaacc cccatctccg atgcgtgacg    2520
aaagccgacg tccgaaattg catggccgcc atttccagct acggtccaga cggaaggccg    2580
atggtcattc cattgcgtat gggaatatga gatacttcgg cactttcatc gctagcgcat    2640 cgggaatcg tagctccact ttgaccacag tcgaactccc gtgaacacca aagccgttgc     2700
acatcccgac atcgccgtct ggatcatggc gttgggcatt gccttcagca tggccctagt    2760
tctgaccgcg ctgttcaatg ccaatccgtg gaagatcac acctacgatc tggcgcctcc     2820
cattgtcgct gggatggccg cccccatcg cgatggccgc gagaagatgg tctgctccag     2880
ctgccatatc gtcaccccg cttccgccgc taccggtccg ggcgcgggca cgctgcccat     2940
cgttgaggga accccggcgc cgcatgtgga tggacgcgag aagatggcct cgccagttg     3000 ccacaccatc gtgaagaagg gcagcgttgc caagagcggc aaggcaagcc ccgctccggt    3060
ggcattctcg cagggcatgc ccttacccga ggcgatgagc gtggcgctgg cggttacccc    3120
ggcaccggcg cccctgggca acgaagcgca tgagcggatg gtgcccttcc gctatcaagg    3180
caagatcgtc agcgtggcgg gcgctggcac ccgctcggtc tggggtgata tctatattca    3240
gatcaacgat gggatcaatc ctcccatgtg gatcgacctt gccccgctct ggttcctgca    3300
agcggagggc tgcttggtcc gtcccggtat gttcgtcaag gcaccgcct tccgcgaccc     3360 gacccaggcg agcgccgggc tggattacgc catgagcgtc atggccaatg gcgaagtctg    3420
tgccctgcgt gacgaccatc tcaacggcct gtgggctaat gttggaggcg tggatgccga    3480
agagcggtaa accctccacc ggcacgacac cggctgactt cgctcccacc caatggaata    3540
tcatctatct gctgatgacc gtgggctctc tggtggccgc gctgtccatc tctatccagc    3600
```

| | |
|---|---|
| ccctgctgct ggataagatt ttcggcattg ccttcgaaaa agagggcgcg gtcaacgccg | 3660 |
| atattcaggt ggtggcagag atcgtctcca tcgtctgcgt gggatggttc ggcctgctat | 3720 |
| ccgatcggat tggccgggtt cggatcatcg ccacgggctt cctgatcgcg gtggctggcg | 3780 |
| cggccatgtc cctgctcagc ctgcaaattg ggctcgcctt cggtgccgcc gggctggtgc | 3840 |
| tgttctatct gacccgggtg ctgctgacag tgggggccga taccgtccag ttgcagcttt | 3900 |
| ccaccctggt gggcgatgtc tcctcgcggg ccaaccggcc gcgcctgatg ggaaatttgg | 3960 |
| tgttcatgat ggtcttcggc ggcaccatgc tgtcggccat catcatgcag atggccgatt | 4020 |
| ataagggcgg tgtgttcatc atcatgtgcc tgccgctgct gatcggcatc gccgggttcc | 4080 |
| agatgacgcg cgaatccttg cgggatgtag cacagcccca gcaagcgccc acgggagacg | 4140 |
| agcatcccct tcggcaagtc tggtcggtga tcaccagcga cccgcgcttg caattggcct | 4200 |
| tcgccgccgc cttctacacc cgcgccgacg tgatcatcct cagccttttc ttctcgctgt | 4260 |
| ggtgcatttc cgtgtcggat ctggtggggg tgacccgcac ctacgccacc gcccatgccg | 4320 |
| ccgtgatgat cggtctattg gggctggcgg ttctggcggc aatcccgctg tggcgatcct | 4380 |
| tcatcgagcg ccacagccgc atttccgcca tcggggccag cctttccctg gcggcggtcg | 4440 |
| gctatatctg gctcggaatg ttcgccaatc ccttcaactg gctggtggcc ttgccgttgc | 4500 |
| tgatggtagg catcggccat gccggatgtt tcgtgactct tcaggtcctg actgtggacg | 4560 |
| tctcgcccaa gccgatcctg ggcgccatgg ttggggcggg ctatctggtg gcggccttg | 4620 |
| gcaccgtcat gctggtgcaa agtggcggct attatttcga tgcgcttggc ccgcgcgcgc | 4680 |
| cattcatcct gatgggaacc ggcaagatgc tggtgaccct ctacgccgcc tggctgctgg | 4740 |
| ccaacggcat tgatgagacc tgcgatcacc accttaaatc cacccgcaag gtggattgga | 4800 |
| agccgctggt gttcctgacc gcggccctcc ccttcgtctg gctgatcggg cgcagcgtta | 4860 |
| tcgaaggata tttctccaac ggctctctgg gcgaggcccc ggtcggtttc gtcaaccgct | 4920 |
| atttgggcga ttgggccttc accttcttga tcatctcgct gtccatgcgc ccggtgcagg | 4980 |
| agattactgg catcaagtcc ctggccaagt accggcgcat gatcggcctg ttcgccttt | 5040 |
| tctacgcggt attgcacgtt ctggcctatg tcaccctgga atgggcgctt aatctgggcg | 5100 |
| acatggcgag cgacatctac aagcggccat tcattctgct cggcctggcg gccttcctcc | 5160 |
| tgctgatccc cctggccttc acctccacca acagccagat caagaagatc ggcggcaaac | 5220 |
| gctggaaaag gctgcatagg gccacctatg tcatcaatgc cctggtggcg ctgcatttca | 5280 |
| tccttgctgc caaccacgag aatggcgaac cctatgtcta tgcggcggcc gtcatagttc | 5340 |
| ttctgtggta ccgtttctac cagtggcggg gcggcaatgt gctgcgcgcc ctgcgaatcg | 5400 |
| gctaaagaat tcgatatcaa gcttatcgat accgtcgagg tcgagggggg gcccggtacc | 5460 |
| cagcttttgt tccctttagt gagggttaat tgcgcgcttg gcctcattcc ctcatgatac | 5520 |
| agagaccggg gacttatcag ccaacctgt | 5549 |

<210> SEQ ID NO 37
<211> LENGTH: 4163
<212> TYPE: DNA
<213> ORGANISM: artificial sequence
<220> FEATURE:
<223> OTHER INFORMATION: gene expression cassette comprising the feoAB1
      operon of Magnetosprillum gryphiswaldense

<400> SEQUENCE: 37

| | |
|---|---|
| ctgtctctta tacacatctg acgtcgagcc acggcggccg aagcaggggg gcaaggctga | 60 |

```
aaagccggcc cccgctgcgg ccccgaccgg cttcaccttc aacccaacac cggacaaaaa    120
ggatcgccaa ttctcatgtt tgacagctta tcatcgataa gctttaatgc ggtagtttat    180
cacagttaaa ttgctaacgc agtcaggcac cgtgtatgaa atctaacaat gcgctcatcg    240
tcatcctcgg caccgtcacc ctggatgctg taggcatagg cttggttatg ccggtactgc    300
cgggcctctt gcgggatatc gtccattccg acagcatcgc cagtcactat ggcgtgctgc    360
tagcgctata tgcgttgatg caatttctat gcgcacccgt tctcggagca ctgtccgacc    420
gctttggccg ccgcccagtc ctgctcgctt cgctacttgg agccactatc gactacgcga    480
tcatggcgac cacacccgtc ctgtggatcc tctacgccgg acgcatcgtg gccggcatca    540
ccggcgccac aggtgcggtt gctggcgcct atatcgccga catcaccgat ggggaagatc    600
gggctcgcca cttcgggctc atgagcgctt gtttcggcgt gggtatggtg gcaggccccg    660
tggccggggg actgttgggc gccatctcct tgcatgcacc attccttgcg gcggcggtgc    720
tcaacggcct caacctacta ctgggctgct tcctaatgca ggagtcgcat aagggagagc    780
gtcgaccgat gcccttgaga gccttcaacc cagtcagctc cttccggtgg gcgcggggca    840
tgactatcgt cgccgcactt atgactgtct tctttatcat gcaactcgta ggacaggtgc    900
cggcagcgct ctgggtcatt ttcggcgagg accgctttcg ctggagcgcg acgatgatcg    960
gcctgtcgct tgcggtattc ggaatcttgc acgccctcgc tcaagccttc gtcactggtc   1020
ccgccaccaa acgtttcggc gagaagcagg ccattatcgc cggcatggcg gccgacgcgc   1080
tgggctacgt cttgctggcg ttcgcgacgc gaggctggat ggccttcccc attatgattc   1140
ttctcgcttc cggcggcatc gggatgcccg cgttgcaggc catgctgtcc aggcaggtag   1200
atgacgacca tcagggacag cttcaaggat cgctcgcggc tcttaccagc ctaacttcga   1260
tcactggacc gctgatcgtc acggcgattt atgccgcctc ggcgagcaca tggaacgggt   1320
tggcatggat tgtaggcgcc gccctatacc ttgtctgcct ccccgcgttg cgtcgcggtg   1380
catggagccg ggccacctcg acctgaggga ccctagaggt cccctttttt attttaaaaa   1440 tttttttcaca aaacggttta caagcataac tagtgcggcc gcaagcttgc atgcctgcag   1500
gtcgactcta gactacaaga atgtcccgcc gattcggctg gcggccaggg ccagcagcca   1560
agcgaaggac agggaataga ccaccgagaa tccggcccac cgccagctct gcgcctcctt   1620
gccgatgatg gcgatggtcg acaggcaagg cgcgtagagc aaggtgaaga tcatgaaggc   1680
gatggccgtg gcgggcggca tggcgcccct caaggtctcg gtcagctggt ccgaccccct   1740
ctcctgggca tagatgacgg cataggtcgc caccaccact tccttggcga caaagccggt   1800
catgatggcc gccgaatccc gccaggaaaa gcccagcggc tggaacagcg gcgtcacchc   1860
gatggccgaa cgcccagat agctcttttc cagcttctcc tgcgcctggg cgcttttcag   1920
cgtcttcagc gccgtttcct tttccgggct gtcgggaagc gtggtctgtt cggcgatgac   1980
cgtctcgaaa tcctgggaat aggtgatatc gcggggaaac tcctgaggga ccagatcac   2040 gatggagccc accaggatga cgccggttac cttggcgaca aagccctggg cgctgtccca   2100
catatggtgc agcaccgaat gcagggtcgg caggcgatag gcggcagtt caatcacgaa   2160 ggcgtcgcca ccgctgccgg ggatgatgcg gttcagcaac accgccgaca ccatggcggc   2220
gaccagggac agcatataca tggcgaagac cacggtgccg gcgatatcgg cgaagaaagc   2280
tccggcgaac aggataaaga ccggcagtcg ggccgagcag ttcatgaacg gcgcgatcag   2340
catggcgatc agacgcgccc gcttattggt gatgacgcgg gtggccatga cggcggggac   2400
```

```
attgcagccg aagccggcca ccatggggat cagggtagtg ccgtgcaggc cgaaatgatg    2460
catcacccgg tccatcagga agctggcgcg ggccagatag ccggtgccgc tgaggatggc    2520
catgaagaag aacagaatga cgatattggg caggaacacg atggttccgc cgacgccggc    2580
catgacgccg ttgaccacga gatcgtggaa catgccctcg ggcagggtct tgtccaccag    2640
atcggtggca atctgaacca aagctttgat ccagtcggtg ggaatggcac ccaggctgaa    2700
agtcgtctcg aacatcaccc acaaaatgcc cagcagcagg ggcaggccca aggtgcggtt    2760
caggaagaaa tcgtcgagga tgcgggtcag cttgaatccg gcggtggggt cgccctcctg    2820
ctggcgggct tcgcgcagca ggccgttggc aaaggcgaac ctcgccgagg ccagcaggcc    2880
ggcggtgtcc tcatcatgct cgtgggccag ggctgtctgc tcggccttga tctcctcgac    2940
cagttcgaca tggttgcttt cgtggcgcag aacctcgtca tcgccttcca gcatcttgat    3000
cgccagccag cgcgagcgca ccgggctcag ctcctggggg tgcagcttgg acagatgctg    3060
ctggacgcgc tcgatggccg cctccagatg gctgtcatag tgtagccgca acggggcggc    3120
ggcgggggtt gccgaggcca tggccgccac cgcgtccagc agggcatcga tgccctcctt    3180
cttcagggcg caggtctcca ccaccggcga tccgagggcc gaggccaata gggcggtgtc    3240
gatgcgaata ccgcccgcc ggacctcgtc catcatgttc aacacggtga tgcggggcag    3300
cccggtctcg atcagctggg tggtcaggaa caggctgcgg tccagatgac cggcatccag    3360
cacattgacg atgatgtcgg gttcctcgcc gtgaatatag tcgcagccga ccttctcctc    3420
cggcgattgc gacgaggtgg aaaaaatgcc cggcacatcg acgatgcgta agggaaccccc   3480 gccatgggtg atctcgcgca cattcaggga ggttgtaacc cgctgatagt tggcgacgga    3540
ggattgggcg cctgtcaggg cattgaacaa gctggtggaa ccggcattgg ggttacccac    3600
cagtgccacg gtgacggggg gtttcatata cggctaccct tgaagcgatg tcggatgggg    3660
tgattatttc aagcgaatgc ggatctgccg ggcctcggca ttgcgcaggc ccaggctata    3720
gcccatcagg ctgtagatgc gcggatctcc gagcggagca gagcgatcca gggttacagc    3780
agtcccggac accactccaa gcgactgcat acgacgcttg aaaacgccat cctcggtttc    3840
gatcttgacg atctcaccct gctgctcggg acaaaggtcg gcaagggtaa gagtgtcgat    3900
cttgacctgc tgatccatgg tacccacaat tcacctccaa ttcgcacgga ctatagcaac    3960
gaatcgaggt cggttgacaa gccataaaaa ctgggttcat acgaaggaac ctcgcaatgt    4020
ggcacactta gcgcgctagc acatttcgcg catctgctcg aaacaagacg tcacatcttt    4080
gcgccatcgc ctaccgatca ggatgccgaa ttcgcgcggc cgcggcctag gcggccttaa    4140
ttaaagatgt gtataagaga cag                                           4163
```